(12) United States Patent
Neogi et al.

(10) Patent No.: US 7,323,496 B2
(45) Date of Patent: Jan. 29, 2008

(54) COMPOUNDS FOR TREATMENT OF INFLAMMATION, DIABETES AND RELATED DISORDERS

(75) Inventors: Partha Neogi, Fremont, CA (US); Debedranath Dey, Fremont, CA (US); Joseph Fuller, South San Francisco, CA (US); Liang Chen, San Bruno, CA (US); Ta-Kai Li, Cupertino, CA (US)

(73) Assignee: Theracos, Inc., Sunnyvale, CA (US)

( * ) Notice: Subject to any disclaimer, the term of this patent is extended or adjusted under 35 U.S.C. 154(b) by 665 days.

(21) Appl. No.: 10/430,677

(22) Filed: May 7, 2003

(65) Prior Publication Data

US 2004/0097593 A1 May 20, 2004
US 2007/0259961 A9 Nov. 8, 2007

Related U.S. Application Data

(60) Continuation-in-part of application No. PCT/US02/38150, filed on Nov. 27, 2002, and a continuation-in-part of application No. 09/777,551, filed on Feb. 5, 2001, now abandoned, and a continuation-in-part of application No. 09/642,618, filed on Aug. 17, 2000, now Pat. No. 6,624,197, application No. 10/430,677, which is a continuation-in-part of application No. 10/075,442, filed on Feb. 15, 2002, now Pat. No. 6,855,732, which is a division of application No. 09/436,047, filed on Nov. 8, 1999, now Pat. No. 6,525,093.

(60) Provisional application No. 60/334,818, filed on Nov. 29, 2001, provisional application No. 60/180,340, filed on Feb. 4, 2000.

(51) Int. Cl.
*A61K 31/17* (2006.01)
*C07C 335/24* (2006.01)
*C07C 335/16* (2006.01)
*C07C 275/46* (2006.01)

(52) U.S. Cl. ............ 514/584; 514/585; 514/594; 564/23; 564/26; 564/44; 564/47

(58) Field of Classification Search ......... 514/584, 514/585, 594; 564/23, 26, 44, 47
See application file for complete search history.

(56) References Cited

U.S. PATENT DOCUMENTS

| | | | |
|---|---|---|---|
| 2,524,827 A | 10/1950 | Papa et al. |
| 3,275,520 A | 9/1966 | Strobel et al. |
| 3,609,183 A | 9/1971 | DeWald et al. |
| 3,683,009 A | 8/1972 | Middleton |
| 4,074,057 A | 2/1978 | Kawamatsu et al. |
| 4,217,366 A | 8/1980 | Kikumoto et al. |
| 4,271,186 A | 6/1981 | Forster et al. |
| 4,284,637 A | 8/1981 | Kikumoto et al. |
| 4,310,534 A | 1/1982 | Kikumoto et al. |
| 4,312,855 A | 1/1982 | Grand |
| 4,326,055 A | 4/1982 | Loeliger |
| 4,444,779 A | 4/1984 | Kawamatsu et al. |
| 4,716,905 A | 1/1988 | Schmued |
| 4,866,086 A | 9/1989 | Boyle et al. |
| 4,929,635 A | 5/1990 | Coquelet et al. |
| 4,940,707 A | 7/1990 | Klaus et al. |
| 5,087,637 A | 2/1992 | Janssen et al. |
| 5,162,337 A | 11/1992 | Elbrecht et al. |
| 5,171,753 A | 12/1992 | Munson, Jr. et al. |
| 5,189,056 A | 2/1993 | Orlando et al. |
| 5,246,936 A | 9/1993 | Treacy et al. |
| 5,250,562 A | 10/1993 | Klaus et al. |
| 5,314,693 A | 5/1994 | Suga |
| 5,378,705 A | 1/1995 | Klaus et al. |
| 5,391,565 A | 2/1995 | Hindley |
| 5,409,953 A | 4/1995 | Pettit et al. |
| 5,430,062 A | 7/1995 | Cushman et al. |
| 5,457,226 A | 10/1995 | Gygax |
| 5,494,932 A | 2/1996 | Cardin et al. |
| 5,521,160 A | 5/1996 | Chucholowski et al. |
| 5,525,632 A | 6/1996 | Obsumi et al. |
| 5,532,129 A | 7/1996 | Heller |

(Continued)

FOREIGN PATENT DOCUMENTS

EP     0332331     9/1989

(Continued)

OTHER PUBLICATIONS

Pettit et al., "Isolation, Structure, Synthesis and Antimitotic Properties of Combretasttins B-3 and B-4 from Combretum Caffrum" *Journal of Natural Products* 51:3 (1998) pp. 517-527.

Green, R. H., "Syntheses of Differanisole A" *Tetrahedron Letters* 38:26 (1997) pp. 4697-4700.

Reddy et al., "From Styrenes to Enanitopure α-Arylglycines in Two Steps" *J. Am. Chem. Soc.*, 120:6, (1998) pp. 1207-1217.

Sheehan et al., "A Constituent of *Ptercarpus marsupium*, (-)-Epicatechin, as a Potential Antidiabetic Agent," *Journal of Natural Products*, 46:2 (1983) pp. 232-234.

He et al., "Spectrometric Study of α-Phenylcinnamic Acids," *Chinese Chemical Letters*, 8:10 (1997) pp. 883-884.

(Continued)

*Primary Examiner*—Kamal A. Saeed
(74) *Attorney, Agent, or Firm*—Jones Day

(57) ABSTRACT

Novel acyl urea, thiourea, carbamate, thiocarbamate and related compounds are provided which are effective in inhibiting the cytokine-mediated inflammatory response in cultured cells, in ameliorating bone destruction in an animal model of arthritis and in lowering blood glucose levels in animal models of Type II diabetes mellitus. The compounds are disclosed as useful for a variety of treatments including the treatment of diabetes mellitus, insulin resistance, inflammation, inflammatory diseases, immunological diseases and cancer.

17 Claims, 9 Drawing Sheets

U.S. PATENT DOCUMENTS

| | | | |
|---|---|---|---|
| 5,559,151 | A | 9/1996 | Adorante et al. |
| 5,565,191 | A | 10/1996 | Raspanti |
| 5,565,322 | A | 10/1996 | Heller |
| 5,569,786 | A | 10/1996 | Pettit et al. |
| 5,583,128 | A | 12/1996 | Bhatnagar |
| 5,587,150 | A | 12/1996 | Deflandre et al. |
| 5,589,506 | A | 12/1996 | Hashimoto et al. |
| 5,672,625 | A | 9/1997 | Cardin et al. |
| 5,674,906 | A | 10/1997 | Hatanaka et al. |
| 5,686,478 | A | 11/1997 | Greenlee et al. |
| 5,705,530 | A | 1/1998 | Adorante et al. |
| 5,716,928 | A | 2/1998 | Benet et al. |
| 5,731,353 | A * | 3/1998 | Ohsumi et al. ............. 514/646 |
| 5,733,909 | A | 3/1998 | Black et al. |
| 5,767,268 | A | 6/1998 | Chucholowski et al. |
| 5,770,620 | A | 6/1998 | Mjalli et al. |
| 5,827,898 | A * | 10/1998 | Khandwala et al. ........ 514/734 |
| 6,245,814 | B1 | 6/2001 | Nag et al. |
| 6,262,118 | B1 | 7/2001 | Luskey et al. |
| 6,331,633 | B1 | 12/2001 | Neogi et al. |
| 6,525,093 | B1 | 2/2003 | Neogi et al. |
| 6,624,197 | B1 | 9/2003 | Nag et al. |
| 6,646,004 | B1 | 11/2003 | Luskey et al. |
| 6,855,732 | B2 | 2/2005 | Neogi et al. |
| 7,105,552 | B2 * | 9/2006 | Nag et al. .................... 514/369 |

FOREIGN PATENT DOCUMENTS

| | | |
|---|---|---|
| FR | 2254549 | 7/1975 |
| GB | 1496156 | 12/1977 |
| JP | 09059245 | 3/1997 |
| WO | 97/25042 | 7/1997 |
| WO | 99/50263 | 10/1999 |
| WO | 99/56737 | 11/1999 |
| WO | 00/69430 | 11/2000 |
| WO | WO 01/34094 | 5/2001 |
| WO | 01/95859 | 12/2001 |
| WO | 02/02501 | 1/2002 |

OTHER PUBLICATIONS

Chakravarthy et al., "The Prophylactic Action of (−)-Epicatechin Against Alloxan Induced Diabetes in Rats," *Life Science*, 29 (1981) pp. 2043-2047.

Farboodniay et al., "Antihyperglycemic Effect of Flavonoids From *Ptercarpus marsupium*," *Journal of Natural Products*, 56:7 (1993) pp. 989-994.

Manickham et al., "AntihyperLipidemic Activity of Phenolics from *Ptercarpus marsupium*," *Journal of Natural Products*, 6:60 (1997) pp. 609-610.

Maurya et al., "Constituents of *Ptercarpus marsupium*," *Journal of Natural Products*, 47:1 (1983) pp. 179-181.

Maurya et al., "Marsupsin, a New Benzofuranone from *Pterocarpus marsupium* ROXB.," *Heterocylces*, 19:11 (1982) pp. 2103-2107.

Online Database, Chemical Abstracts Service, Database accession No. 1941:25276, Spath et al. (1941) pp. 189-192.

Sullivan et al., "The Absolute Configuration of α-(+)-4-Dimethylamino-1,2-diphenyl-3-methyl-2-propionoxybutane, *d*-Propoxyphene," *Journal of Organic Chemistry*, 28:9 (1963) pp. 2381-2385.

Jacobsen et al., *Journal of Organic Chemistry*, 44:22 (1979) pp. 4013-4014.

Ryu et al., "Antitumor Activity of some Phenolic Components in Plants," *Archives of Pharmaceutical Research*, 17:1 (1994) pp. 42-44.

Jang et al., "Inhibitory Effects of Resveratrol Analogs on Unopsonized Zymosan-Induced Oxygen Radical Production", *Biochemical Pharmacology*, vol. 57 (1999) pp. 705-712.

Setala et al., "A Novel Type of Spiro Compound Formed by Oxidative Cross Coupling of Methyl Sinapate with a Syringyl Lignin Model Compound. A Model System for the .β.-1 Pathway in Lignin Biosysthesis," *Journal of the Chemical Society, Perkin Trans.*, vol. 4 (1999) pp. 461-464.

Hulin et al., "Novel Thiazolidone-2,4-diones as Potent Euglycemic Agents," *J. Med. Chem.*, vol. 35 (1992) 1853-64.

Sohda et al., "Studies on Antidiabetic Agents. II. Synthesis of 5-[4-(1-Methylcyclohexylmethoxy)-benzyl]thiazolidine-2,4-dione (ADD-3878) and Its derivatives" *Chemical & Pharmaceutical Bulletin*, 30:10 (1982) pp. 3580-3600.

Sohda et al., "Antiulcer activity of 5-Benzylthiazolidine-2,4-dione Derivatives," *Chemical & Pharmaceutical Bulletin*, 31:2 (1983) pp. 560-569.

Unangst et al., "Synthesis and biological evaluation of 5-[[3,5-Bis(1,1dimethylethyl)-4-hydroxyphenyl]methylene]oxazoles,-thiazoles, and -imidazoles: Novel Dual 5-Lipoxygenase and Cycloxygenase Inhibitors with Antiinflammatory Activity," *Journal of Medicinal Chemistry*, 37:2 (1994) pp. 322-328.

* cited by examiner

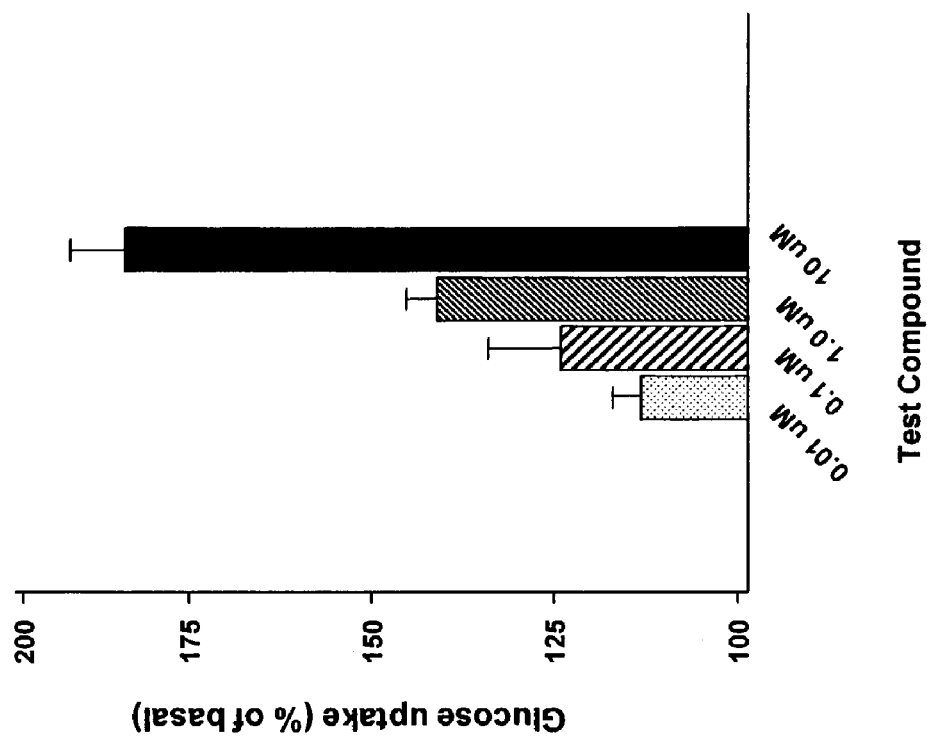
Figure 1. Increased Glucose Uptake in 3T3-L1 Adipocytes

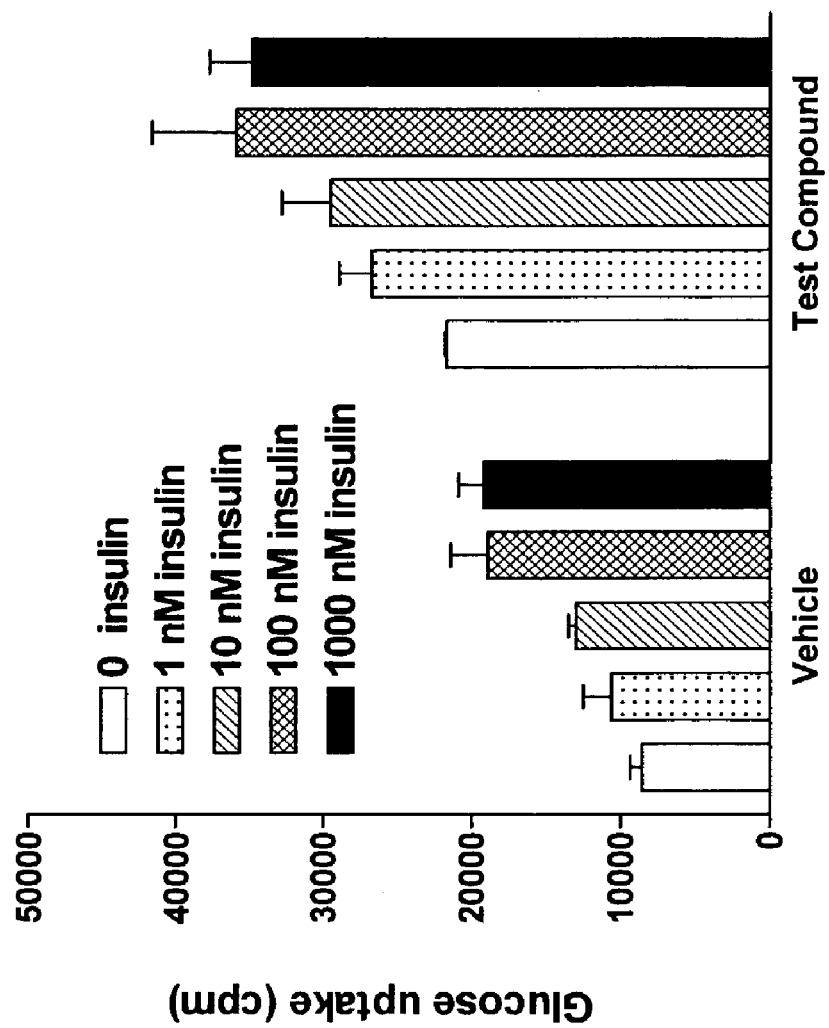
Figure 2. Enhancement of Insulin Action in 3T3-L1 Adipocytes

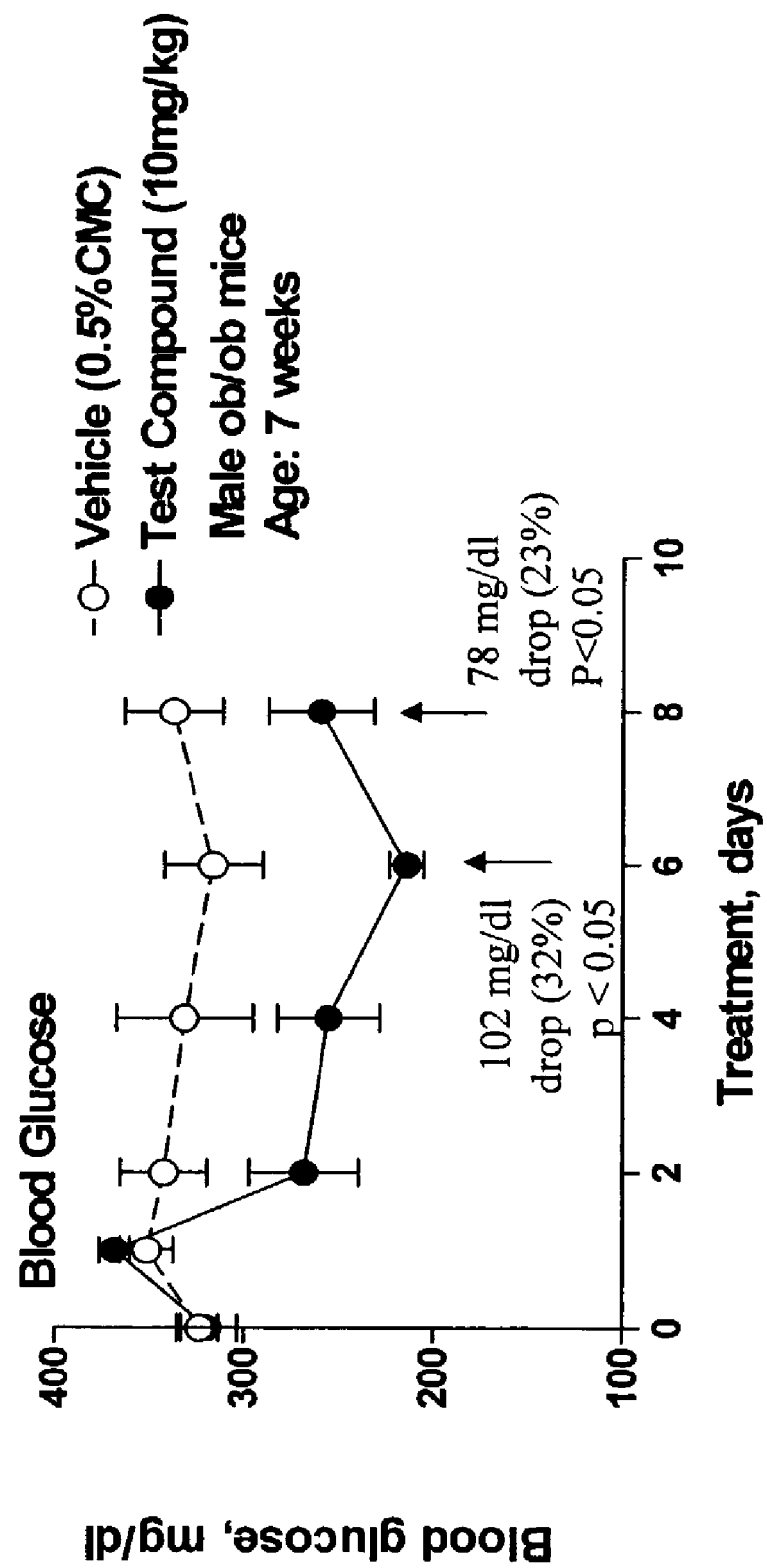
Figure 3. Glucose-Lowering Effect in ob/ob Mice

Figure 4. Lipid-Lowering Effects in ob/ob Mice
A. Triglycerides
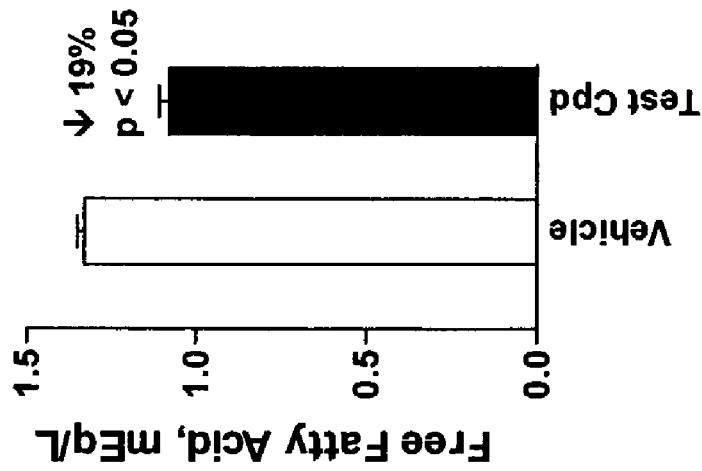
B. Free Fatty Acids
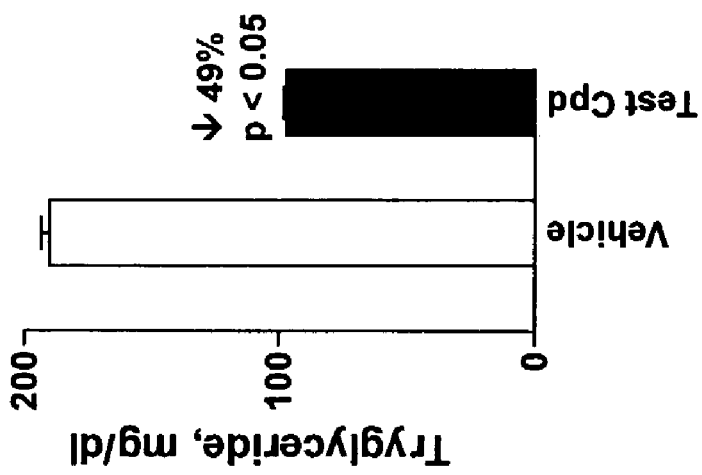

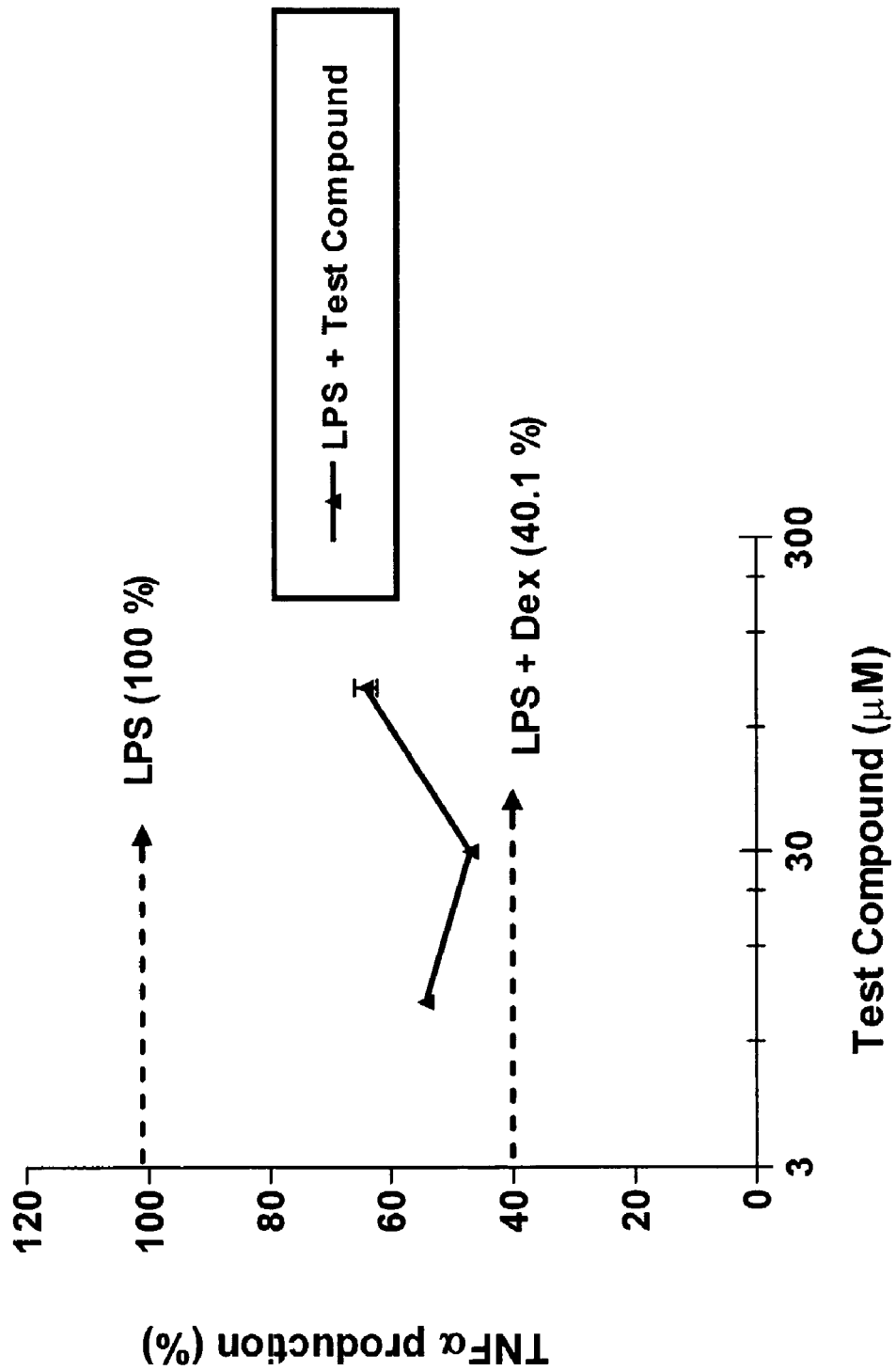
Figure 5. Inhibition of TNFα Production in RAW Cells

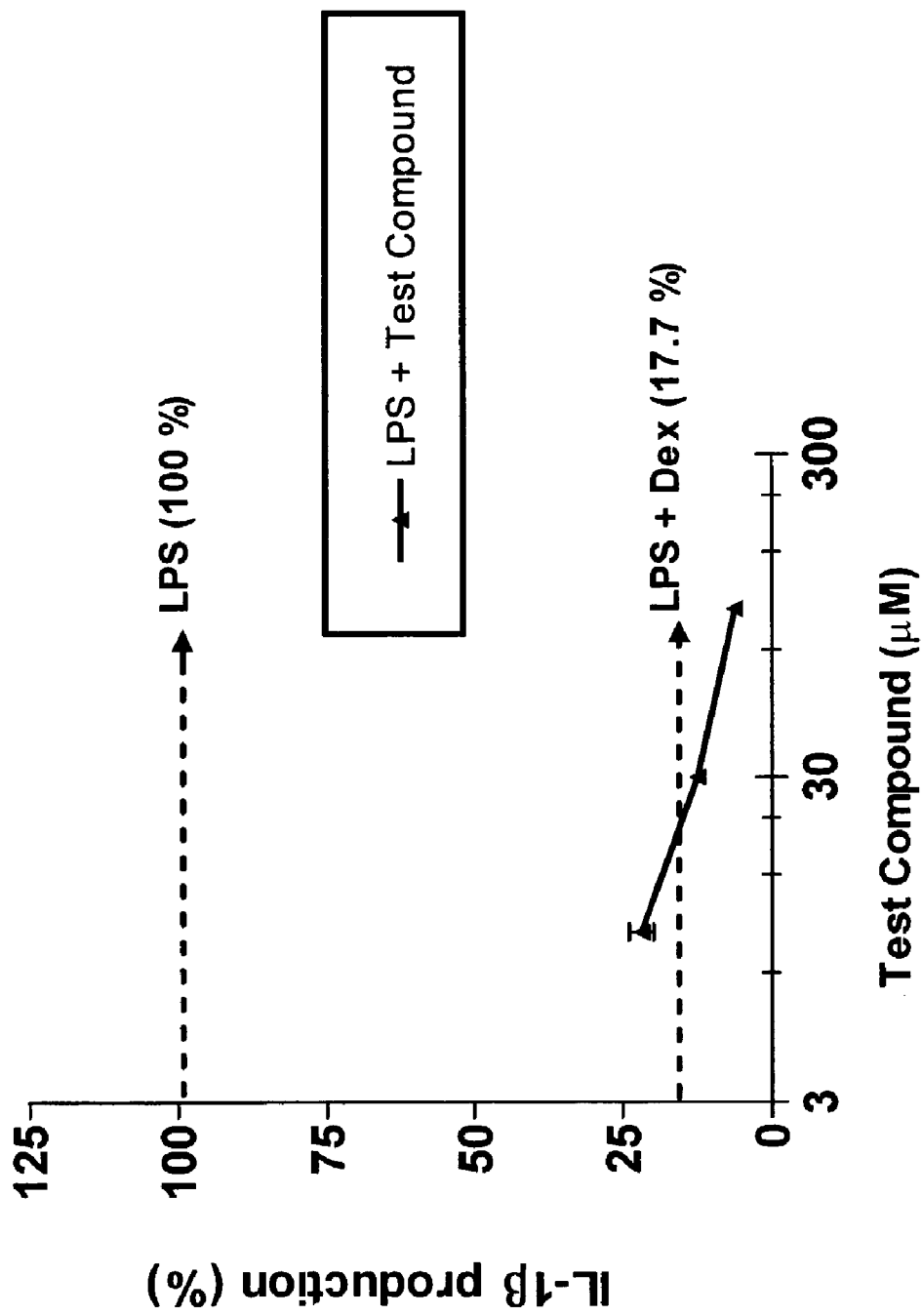
Figure 6. Inhibition of IL-1β Production in RAW Cells

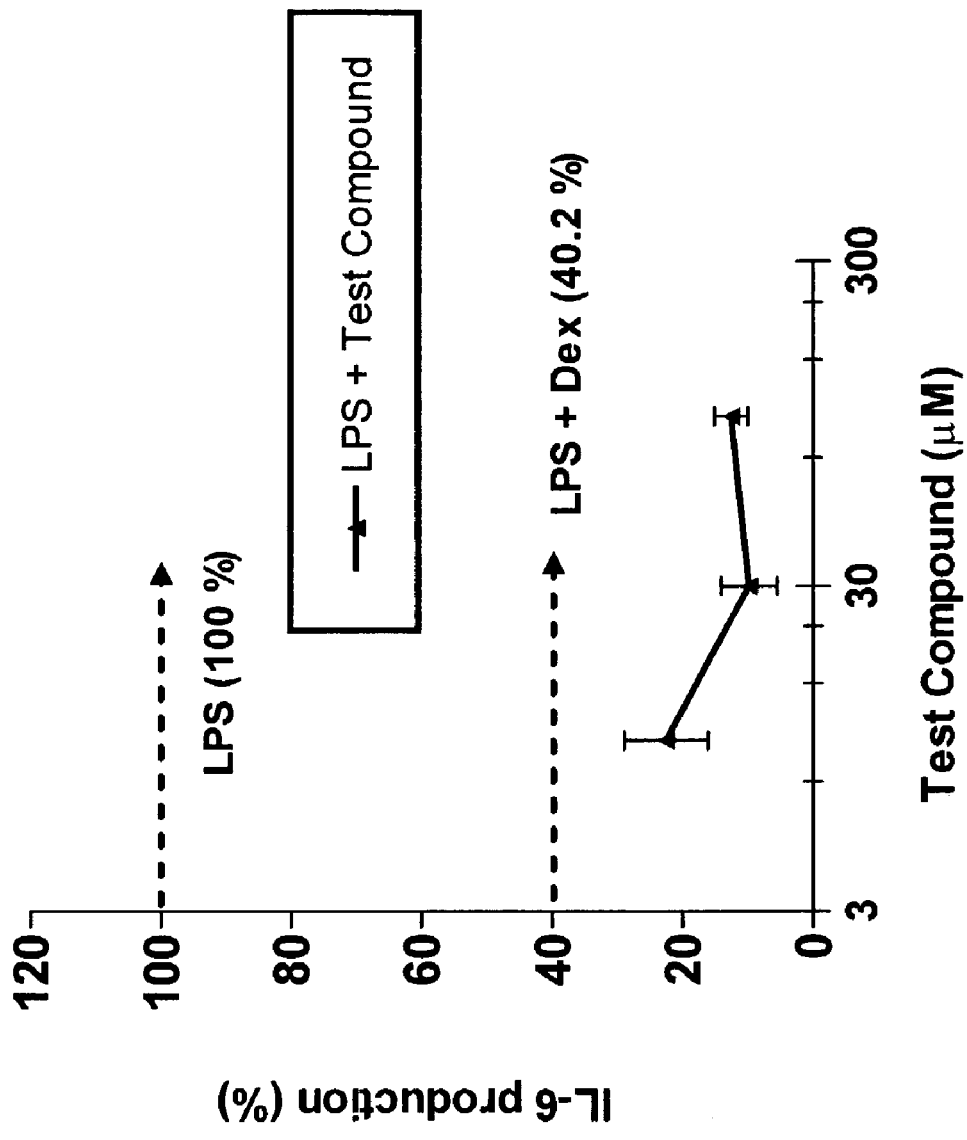

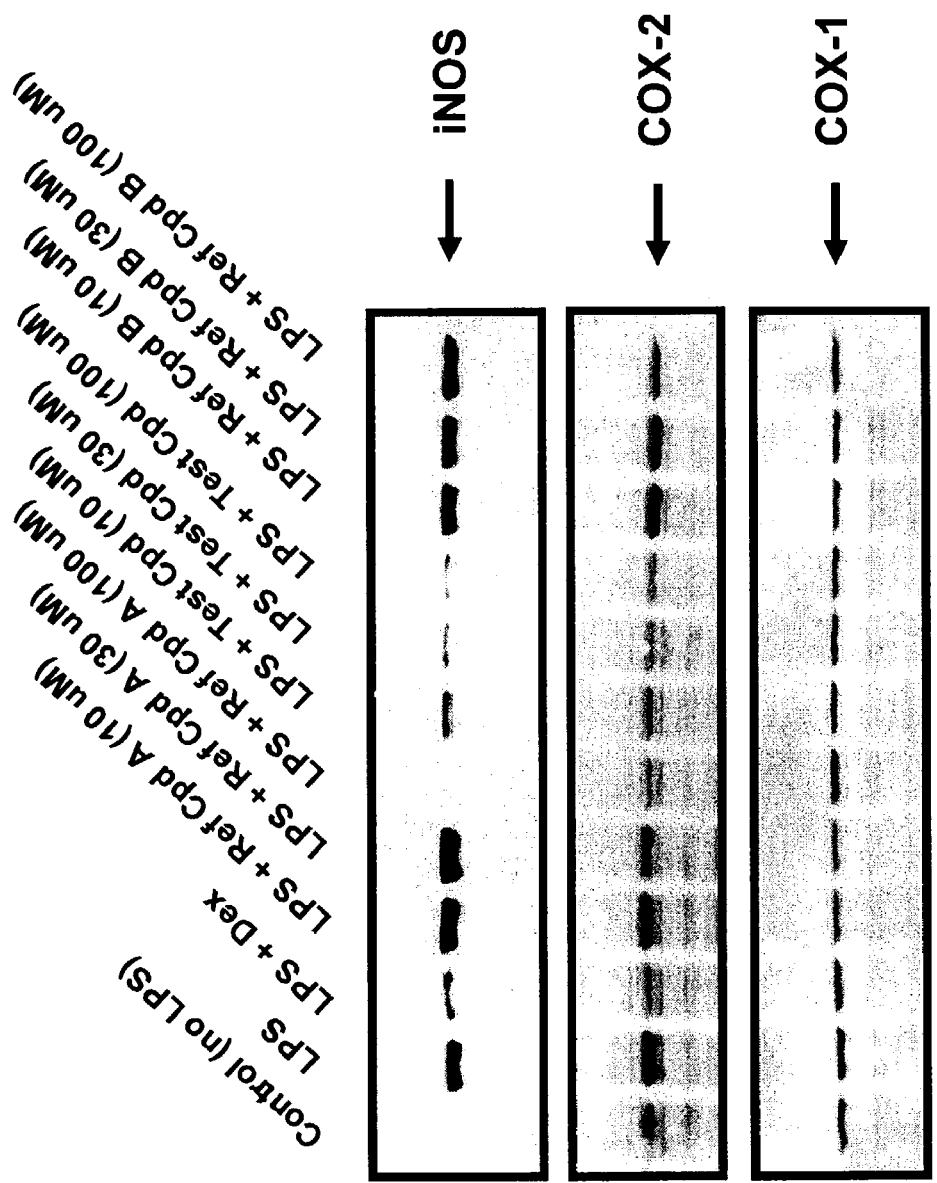
Figure 8. Inhibition of iNOS and COX-2 Production in RAW Cells

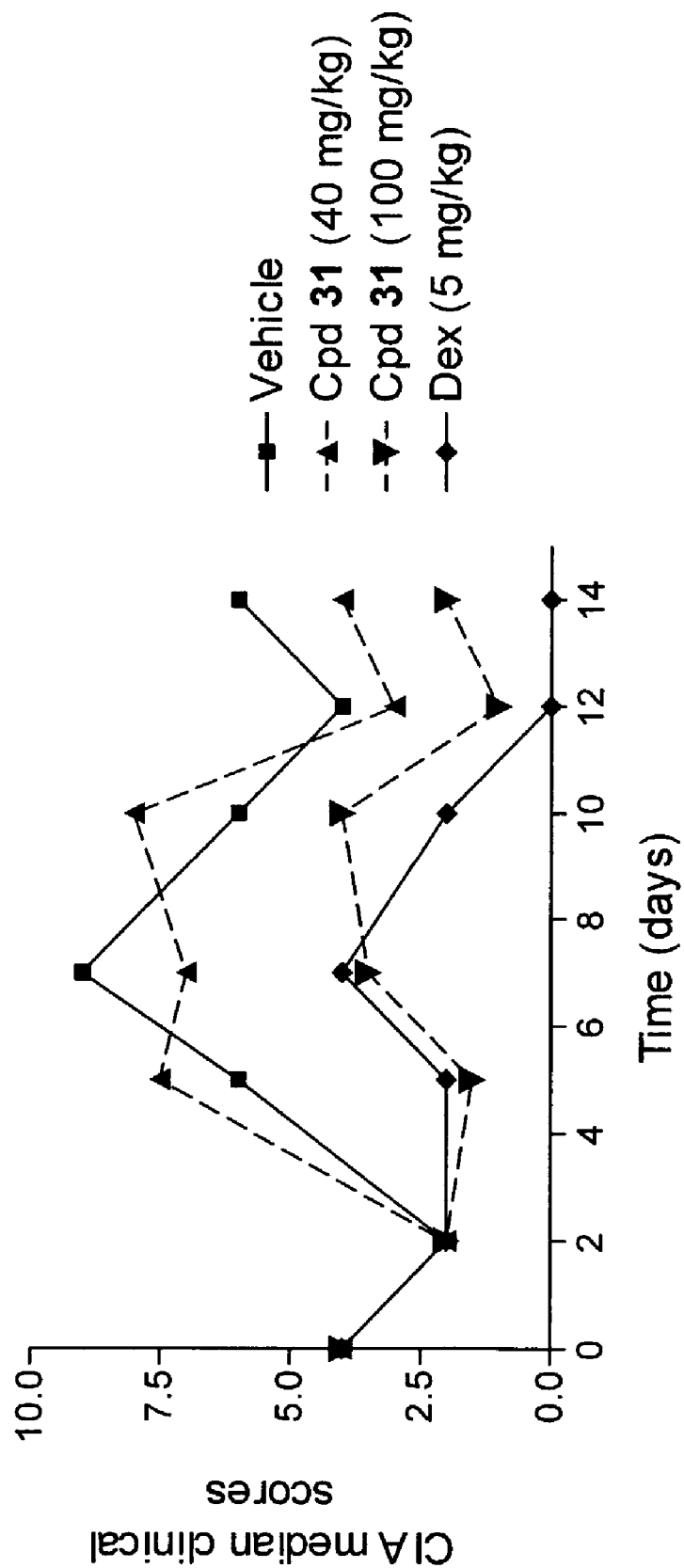
Figure 9. Improvement in Collagen Induced Arthritis in Mice

COMPOUNDS FOR TREATMENT OF INFLAMMATION, DIABETES AND RELATED DISORDERS

CROSS REFERENCE TO RELATED APPLICATIONS

This application is a continuation-in-part of International Application No. PCT/US02/38150, filed Nov. 27, 2002, which claims benefit of U.S. Provisional Application No. 60/334,818, filed Nov. 29, 2001, which are both incorporated herein, in their entirety, by reference. This Application is also a continuation-in-part of U.S. application Ser. No. 09/777,551 filed Feb. 5, 2001, now abandoned, which claims benefit of U.S. Provisional Application No. 60/180,340, filed Feb. 4, 2000 and which is a continuation-in-part of U.S. application Ser. No. 09/642,618, filed Aug. 17, 2000, now U.S. Pat. No. 6,624,197 issued on Sep. 23, 2003. This Application is also a continuation-in-part of U.S. application Ser. No. 10/075,442, filed Feb. 15, 2002, now U.S. Pat. No. 6,855,732 issued on Feb. 15, 2005, which is a divisional of U.S. application Ser. No. 09/436,047 filed Nov. 8, 1999, now U.S. Pat. No. 6,525,093 issued on Feb. 25, 2003.

FIELD OF THE INVENTION

The invention is directed to compounds, for example, heterocyclic derivatives of acyl urea, thiourea, carbamate and thiocarbamate compounds, that provide a variety of useful pharmacological effects. The compounds are useful, for example, in lowering blood glucose levels in hyperglycemic disorders, such as diabetes mellitus, and for treating related disorders, such as obesity and hyperlipidemia. Furthermore, these compounds are useful for treatment of disorders associated with insulin resistance, such as polycystic ovary syndrome, and for the treatment of inflammation, inflammatory and immunological diseases, particularly those mediated by pro-inflammatory cytokines (such as TNF-alpha, IL-1 beta and IL-6), type 4 and type 3 phosphodiesterase (PDE4 and PDE3, respectively), p44/42 mitogen-activated protein (MAP) kinase, cyclooxygenase-2 (COX-2) and/or inducible nitric oxide synthase (iNOS).

BACKGROUND OF THE INVENTION

The causes of diabetes mellitus are not yet known, although both genetics and environment seem to be major factors. Type 1 diabetes, also known as insulin-dependent diabetes mellitus (IDDM), is an autoimmune disease in which the responsible autoantigen is still unidentified. Since their insulin-producing pancreatic cells are destroyed, Type 1 diabetics need to take insulin parenterally to survive. On the other hand, type 2 diabetes, also called non-insulin-dependent diabetes mellitus (NIDDM), the more common form, is a metabolic disorder resulting from the body's inability to make a sufficient amount of insulin or to properly use the insulin that is produced. Impaired insulin secretion and insulin resistance are considered the major defects; however, the precise genetic factors involved in the mechanism remain unknown.

Other than insulin administered parenterally and as shown in Table 1, there are generally four major classes of oral hypoglycemic agents currently used in the treatment of diabetes mellitus:

TABLE 1

| Class | Approved Drugs | Mechanisms of Action | Limitations |
| --- | --- | --- | --- |
| Sulfonylurea | four (1st generation) and two (2nd generation) | stimulates pancreas to release more insulin | hypoglycemia; may increase cardiovascular risk; contra-indicated in liver and renal dysfunction; hyperinsulinemia |
| Biguanide | metformin | reduces glucose production by liver; improves insulin sensitivity | lactic acidosis; GI side effects |
| Alpha-glucosidase inhibitor | acarbose | reduces glucose absorption by gut | GI side effects; requires frequent postprandial dosing |
| Thiazolidinedione | troglitazone (withdrawn) rosiglitazone pioglitazone | stimulates nuclear PPAR-gamma receptor; reduces insulin resistance | edema; contra-indicated in heart failure; long onset of action; weight gain; frequent liver function testing |

As is shown in the above table, each of the current agents available for use in treatment of diabetes mellitus has several disadvantages. Accordingly, there is a need for the identification and development of new agents, particularly, water soluble agents which can be orally administered, for use in the treatment of diabetes mellitus and other hyperglycemic disorders.

Moreover, while the thiazolidinedione class has gained more widespread use in recent years as insulin sensitizers to combat "insulin resistance", a condition in which the patient becomes less responsive to the effects of insulin, there is a need for frequent liver testing for patients using these compounds. In fact, the known thiazolidinediones are not effective for a significant portion of the patient population. In addition, the first drug in this class to be approved by the FDA, troglitazone, was withdrawn from the market due to problems of liver toxicity. Thus, there is a continuing need for nontoxic, more widely effective insulin sensitizers.

As indicated above, the invention is also directed to the treatment of immunological diseases or inflammation, in particular, such diseases as are mediated by cytokines, COX-2 and iNOS. The principal elements of the immune system are macrophages or antigen-presenting cells, T cells and B cells. Macrophages are important mediators of inflammation and also provide the necessary "help" for T cell stimulation and proliferation. For example, macrophages make the cytokines IL-1, IL-12 and TNF-alpha, all of which are potent pro-inflammatory molecules. Cytokine production may lead to the secretion of other cytokines, altered cellular function, cell division or differentiation. In addition, activation of macrophages results in the induction of enzymes, such as COX-2 and iNOS, and in the production of free radicals capable of damaging normal cells. Many factors activate macrophages, including bacterial products, superantigens and interferon gamma. It is believed that phosphotyrosine kinases and other cellular kinases are involved in the activation process. Since macrophages are sentinel to the development of an immune response, agents that modify their function, specifically their cytokine secretion profile, are likely to determine the direction and potency of the immune response.

Inflammation is the body's normal response to injury or infection. However, in inflammatory diseases such as rheumatoid arthritis, pathologic inflammatory processes can lead to morbidity and mortality. The cytokine tumor necrosis factor-alpha (TNF-alpha) plays a central role in the inflammatory response and has been targeted as a point of intervention in inflammatory disease. TNF-alpha is a polypeptide hormone released by activated macrophages and other cells. At low concentrations, TNF-alpha participates in the protective inflammatory response by activating leukocytes and promoting their migration to extravascular sites of inflammation (Moser et al., J Clin Invest, 83:444-55, 1989). At higher concentrations, TNF-alpha can act as a potent pyrogen and induce the production of other pro-inflammatory cytokines (Haworth et al., Eur J Immunol, 21:2575-79, 1991; Brennan et al., Lancet, 2:244-7, 1989). TNF-alpha also stimulates the synthesis of acute-phase proteins. In rheumatoid arthritis, a chronic and progressive inflammatory disease affecting about 1% of the adult U.S. population, TNF-alpha mediates the cytokine cascade that leads to joint damage and destruction (Arend et al., Arthritis Rheum, 38:151-60, 1995). Inhibitors of TNF-alpha, including soluble TNF receptors (etanercept) (Goldenberg, Clin Ther, 21:75-87, 1999) and anti-TNF-alpha antibody (infliximab) (Luong et al., Ann Pharmacother, 34:743-60, 2000), the contents of each of which are incorporated herein by reference, have recently been approved by the U.S. Food and Drug Administration (FDA) as agents for the treatment of rheumatoid arthritis.

Elevated levels of TNF-alpha have also been implicated in many other disorders and disease conditions, including cachexia (Fong et al., Am J Physiol, 256:R659-65, 1989), septic shock syndrome (Tracey et al., Proc Soc Exp Biol Med, 200:233-9, 1992), osteoarthritis (Venn et al., Arthritis Rheum, 36:819-26, 1993), inflammatory bowel disease such as Crohn's disease and ulcerative colitis (Murch et al., Gut, 32:913-7, 1991), Behcet's disease (Akoglu et al., J Rheumatol, 17:1107-8, 1990), Kawasaki disease (Matsubara et al., Clin Immunol Immunopathol, 56:29-36, 1990), cerebral malaria (Grau et al., N Engl J Med, 320:1586-91, 1989), adult respiratory distress syndrome (Millar et al., Lancet 2:712-4, 1989), asbestosis and silicosis (Bissonnette et al., Inflammation, 13:329-39, 1989), pulmonary sarcoidosis (Baughman et al., J Lab Clin Med, 115:36-42, 1990), asthma (Shah et al., Clin Exp Allergy, 25:1038-44, 1995), AIDS (Dezube et al., J Acquir Immune Defic Syndr, 5:1099-104, 1992), meningitis (Waage et al., Lancet, 1:355-7, 1987), psoriasis (Oh et al., J Am Acad Dermatol, 42:829-30, 2000), spondyloarthritides such as ankylosing spondylitis (Braun et al., Curr Opin Rheumatol 13:245-9, 2001; Marzo-Ortega et al., Arthritis Rheum 44:2112-7, 2001), graft versus host reaction (Nestel et al., J Exp Med, 175:405-13, 1992), multiple sclerosis (Sharief et al., N Engl J Med, 325:467-72, 1991), systemic lupus erythematosus (Maury et al., Int J Tissue React, 11:189-93, 1989), diabetes (Hotamisligil et al., Science, 259:87-91, 1993) and atherosclerosis (Bruunsgaard et al., Clin Exp Immunol, 121:255-60, 2000), the contents of each of which are incorporated herein by reference. It can be seen from the references cited above that inhibitors of TNF-alpha are potentially useful in the treatment of a wide variety of diseases.

Interleukin-6 (IL-6) is another pro-inflammatory cytokine that exhibits pleiotropy and redundancy of action. IL-6 participates in the immune response, inflammation and hematopoiesis. It is a potent inducer of the hepatic acute phase response and is a powerful stimulator of the hypothalamic-pituitary-adrenal axis that is under negative control by glucocorticoids. IL-6 promotes the secretion of growth hormone but inhibits release of thyroid stimulating hormone. Elevated levels of IL-6 are seen in several inflammatory diseases, and inhibition of the IL-6 cytokine subfamily has been suggested as a strategy to improve therapy for rheumatoid arthritis (Carroll et al., Inflamm Res, 47:1-7, 1998). In addition, IL-6 has been implicated in the progression of atherosclerosis and the pathogenesis of coronary heart disease (Yudkin et al., Atherosclerosis, 148:209-14, 1999). Overproduction of IL-6 is also seen in steroid withdrawal syndrome, conditions related to deregulated vasopressin secretion, and osteoporosis associated with increased bone resorption, such as in cases of hyperparathyroidism and sex-steroid deficiency (Papanicolaou et al., Ann Intern Med, 128:127-37, 1998). Since excessive production of IL-6 is implicated in several disease states, it is highly desirable to develop compounds that inhibit IL-6 secretion.

The cytokine IL-1 beta also participates in the inflammatory response. It stimulates thymocyte proliferation, fibroblast growth factor activity, and the release of prostaglandin from synovial cells. Elevated or unregulated levels of the cytokine IL-1 beta have been associated with a number of inflammatory diseases and other disease states, including but not limited to adult respiratory distress syndrome (Meduri et al, Chest 107:1062-73, 1995), allergy (Hastie et al, Cytokine 8:730-8, 1996), Alzheimer's disease (O'Barr et al, J Neuroimmunol 109:87-94, 2000), anorexia (Laye et al, Am J Physiol Regul Integr Comp Physiol 279:R93-8, 2000), asthma (Sousa et al, Thorax 52:407-10, 1997), atherosclerosis (Dewberry et al, Arterioscler Thromb Vasc Biol 20:2394-400, 2000), brain tumors (Ilyin et al, Mol Chem Neuropathol 33:125-37, 1998), cachexia (Nakatani et al, Res Commun Mol Pathol Pharmacol 102:241-9, 1998), carcinoma (Ikemoto et al, Anticancer Res 20:317-21, 2000), chronic arthritis (van den Berg et al, Clin Exp Rheumatol 17:S105-14, 1999), chronic fatigue syndrome (Cannon et al, J Clin Immunol 17:253-61, 1997), CNS trauma (Herx et al, J Immunol 165:2232-9, 2000), epilepsy (De Simoni et al, Eur J Neurosci 12:2623-33, 2000), fibrotic lung diseases (Pan et al, Pathol Int 46:91-9, 1996), fulminant hepatic failure (Sekiyama et al, Clin Exp Immunol 98:71-7, 1994), gingivitis (Biesbrock et al, Monogr Oral Sci 17:20-31, 2000), glomerulonephritis (Kluth et al, J Nephrol 12:66-75, 1999), Guillain-Barre syndrome (Zhu et al, Clin Immunol Immunopathol 84:85-94, 1997), heat hyperalgesia (Opree et al, J Neurosci 20:6289-93, 2000), hemorrhage and endotoxemia (Parsey et al, J Immunol 160:1007-13, 1998), inflammatory bowel disease (Olson et al, J Pediatr Gastroenterol Nutr 16:241-6, 1993), leukemia (Estrov et al, Leuk Lymphoma 24:379-91, 1997), leukemic arthritis (Rudwaleit et al, Arthritis Rheum 41:1695-700, 1998), systemic lupus erythematosus (Mao et al, Autoimmunity 24:71-9, 1996), multiple sclerosis (Martin et al, J Neuroimmunol 61:241-5, 1995), osteoarthritis (Hernvann et al, Osteoarthritis Cartilage 4:139-42, 1996), osteoporosis (Zheng et al, Maturitas 26:63-71, 1997), Parkinson's disease (Bessler et al, Biomed Pharmacother 53:141-5, 1999), POEMS syndrome (Gherardi et al, Blood 83:2587-93, 1994), pre-term labor (Dudley, J Reprod Immunol 36:93-109, 1997), psoriasis (Bonifati et al, J Biol Regul Homeost Agents 11:133-6, 1997), reperfusion injury (Clark et al, J Surg Res 58:675-81, 1995), rheumatoid arthritis (Seitz et al, J Rheumatol 23:1512-6, 1996), septic shock (van Deuren et al, Blood 90:1101-8, 1997), systemic vasculitis (Brooks et al, Clin Exp Immunol 106:273-9, 1996), temporal mandibular joint disease (Nordahl et al, Eur J Oral Sci 106:559-63, 1998), tuberculosis (Tsao et al, Tuber Lung Dis 79:279-85, 1999), viral rhinitis (Roseler et al, Eur Arch Otorhinolaryngol Suppl 1:S61-3, 1995), the contents of each of which are incorporated herein by reference, and pain and/or inflammation resulting from strain, sprain, trauma, surgery, infection or other disease processes. Since overproduction of IL-1 beta is associated with numerous disease conditions, it is desirable to develop compounds that inhibit the production or activity of IL-1 beta.

Cyclooxygenase is an enzyme that catalyzes a rate-determining step in the biosynthesis of prostaglandins, which are important mediators of inflammation and pain. The enzyme occurs as at least two distinct isomers, cyclooxygenase-1 (COX-1) and cyclooxygenase-2 (COX-2). The COX-1 isomer is constitutively expressed in the gastric mucosa, platelets and other cells and is involved in the maintenance of homeostasis in mammals, including protecting the integrity of the digestive tract. The COX-2 isomer, on the other hand, is not constitutively expressed but rather is induced by various agents, such as cytokines, mitogens, hormones and growth factors. In particular, COX-2 is induced during the inflammatory response (DeWitt DL, Biochim Biophys Acta, 1083:121-34, 1991; Seibert et al., Receptor, 4:17-23, 1994.). Aspirin and other conventional non-steroid anti-inflammatory drugs (NSAIDs) are non-selective inhibitors of both COX-1 and COX-2. They can be effective in reducing inflammatory pain and swelling, but since they hamper the protective action of COX-1, they produce undesirable side effects of gastrointestinal pathology. Therefore, agents that selectively inhibit COX-2 but not COX-1 are preferable for treatment of inflammatory diseases. Recently, a diarylpyrazole sulfonamide (celecoxib) that selectively inhibits COX-2 has been approved by the FDA for use in the treatment of osteoarthritis and adult rheumatoid arthritis (Luong et al., Ann Pharmacother, 34:743-60, 2000; Penning et al., J Med Chem, 40:1347-65, 1997). Another selective COX-2 inhibitor, rofecoxib, has been approved by the FDA for treatment of osteoarthritis, acute pain and primary dysmenorrhea (Scott and Lamb, Drugs, 58:499-505, 1999; Morrison et al., Obstet Gynecol, 94:504-8, 1999; Saag et al, Arch Fam Med, 9:1124-34, 2000). COX-2 is also expressed in many cancers and precancerous lesions, and there is mounting evidence that selective COX-2 inhibitors may be useful for treating and preventing colorectal, breast and other cancers (Taketo M M, J Natl Cancer Inst, 90:1609-20, 1998; Fournier et al., J Cell Biochem Suppl, 34:97-102, 2000; Masferrer et al., Cancer Res, 60:1306-11, 2000), the contents of each of which are incorporated herein by reference. In 1999 celecoxib was approved by the FDA as an adjunct to usual care for patients with familial adenomatous polyposis, a condition which, left untreated, generally leads to colorectal cancer.

Production of nitric oxide by iNOS has been associated with both beneficial and detrimental effects in inflammation, inflammatory diseases and related disorders. For example, deleterious effects have been implicated in the pathogenesis of abdominal aortic aneurysms (Johanning et al, J Vasc Surg 33:579-86, 2001), acute endotoxemia (Henningsson et al, Am J Physiol Cell Physiol 280:C1242-54, 2001), amyotrophic lateral sclerosis (Sasaki et al, Neurosci Lett 291:44-8, 2000), atherosclerosis (Behr-Roussel et al, Circulation 102:1033-8, 2000), bladder cancer (Wolf et al, Virchows Arch 437:662-6, 2000), colon cancer (Watanabe et al, Biofactors 12:129-33, 2000), cystitis (Alfieri et al, Naunyn Schmiedebergs Arch Pharmacol 363:353-7, 2001), HIV-1 encephalitis (Zhao et al, J Neuroimmunol 115:182-91, 2001), inflammatory bowel disease (Singer et al, Gastroenterology 111:871-85, 1996), multiple sclerosis (Pozza et al, Brain Res 855:39-46, 2000), osteoarthritis (Pelletier et al, Osteoarthritis Cartilage 7:416-8, 1999), osteoporosis (Armour et al, J Bone Miner Res 14:2137-42, 1999), portal hypertension (Schroeder et al, Dig Dis Sci Dec 45:2405-10, 2000), pulmonary edema in endotoxin shock (Lee et al, Clin Exp Pharmacol Physiol 28:315-20, 2001), rheumatoid arthritis (van't Hof et al, Rheumatology (Oxford) 39:1004-8, 2000), sepsis (Nishina et al, Anesth Analg 92:959-66, 2001), severe burn/smoke inhalation injury (Soejima et al, Am J Respir Crit Care Med 163:745-52, 2001), and ulcerative colitis (Ikeda et al, Am J Gastroenterol 92:1339-41, 1997), the contents of each of which are incorporated herein by reference. Since the production of nitric oxide by iNOS has been implicated in the pathogenesis of inflammatory and related immunological diseases, it is desirable to develop compounds that inhibit iNOS activity or expression.

Phosphodiesterases (PDEs) are responsible for the hydrolysis of intracellular cyclic adenosine and guanosine monophosphate (cAMP and cGMP), which converts these second messengers into their inactive forms. There are 11 major families of PDEs, designated PDE1 to PDE11. Type 4 phosphodiesterase (PDE4) is found in airway smooth muscle cells and in immune and inflammatory cells. PDE4 activity has been associated with a wide variety of inflammatory and autoimmune diseases, and PDE4 inhibitors have been studied as potential therapeutic agents for such diseases as asthma, chronic obstructive pulmonary disease, rheumatoid arthritis, multiple sclerosis and type 2 diabetes (Burnouf and Pruniaux, Current Pharm Des, 8:1255-96, 2002; Dal Piaz and Giovannoni, Eur J Med Chem, 35:463-80, 2000). Type 3 phosphodiesterase (PDE3) is localized in platelets and cardiac and vascular smooth muscle cells. Inhibitors of PDE3 have been proposed as possible drugs for the treatment of acute respiratory distress syndrome (Schermuly et al, J Pharmacol Exp Ther, 292:512-20, 2000), cancer (Shimizu et al, Anticancer Drugs, 13:875-80, 2002; Murata et al, Anticancer Drugs, 12:79-83, 2001), cardiomyopathy (Alharethi and Movsesian, Expert Opin Investig Drugs, 11:1529-36, 2002), congestive heart failure (Movsesian, J Am Coll Cardiol, 34:318-24, 1999), erectile dysfunction (Kuthe et al, Curr Opin Investig Drugs, 3:1489-95, 2002), and T-cell-mediated autoimmune disorders (Bielekova et al, J Immunol 164:1117-24, 2000), the contents of each of which are incorporated herein by reference.

Activation of lymphocyte and macrophage immune response to pathogens involve complex intracellular signaling pathways involving a cascade of various phosphorylating enzymes, kinases that ultimately regulate cytokine production and cell apoptosis. Key kinases include p44/42 MAP kinase (also known as ERK1/ERK2), P38 MAP kinase, MEK, and IRAK/NFkB. While different processes utilize different aspects of the pathway, the bacterial coat-derived protein LPS has been shown to activate multiple mitogen-activated protein kinases, including the extracellular signal-regulated receptor kinases ERK1 and ERK2. LPS-induced TNF-alpha production by human monocytes involves activation of ERK1/ERK2 (van der Bruggen et al, Infect Immun, 67:3824-9, 1999). As TNF-alpha is a key mediator of autoimmune disease, blocking the ERK pathway has potential for the treatment of inflammatory and immunological diseases such as lupus (Yi et al, J Immunol, 165: 6627-34, 2000), rheumatoid arthritis (Neff et al, Cell Microbiol, 3:703-12, 2001; Schett et al, Arthritis Rheum, 43:2501-12, 2000), psoriasis (van der Bruggen et al, Infect Immun, 67:3824-9, 1999) and destruction of pancreatic islet beta cells in Type I diabetes (Pavlovic et al, Eur Cytokine Netw 11:267-74, 2000), the contents of each of which are incorporated herein by reference.

It will be appreciated from the foregoing that, while there have been extensive prior efforts to provide compounds for inhibiting, for example, TNF-alpha, IL-1 beta, IL-6, COX-2, PDE4 or other agents considered responsible for inflammation or inflammatory diseases, e.g. arthritis, there still remains a need for new and improved compounds for effectively treating or inhibiting such diseases. A principal object of the invention is to provide compounds which are effective for such treatments as well as for the treatment of, for example, diabetes, coronary heart disease, insulin resistance and related disorders.

SUMMARY OF THE INVENTION

The invention is directed to compounds, for example, heterocyclic derivatives of acyl urea, thiourea, carbamate and thiocarbamate compounds, for providing a variety of useful pharmacological effects. The compounds are useful, for example, in lowering blood glucose levels in hyperglycemic disorders, such as diabetes mellitus, and for treating related disorders, such as obesity and hyperlipidemia. Furthermore, these compounds are useful for treatment of disorders associated with insulin resistance, such as polycystic ovary syndrome, and for the treatment of inflammation and immunological diseases, particularly those mediated by pro-inflammatory cytokines (such as TNF-alpha, IL-1 beta and IL-6), type 4 phosphodiesterase (PDE4), type 3 phosphodiesterase (PDE3), p44/42 mitogen activated protein (MAP) kinase, cyclooxygenase-2 (COX-2) and/or inducible nitric oxide synthase (iNOS). In particular, the invention provides compounds represented by the following Formulas I-XIII as well as the pharmaceutically acceptable salts, hydrates or solvates thereof:

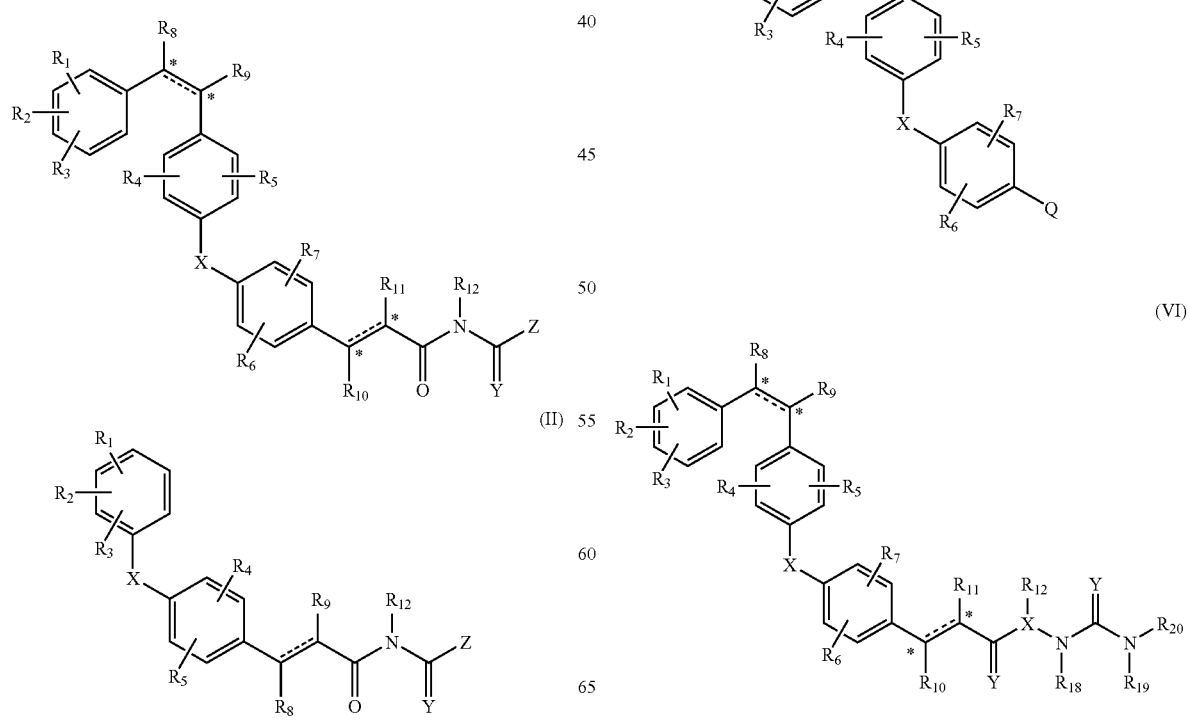

-continued

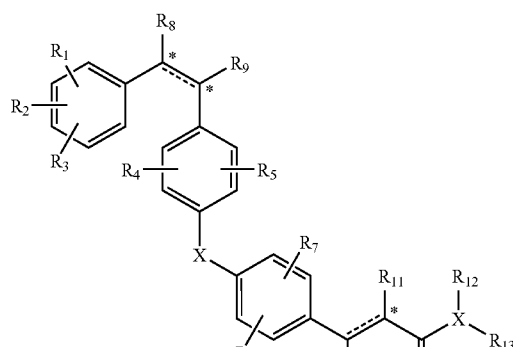
(VII)

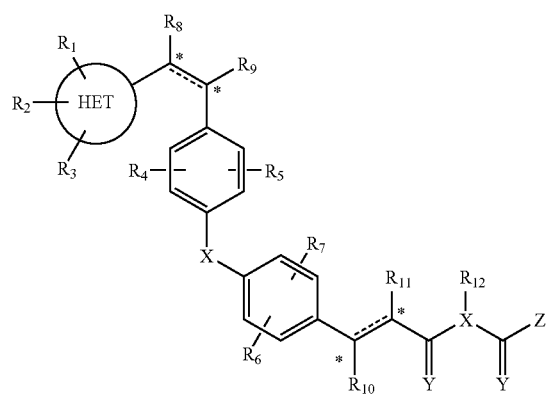
(VIII)

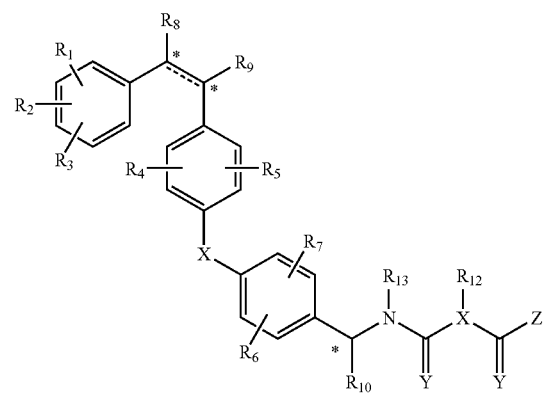
(IX)

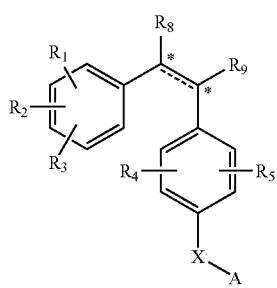
(X)

-continued

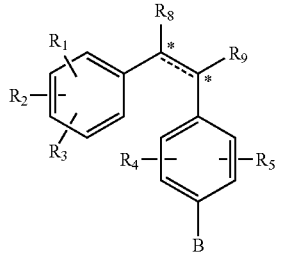
(XI)

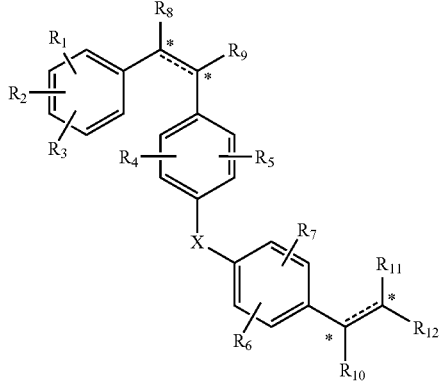
(XII)

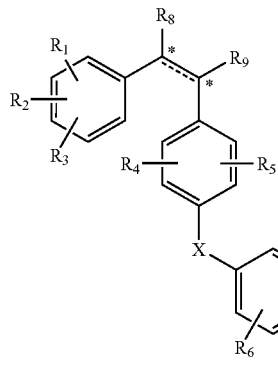
(XIII)

wherein the stereocenters marked with an asterisk (*) may be R— or S—; the bond represented by a dashed line plus a solid line may be a double bond or a single bond, and when the bond is a double bond it may be in the E or Z configuration, and when the bond is a single bond the resulting stereocenters may have the R— or S— configuration; and $R_1$, $R_2$, $R_3$, $P_4$, $R_5$, $R_6$ and $R_7$ are each independently selected from the group consisting of H; optionally substituted $C_1$-$C_{20}$ linear or branched alkyl including chloroalkyl or fluoroalkyl; optionally substituted $C_2$-$C_{20}$ linear or branched alkenyl; optionally substituted $C_6$-$C_{20}$ aryl, linear or branched alkylaryl, linear or branched alkenylaryl; COOR where R is H, optionally substituted $C_1$-$C_{20}$ alkyl, optionally substituted $C_2$-$C_{20}$ alkenyl or optionally substituted $C_6$-$C_{10}$ aryl, sodium, potassium or other pharmaceutically acceptable counter-ion such as calcium, magnesium, ammonium, tromethamine and the like; CONR'R", where R' and R" are independently H, optionally substituted $C_1$-$C_{20}$ alkyl, optionally substituted $C_2$-$C_{20}$ alkenyl or optionally substituted $C_6$-$C_{10}$ aryl or where NR'R" represents a cyclic moiety such as morpholine, piperidine, piperazine and the like; optionally substituted $C_1$-$C_6$ amidoalkyl; $NH_2$; $C_1$-$C_{20}$ alkylamino, bis (alkylamino), cycloalkylamino or cyclic amino; OH; optionally substituted $C_1$-$C_{20}$ alkoxy including trifluoromethoxy and the like; optionally substituted $C_1$-$C_{20}$ alkanoyl; optionally substituted $C_1$-$C_{20}$ acyloxy; halo; optionally substituted $C_1$-$C_{20}$ alkylcarboxylamino; cyano; nitro; $SO_2NR'''R''''$ where R''' and R'''' are independently H, $C_1$-$C_{20}$ alkyl or aryl; $SO_2R'''$ where R''' is H, $C_1$-$C_{20}$ alkyl or aryl; $SO_3R'''$ where R''' is H, $C_1$-$C_{20}$ alkyl or aryl; and $C_4$-$C_8$ heterocycles such as tetrazolyl, imidazolyl, pyrrolyl, pyridyl, indolyl and the like; and wherein when individual aromatic rings possess adjacent substituents, these substituents may be joined to form a ring such as a methylenedioxy or ethylenedioxy group, and the like, including lactones and lactams;

$R_8$ and $R_9$ are each independently selected from the group consisting of H; optionally substituted $C_1$-$C_{20}$ linear or branched alkyl; optionally substituted $C_2$-$C_{20}$ linear or branched alkenyl; optionally substituted $C_6$-$C_{10}$ aryl or heteroaryl; COOR where R is H, optionally substituted $C_1$-$C_{20}$ alkyl, optionally substituted $C_2$-$C_{20}$ alkenyl or optionally substituted $C_6$-$C_{10}$ aryl, sodium, potassium or other pharmaceutically acceptable counter-ion such as calcium, magnesium, ammonium, tromethamine and the like; CONR'R", where R' and R" are independently H, alkoxy, optionally substituted $C_1$-$C_{20}$ alkyl, optionally substituted $C_2$-$C_{20}$ alkenyl, optionally substituted $C_3$-$C_{10}$ cycloalkyl or cycloalkenyl or optionally substituted $C_6$-$C_{10}$ aryl or heteroaryl, preferably 2-, 3- or 4-pyridyl; or where NR'R" represents a cyclic moiety such as morpholine, piperidine, hydroxypiperidine, imidazole, piperazine, methylpiperazine and the like; $NH_2$; $C_1$-$C_{20}$ alkylamino, bis(alkylamino), cycloalkylamino or cyclic amino; OH; $C_1$-$C_{20}$ alkoxy; $C_1$-$C_{20}$ alkanoyl; $C_1$-$C_{20}$ acyloxy; halo; $C_1$-$C_{20}$ alkylcarboxylamino; cyano; nitro; $SO_2NR'''R''''$ where R''' and R'''' are independently H, $C_1$-$C_{20}$ alkyl or aryl; $SO_2R'''$ where R''' is H, $C_1$-$C_{20}$ alkyl or aryl; $SO_3R'''$ where R''' is H, $C_1$-$C_{20}$ alkyl or aryl; and tetrazolyl; and wherein $R_8$ and $R_9$ together may be joined to form a $C_4$-$C_8$ heterocyclic ring, including lactone or lactam;

$R_{10}$ and $R_{11}$ are each independently selected from the group consisting of H; optionally substituted $C_1$-$C_{20}$ linear or branched alkyl; optionally substituted $C_2$-$C_{20}$ linear or branched alkenyl; optionally substituted $C_6$-$C_{10}$ aryl or heteroaryl; COOR where R is H, optionally substituted $C_1$-$C_{20}$ alkyl, optionally substituted $C_2$-$C_{20}$ alkenyl or optionally substituted $C_6$-$C_{10}$ aryl, sodium, potassium or other pharmaceutically acceptable counter-ion such as calcium, magnesium, ammonium, tromethamine and the like; CONR'R", where R' and R" are independently H, optionally substituted $C_1$-$C_{20}$ alkyl, optionally substituted $C_2$-$C_{20}$ alkenyl or optionally substituted $C_6$-Cio aryl or where NR'R" represents a cyclic moiety such as morpholine, piperidine, piperazine and the like; $NH_2$; $C_1$-$C_{20}$ alkylamino, bis(alkylamino), cycloalkylamino or cyclic amino; OH; $C_1$-$C_{20}$ alkoxy; $C_1$-$C_{20}$ alkanoyl; $C_1$-$C_{20}$ acyloxy; halo; $C_1$-$C_{20}$ alkylcarboxylamino; cyano; nitro; $SO_2NR'''RT''''$ where R''' and R'''' are independently H, $C_1$-$C_{20}$ alkyl or aryl; $SO_2R'''$ where R''' is H, $C_1$-$C_{20}$ alkyl or aryl; $SO_3R'''$ where R''' is H, $C_1$-$C_{20}$ alkyl or aryl; and tetrazolyl; and wherein $R_{10}$ and $R_{11}$ together may be joined to form a $C_4$-$C_8$ heterocyclic ring, including lactone or lactam;

$R_{12}$, $R_{13}$, $R_{18}$, $R_{19}$ and $R_{20}$ are each independently selected from the group consisting of
H; optionally substituted $C_1$-$C_{20}$ linear or branched alkyl; optionally substituted $C_2$-$C_{20}$ linear or branched alkenyl; optionally substituted $C_6$-$C_{10}$ aryl or heteroaryl; COOR where R is optionally substituted $C_1$-$C_{20}$ alkyl, optionally substituted $C_2$-$C_{20}$ alkenyl or optionally substituted $C_6$-$C_{10}$ aryl, sodium, potassium or other pharmaceutically acceptable counter-ion such as calcium, magnesium, ammonium, tromethamine and the like; CONR'R", where R' and R" are independently H, optionally substituted $C_1$-$C_{20}$ alkyl, optionally substituted $C_2$-$C_{20}$ alkenyl or optionally substituted $C_6$-$C_{10}$ aryl or where NR'R" represents a cyclic moiety such as morpholine, piperidine, piperazine and the like; $C_1$-$C_{20}$ alkanoyl; $C_1$-$C_{20}$ alkylamido; $C_6$-$C_{20}$ aroyl or heteroaroyl; $SO_2R'''$ where R''' is H, $C_1$-$C_{20}$ alkyl or aryl; morpholinocarbonylmethyl; piperazinocabonylmethyl; and piperadinocabonylmethyl;

$R_{12}$ and $R_{13}$ may be absent, or $R_{12}$ and $R_{13}$ together may be an optionally substituted heterocyclic ring, preferably morpholine, piperidine, piperazine, and N-methyl piperidine;

$R_{14}$ is selected from the group consisting of
H; optionally substituted $C_1$-$C_{20}$ linear or branched alkyl including chloroalkyl and fluoroalkyl; optionally substituted $C_2$-$C_{20}$ linear or branched alkenyl; optionally substituted $C_6$-$C_{10}$ aryl or heteroaryl; COOR where R is H, optionally substituted $C_1$-$C_{20}$ alkyl, optionally substituted $C_2$-$C_{20}$ alkenyl or optionally substituted $C_6$-$C_{10}$ aryl, sodium, potassium or other pharmaceutically acceptable counter-ion such as calcium, magnesium, ammonium, tromethamine and the like; CONR'R", where R' and R" are independently H, optionally substituted $C_1$-$C_{20}$ alkyl, optionally substituted $C_2$-$C_{20}$ alkenyl or optionally substituted $C_6$-$C_{10}$ aryl or where NR'R" represents a cyclic moiety such as morpholine, piperidine, piperazine and the like; cyano; and tetrazolyl;

$R_{15}$, $R_{16}$, and $R_{17}$ are each independently selected from the group consisting of
H; optionally substituted $C_1$-$C_{20}$ linear or branched alkyl including chloroalkyl and fluoroalkyl; optionally substituted $C_2$-$C_{20}$ linear or branched alkenyl; optionally substituted $C_6$-$C_{10}$ aryl or heteroaryl; COOR where R is H, optionally substituted $C_1$-$C_{20}$ alkyl, optionally substituted $C_2$-$C_{20}$ alkenyl or optionally substituted $C_6$-$C_{10}$ aryl, sodium, potassium or other pharmaceutically acceptable counter-ion such as calcium, magnesium, ammonium, tromethamine and the like; CONR'R", where R' and R" are independently H, optionally substituted $C_1$-$C_{20}$ alkyl, optionally substituted $C_2$-$C_{20}$ alkenyl or optionally substituted $C_6$-$C_{10}$ aryl or where NR'R" represents a cyclic moiety such as morpholine, piperidine, piperazine and the like; $NH_2$; $C_1$-$C_{20}$ alkylamino, bis(alkylamino), cycloalkylamino or cyclic amino; OH; $C_1$-$C_{20}$ alkoxy; $C_1$-$C_{20}$ alkanoyl; $C_1$-$C_{20}$ acyloxy; halo; $C_1$-$C_{20}$ alkylcarboxylamino; cyano; nitro; $SO_2NR'''R''''$ where R''' and R'''' are independently H, $C_1$-$C_{20}$ alkyl or aryl; $SO_2R'''$ where R''' is H, $C_1$-$C_{20}$ alkyl or aryl; $SO_3R'''$ where R''' is H, $C_1$-$C_{20}$ alkyl or aryl; and tetrazolyl;

X is independently selected from the group consisting of O; N; S; S=O; $SO_2$; or NR'''', where R'''' may be H or optionally substituted $C_1$-$C_{20}$ alkyl, optionally substituted $C_2$-$C_{20}$ alkenyl, optionally substituted $C_1$-$C_{20}$ acyl, optionally substituted $C_1$-$C_{20}$ acyloxy and optionally substituted $C_1$-$C_{20}$ alkoxycarbonyl;

Y is independently O, S or NH;

Z is $OR_a$ where $R_a$ is selected from the group consisting of

H; optionally substituted $C_1$-$C_{20}$ linear or branched alkyl including chloroalkyl or fluoroalkyl and the like; optionally substituted $C_2$-$C_{20}$ linear or branched alkenyl; optionally substituted $C_6$-$C_{10}$ aryl or heteroaryl; optionally substituted $C_6$-$C_{20}$ aroyl or heteroaroyl; optionally substituted $C_1$-$C_{20}$ alkanoyl; and $SO_2R'''$ where $R'''$ is H, $C_1$-$C_{20}$ alkyl or aryl; or Z is $NR_bR_c$ where $R_b$ and $R_c$ are independently selected from the group consisting of H; optionally substituted $C_1$-$C_{20}$ linear or branched alkyl including chloroalkyl or fluoroalkyl and the like; optionally substituted $C_2$-$C_{20}$ linear or branched alkenyl; optionally substituted $C_6$-$C_{10}$ aryl or heteroaryl; optionally substituted $C_3$-$C_{10}$ cycloalkyl or cycloalkenyl; $COOZ_1$ where $Z_1$ is optionally substituted $C_1$-$C_{20}$ alkyl, optionally substituted $C_2$-$C_{20}$ alkenyl or optionally substituted $C_6$-$C_{10}$ aryl; optionally substituted $C_6$-$C_{20}$ aroyl or heteroaroyl; optionally substituted $C_1$-$C_{20}$ alkanoyl; and $SO_2R'''$ where $R'''$ is H, $C_1$-$C_{20}$ alkyl or aryl; and wherein $R_b$ and $R_c$ together may be joined to form a 3-6 membered ring such as aziridine, morpholine, piperidine, piperazine and the like; or Z is $CR_dR_eR_f$ where $R_d$, $R_e$ and $R_f$ are each independently selected from the group consisting of H; optionally substituted $C_1$-$C_{20}$ linear or branched alkyl including chloroalkyl or fluoroalkyl and the like; optionally substituted $C_2$-$C_{20}$ linear or branched alkenyl; optionally substituted $C_6$-$C_{10}$ aryl or heteroaryl; optionally substituted $C_3$-$C_{10}$ cycloalkyl or cycloalkenyl; COOR where R is H, optionally substituted $C_1$-$C_{20}$ alkyl, optionally substituted $C_2$-$C_{20}$ alkenyl or optionally substituted $C_6$-$C_{10}$ aryl, sodium, potassium or other pharmaceutically acceptable counter-ion such as calcium, magnesium, ammonium, tromethamine and the like; $NH_2$; $C_1$-$C_{20}$ alkylamino, bis(alkylamino); cycloalkylamino or cyclic amino; OH; optionally substituted $C_1$-$C_{20}$ alkoxy including trifluoromethoxy and the like; optionally substituted $C_1$-$C_{20}$ alkanoyl; optionally substituted $C_1$-$C_{20}$ acyloxy; optionally substituted $C_6$-$C_{20}$ aroyl or heteroaroyl; halo; cyano; nitro; optionally substituted $C_1$-$C_{20}$ alkylcarboxylamino; $SO_2NR'''R''''$ where $R'''$ and $R''''$ are independently H, $C_1$-$C_{20}$ alkyl or aryl; $SO_2R'''$ where $R'''$ is H, $C_1$-$C_{20}$ alkyl or aryl; and $SO_3R'''$ where $R'''$ is H, $C_1$-$C_{20}$ alkyl or aryl; and wherein $R_d$ and $R_e$ together may be joined to form a 3-6 membered ring such as aziridine, morpholine, piperidine, piperazine and the like; and the resulting stereocenter may have the R— or S— configuration; or the grouping C(=Y)Z may represent hydrogen or $R_{12}$ or may be absent.

Q is $OR_a$ where $R_a$ is selected from the group consisting of

H; optionally substituted $C_1$-$C_{20}$ linear or branched alkyl including chloroalkyl or fluoroalkyl and the like; optionally substituted $C_2$-$C_{20}$ linear or branched alkenyl; optionally substituted $C_6$-$C_{10}$ aryl or heteroaryl; optionally substituted $C_6$-$C_{20}$ aroyl or heteroaroyl; optionally substituted $C_1$-$C_{20}$ alkanoyl; and $SO_2R'''$ where $R'''$ is H, $C_1$-$C_{20}$ alkyl or aryl; or Q is $NR_bR_c$ where $R_b$ and $R_c$ are independently selected from the group consisting of H; optionally substituted $C_1$-$C_{20}$ linear or branched alkyl including chloroalkyl or fluoroalkyl and the like; optionally substituted $C_2$-$C_{20}$ linear or branched alkenyl; optionally substituted $C_6$-$C_{10}$ aryl or heteroaryl; optionally substituted $C_3$-$C_{10}$ cycloalkyl or cycloalkenyl; $COOZ_1$ where $Z_1$ is optionally substituted $C_1$-$C_{20}$ alkyl, optionally substituted $C_2$-$C_{20}$ alkenyl or optionally substituted $C_6$-$C_{10}$ aryl; optionally substituted $C_6$-$C_{20}$ aroyl or heteroaroyl; optionally substituted $C_1$-$C_{20}$ alkanoyl; and $SO_2R'''$ where $R'''$ is H, $C_1$-$C_{20}$ alkyl or aryl; and wherein $R_b$ and $R_c$ together may be joined to form a 3-6 membered ring such as aziridine, morpholine, piperidine, piperazine and the like; or Q is $SR_g$, $SOR_g$ or $SO_2R_g$ where $R_g$ is selected from the group consisting of H; optionally substituted $C_1$-$C_{20}$ linear or branched alkyl including chloroalkyl or floroalkyl and the like; optionally substituted $C_2$-$C_{20}$ linear or branched alkenyl; optionally substituted $C_1$-$C_{20}$ acyl; optionally substituted $C_1$-$C_{20}$ alkoxycarbonyl; $C_2$-$C_{20}$ alkoxy; optionally substituted $C_6$-$C_{10}$ aryl or heteroaryl; and optionally substituted $C_6$-$C_{10}$ aroyl or heteroaroyl.

Group A is optionally substituted $C_2$-$C_{20}$ linear or branched alkenyl; optionally substituted $C_6$-$C_{20}$ aryl, linear or branched alkylaryl, linear or branched alkenylaryl; optionally substituted heteroaryls like pyridine, indole, morpholine, piperidine, piperazine, tetrazolyl and the like; $COR_h$ where $R_h$ is optionally substituted $C_1$-$C_{20}$ linear or branched alkyl; optionally substituted $C_2$-$C_{20}$ linear or branched alkenyl; optionally substituted $C_6$-$C_{20}$ aryl, linear or branched alkylaryl, linear or branched alkenylaryl; optionally substituted heteroaryls like pyridine, indole, morpholine, piperidine, piperazine, tetrazolyl and the like;

Group B is OH, $C_1$-$C_{20}$ alkoxy; $SO_2R_i$ where $R_i$ may be H or linear or branched $C_1$-$C_{20}$ alkyl.

Group Het (depicted in Formula VIII as "HET" enclosed by a circle) represents a heterocyclic ring which is pyridyl, indolyl, tetrazolyl, imidazolyl, morphonyl, piperidinyl, piperazinyl, thiophenyl or the like.

These compounds are useful for treating diabetes and other diseases linked to insulin resistance, such as coronary artery disease and peripheral vascular disease, and also for treating or inhibiting inflammation or inflammatory diseases such as inflammatory arthritides and collagen vascular diseases, which are caused by, for example, cytokines or inducible enzymes such as TNF-alpha, IL-1, IL-6, iNOS and/or COX-2. The compounds are also useful for treating or preventing other diseases mediated by cytokines, iNOS and/or COX-2, such as cancer.

Another aspect of the invention is a method of treating diabetes and related diseases comprising the step of administering to a subject suffering from a diabetic or related condition a therapeutically effective amount of a compound of Formulas I-XIII. Additionally, the invention provides a method of treating inflammation or inflammatory diseases or diseases mediated by cytokines, iNOS, PDE4, PDE3, p44/42 MAP kinase and/or COX-2 by administering to a subject in need of such treatment an effective amount of a compound according to Formulas I-XIII. Further, pharmaceutical compositions containing a therapeutically effective amount of one or more compounds according to Formulas I-XIII together with a pharmaceutically or physiologically acceptable co-agents, excipients, synergists, carriers and the like, for use in the treatments contemplated herein, are also provided.

BRIEF DESCRIPTION OF THE DRAWINGS

FIG. 1 shows a graph of the dose-dependent increase in glucose uptake in 3T3-L1 adipocytes treated with varying concentrations of a compound according to the invention.

FIG. 2 shows a graph of the enhancement of glucose uptake in 3T3-L1 adipocytes treated with a compound according to the invention in addition to varying concentrations of insulin.

FIG. 3 shows a graph of the lowering of blood glucose levels in ob/ob mice treated with a compound according to the invention.

FIGS. 4A and 4B show graphs of the lowering of serum triglycerides and free fatty acid levels, respectively, in ob/ob mice treated with a compound according to the invention.

FIG. 5 shows a graph of the inhibition of LPS-induced TNF-alpha production in mouse RAW264.7 cells treated with varying concentrations of a compound according to the invention.

FIG. 6 shows a graph of the inhibition of LPS-induced IL-1 beta production in mouse RAW264.7 cells treated with varying concentrations of a compound according to the invention.

FIG. 7 shows a graph of the inhibition of LPS-induced IL-6 production in mouse RAW264.7 cells treated with varying concentrations of a compound according to the invention.

FIG. 8 shows photos of Western blots demonstrating the inhibition of LPS-induced iNOS and COX-2 production in mouse RAW264.7 cells treated with varying concentrations of a compound according to the invention.

FIG. 9 shows a graph of median clinical scores over time demonstrating improvement of collagen induced arthritis in mice using varying concentrations of a compound according to the invention.

DETAILED DESCRIPTION OF THE INVENTION

The invention is based on the discovery that the compounds described herein are useful in the treatment of diseases, in particular diabetes and other diseases linked to insulin resistance, such as coronary artery disease and peripheral vascular disease, and also for the treatment or inhibition of inflammation or inflammatory diseases such as inflammatory arthritides and collagen vascular diseases, which are caused by, for example, cytokines or inducible enzymes such as TNF-alpha, IL-1, IL-6, PDE4, PDE3, p44/42 MAP kinase, iNOS and/or COX-2.

Definitions

As utilized herein, the following terms, unless otherwise indicated, shall be understood to have the following meanings:

"Alkyl", alone or in combination, means a straight-chain or branched-chain alkyl radical containing preferably 1-20 carbon atoms, more preferably 1-10 carbon atoms, and most preferably 1-6 carbon atoms. Exemplary alkyl radicals include methyl, ethyl, n-propyl, isopropyl, n-butyl, isobutyl, sec-butyl, tert-butyl, pentyl, isopentyl, neopentyl, iso-amyl, hexyl and the like.

"Alkenyl", alone or in combination, means a straight-chain or branched-chain hydrocarbon radical having one or more double bonds, preferably 1-2 double bonds and more preferably one double bond, and containing preferably 2-20 carbon atoms, more preferably 2-10 carbon atoms, and still more preferably 2-6 carbon atoms. Exemplary alkenyl radicals include ethenyl, propenyl, 2-methylpropenyl, n-butenyl, isobutenyl, and include groups containing multiple sites of unsaturation such as 1,3-butadiene and 1,4-butadienyl and the like.

"Alkoxy", alone or in combination, means a radical of the type "R—O—" wherein R can be hydrogen, linear or branched alkyl, or linear or branched alkenyl as previously defined and "O" is an oxygen atom. Exemplary alkoxy radicals include methoxy, ethoxy, n-propoxy, isopropoxy, n-butoxy, iso-butoxy, sec-butoxy, tert-butoxy and the like.

"Alkoxycarbonyl", alone or in combination, means a radical of the type "R—O—C(O)—" wherein "R—O—" is an alkoxy radical as previously defined and "C(O)—" is a carbonyl radical. Exemplary alkoxycarbonyl groups include methoxycarbonyl and ethoxycarbonyl.

"Alkylcarboxylamino" means a group RCON(R)— where R can be independently hydrogen, linear or branched alkyl, or linear or branched alkenyl as previously defined.

"Alkanoyl", alone or in combination, means a radical of the type "R—C(O)—" wherein "R" is an alkyl radical as previously defined and "—C(O)—" is a carbonyl radical. Exemplary alkanoyl radicals include acetyl, trifluoroacetyl, hydroxyacetyl, propionyl, butyryl, valeryl, 4-methylvaleryl and the like.

"Halo" or "halogen", alone or in combination, means chloro, bromo, fluoro or iodo radicals.

"Aryl", alone or in combination, means an aromatic carbocyclic radical containing about 6 to about 10 carbon atoms, which is optionally substituted with one or more substituents selected from alkyl, alkoxy, halogen, hydroxy, amino, azido, nitro, cyano, haloalkyl, carboxy, alkoxycarbonyl, cycloalkyl, alkanoylamino, amido, amidino, alkoxycarbonylamino, N-alkylamidino, alkylamino, dialkylamino, aminoalkyl, alkylaminoalkyl, dialkylaminoalkyl, N-alkylamido, N,N-dialkylamido, aralkoxycarbonylamino, alkylthio, alkylsulfinyl, alkylsulfonyl, oxo and the like. Exemplary aryl radicals include phenyl, o-tolyl, 4-methoxyphenyl, 2-(tert-butoxy)phenyl, 3-methyl-4-methoxyphenyl, 2-fluorophenyl, 2-chlorophenyl, 3-nitrophenyl, 3-aminophenyl, 3-acetamidophenyl, 2-amino-3-(aminomethyl)phenyl, 6-methyl-2-aminophenyl, 2-amino-3-methylphenyl, 4,6-dimethyl-2-aminophenyl, 4-hydroxyphenyl, 3-methyl-4-hydroxyphenyl, 4-(2-methoxyphenyl)phenyl, 2-amino-1-naphthyl, 2-naphthyl, 1-methyl-3-amino-2-naphthyl, 2,3-diamino-1-naphthyl, 4,8-dimethoxy-2-naphthyl and the like.

"Acyloxy" or "Acylamino" group means an oxygen or amino group, respectively, bonded to an acyl group (RCO) where R can be hydrogen, linear or branched alkyl, or linear or branched alkenyl.

"Alkylamido" means the group RN(H)CO— where R can be hydrogen, linear or branched alkyl, or linear or branched alkenyl, as previously defined.

The reference to "optionally substituted" in the definition of the compounds throughout this disclosure is intended to include any substituent which does not negatively affect the activity of the compounds. Typical substitution includes, for example, lower ($C_1$-$C_6$) alkyl; halogen such as fluoro, chloro and bromo; nitro; amino; lower alkylamino; carboxylate, lower alkyl carboxylate, hydroxy, lower alkoxy, sulfonamide, cyano, or the like.

A "therapeutically effective amount" is an amount, alone or in combination with other agents, sufficient to elicit a therapeutic response to the desired disease, symptom or condition. The specific therapeutically effective amount will vary with such factors as the particular condition being treated, the physical condition of the patient, the type of mammal or animal being treated, the duration of the treatment, and the specific formulations employed and the form of the compound or compounds used.

Throughout the specification various numbers are used in reference to chemical structures or chemical names. The use of such numbers herein shall represent the referenced compound itself.

The invention is directed to compounds, for example, heterocyclic derivatives of acyl urea, thiourea, carbamate and thiocarbamate compounds, that provide a variety of useful pharmacological effects. The compounds are useful, for example, in lowering blood glucose levels in hyperglycemic disorders, such as diabetes mellitus, and for treating related disorders, such as obesity and hyperlipidemia. Furthermore, these compounds are useful for treatment of disorders associated with insulin resistance, such as polycystic ovary syndrome, and for the treatment of inflammation, inflammatory and immunological diseases, particularly those mediated by pro-inflammatory cytokines (such as TNF-alpha, IL-1 beta and IL-6), type 4 phosphodiesterase (PDE4), type 3 phosphodiesterase (PDE3), p44/42 mitogen activated protein (MAP) kinase, cyclooxygenase-2 (COX-2) and/or inducible nitric oxide synthase (iNOS). In particular, the invention discloses compounds of the Formulas I-XIII as well as the pharmaceutically acceptable salts, hydrates or solvates thereof:

(I)

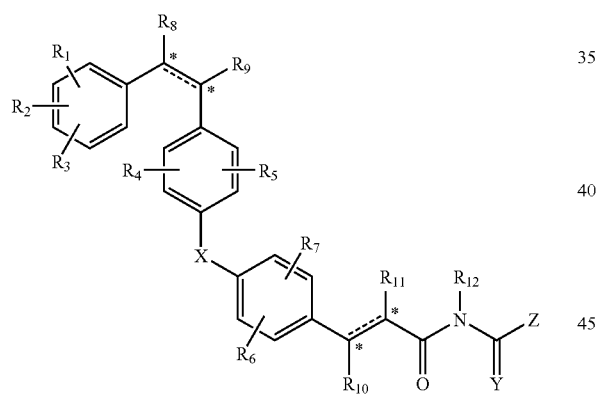

(II)

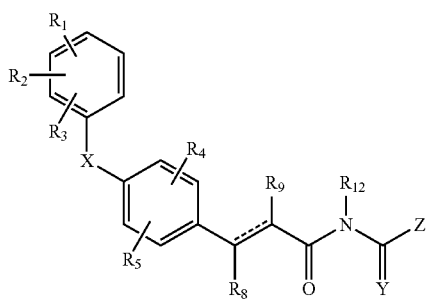

-continued (III)

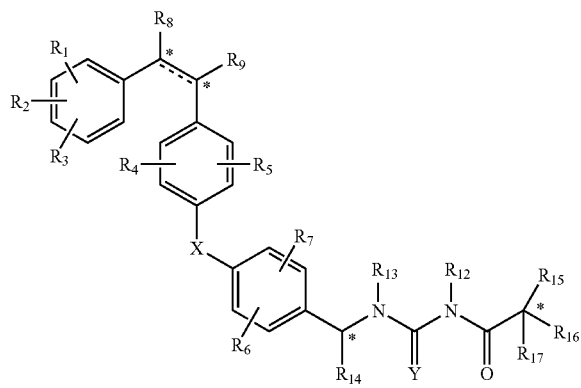

(IV)

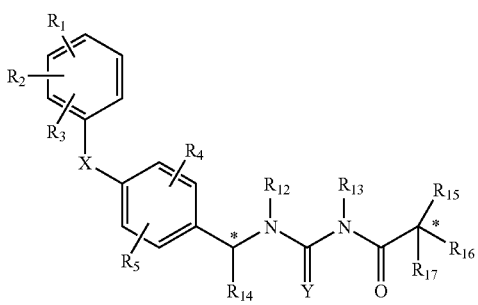

(V)

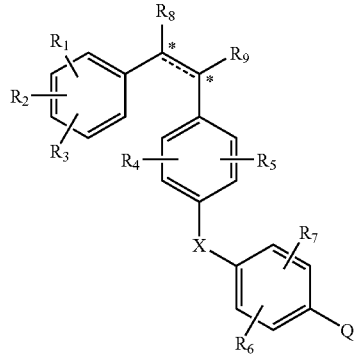

(VI)

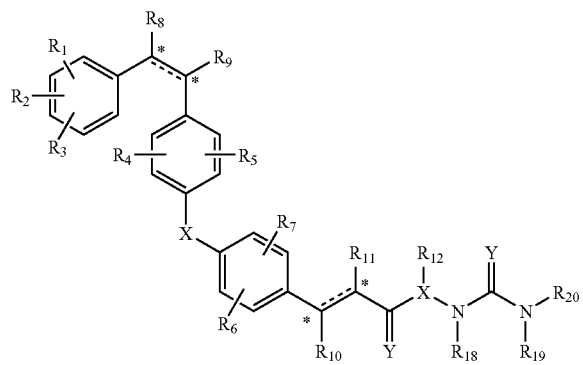

-continued

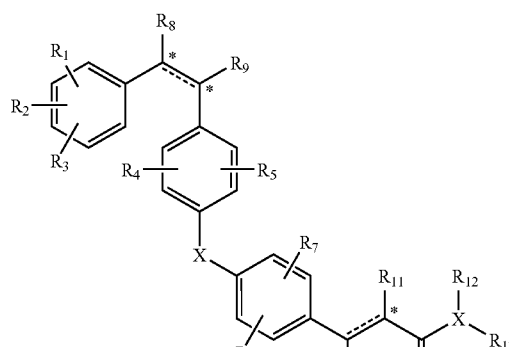
(VII)

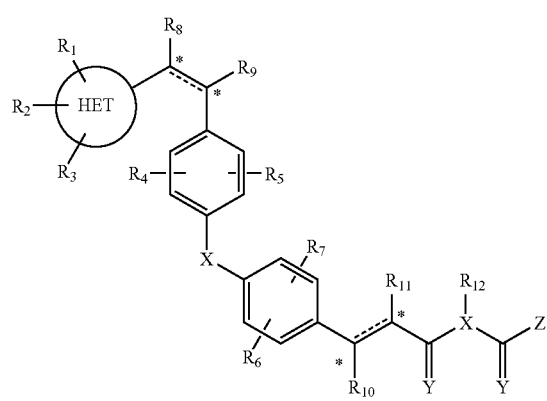
(VIII)

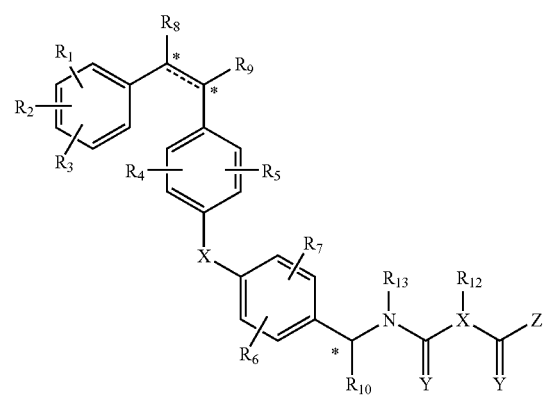
(IX)

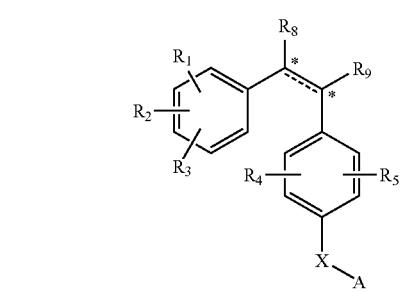
(X)

-continued

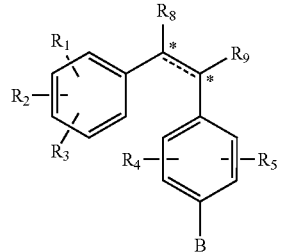
(XI)

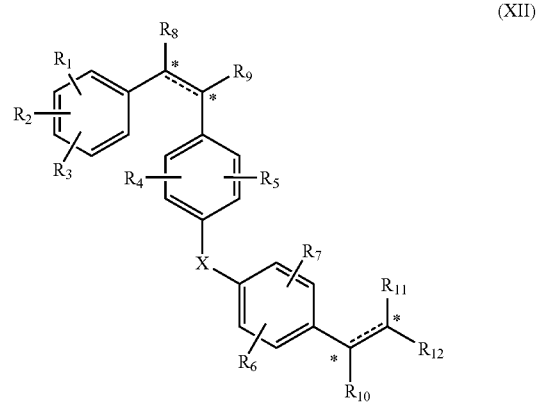
(XII)

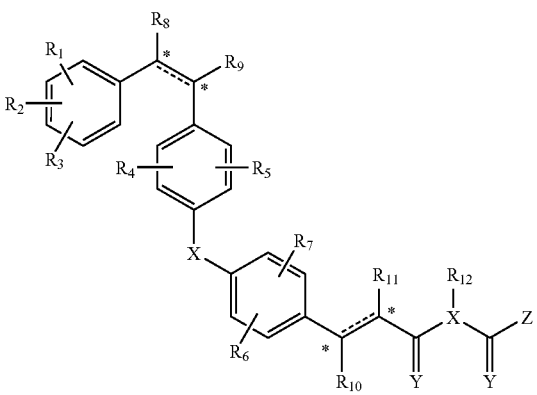
(XIII)

wherein the stereocenters marked with an asterisk (*) may be R— or S—; the bond represented by a dashed line plus a solid line may be a doulbe bond or a single bond, and when the bond is a double bond it may be in the E or Z configuration, and when the bond is a single bond the resulting stereocenters may have the R— or S— configuration; and $R_1$, $R_2$, $R_3$, $R_4$, $R_5$, $R_6$ and $R_7$ are each independently selected from the group consisting of H; optionally substituted $C_1$-$C_{20}$ linear or branched alkyl including chloroalkyl or fluoroalkyl; optionally substituted $C_2$-$C_{20}$ linear or branched alkenyl; optionally substituted $C_6$-$C_{20}$ aryl, linear or branched alkylaryl, linear or branched alkenylaryl; COOR where R is H, optionally substituted $C_1$-$C_{20}$ alkyl, optionally substituted $C_2$-$C_{20}$ alkenyl or optionally substituted $C_6$-$C_{10}$ aryl, sodium, potassium or other pharmaceutically acceptable counterion such as calcium, magnesium, ammonium, tromethamine and the like; CONR'R", where R' and R" are independently H. optionally substituted $C_1$-$C_{20}$ alkyl, optionally substituted $C_2$-$C_{20}$ alkenyl or optionally substituted $C_6$-$C_{10}$ aryl or where NR'R" represents a cyclic moiety such as morpholine, piperidine, piperazine and the like; optionally substituted $C_1$-$C_6$ amidoalkyl; $NH_2$; $C_1$-$C_{20}$ alkylamino, bis(alkylamino), cycloalkylamino or cyclic amino; OH; optionally substituted $C_1$-$C_{20}$ alkoxy including trifluoromethoxy and the like; optionally substituted $C_1$-$C_{20}$ alkanoyl; optionally substituted $C_1$-$C_{20}$ acyloxy; halo; optionally substituted $C_1$-$C_{20}$ alkylcarboxylamino; cyano; nitro; $SO_2NR'''R''''$ where R''' and R'''' are independently H, $C_1$-$C_{20}$ alkyl or aryl; $SO_2R'''$ where R''' is H, $C_1$-$C_{20}$ alkyl or aryl; $SO_3R'''$ where R''' is H, $C_1$-$C_{20}$ alkyl or aryl; and $C_4$-$C_8$ heterocycles such as tetrazolyl, imidazolyl, pyrrolyl, pyridyl, indolyl and the like; or when individual aromatic rings possess adjacent substituents, these substituents may be joined to form a ring such as a methylenedioxy or ethylenedioxy group, and the like, including lactones and lactams;

$R_8$ and $R_9$ are each independently selected from the group consisting of

H; optionally substituted $C_1$-$C_{20}$ linear or branched alkyl; optionally substituted $C_2$-$C_{20}$ linear or branched alkenyl; optionally substituted $C_6$-$C_{10}$ aryl or heteroaryl; COOR where R is H, optionally substituted $C_1$-$C_{20}$ alkyl, optionally substituted $C_2$-$C_{20}$ alkenyl or optionally substituted $C_6$-$C_{10}$ aryl, sodium, potassium or other pharmaceutically acceptable counter-ion such as calcium, magnesium, ammonium, tromethamine and the like; CONR'R", where R' and R" are independently H, alkoxy, optionally substituted $C_1$-$C_{20}$ alkyl, optionally substituted $C_2$-$C_{20}$ alkenyl, optionally substituted $C_3$-$C_{10}$ cycloalkyl or cycloalkenyl or optionally substituted $C_6$-$C_{10}$ aryl or heteroaryl, preferably 2-, 3- or 4-pyridyl or where NR'R" represents a cyclic moiety such as morpholine, piperidine, hydroxypi peridine, imidazole, piperazine, methylpiperazine and the like; $NH_2$; $C_1$-$C_{20}$ alkylamino, bis(alkylamino), cycloalkylamino or cyclic amino; OH; $C_1$-$C_{20}$ alkoxy; $C_1$-$C_{20}$ alkanoyl; $C_1$-$C_{20}$ acyloxy; halo; $C_1$-$C_{20}$ alkylcarboxylamino; cyano; nitro; $SO_2NR'''R''''$ where R''' and R''''. are independently H, $C_1$-$C_{20}$ alkyl or aryl; $SO_2R'''$ where R''' is H, $C_1$-$C_{20}$ alkyl or aryl; $SO_3R'''$ where R''' is H, $C_1$-$C_{20}$ alkyl or aryl; and tetrazolyl; wherein $R_8$ and $R_9$ together may be joined to form a $C_4$-$C_8$ heterocyclic ring, including lactone or lactam;

$R_{10}$ and $R_{11}$ are each independently selected from the group consisting of H; optionally substituted $C_1$-$C_{20}$ linear or branched alkyl; optionally substituted $C_2$-$C_{20}$ linear or branched alkenyl; optionally substituted $C_6$-$C_{10}$ aryl or heteroaryl; COOR where R is H, optionally substituted $C_1$-$C_{20}$ alkyl, optionally substituted $C_2$-$C_{20}$ alkenyl or optionally substituted $C_6$-$C_{10}$ aryl, sodium, potassium or other pharmaceutically acceptable counter-ion such as calcium, magnesium, ammonium, tromethamine and the like; CONR'R", where R' and R" are independently H, optionally substituted $C_1$-$C_{20}$ alkyl, optionally substituted $C_2$-$C_{20}$ alkenyl or optionally substituted $C_6$-$C_{10}$ aryl or where NR'R" represents a cyclic moiety such as morpholine, piperidine, piperazine and the like; $NH_2$; $C_1$-$C_{20}$ alkylamino, bis(alkylamino), cycloalkylamino or cyclic amino; OH; $C_1$-$C_{20}$ alkoxy; $C_1$-$C_{20}$ alkanoyl; $C_1$-$C_{20}$ acyloxy; halo; $C_1$-$C_{20}$ alkylcarboxylamino; cyano; nitro; $SO_2NR'''R''''$ where R''' and R'''' are independently H, $C_1$-$C_{20}$ alkyl or aryl; $SO_2R'''$ where R''' is H, $C_1$-$C_{20}$ alkyl or aryl; $SO_3R'''$ where R''' is H, $C_1$-$C_{20}$ alkyl or aryl; and tetrazolyl; wherein $R_{10}$ and $R_{11}$ together may be joined to form a $C_4$-$C_8$ heterocyclic ring, including lactone or lactam;

$R_{12}$, $R_{13}$, $R_{18}$, $R_{19}$ and $R_{20}$ are each independently selected from the group consisting of H; optionally substituted $C_1$-$C_{20}$ linear or branched alkyl; optionally substituted $C_2$-$C_{20}$ linear or branched alkenyl; optionally substituted $C_6$-$C_{10}$ aryl or heteroaryl; COOR where R is optionally substituted $C_1$-$C_{20}$ alkyl, optionally substituted $C_2$-$C_{20}$ alkenyl or optionally substituted $C_6$-$C_{10}$ aryl, sodium, potassium or other pharmaceutically acceptable counter-ion such as calcium, magnesium, ammonium, tromethamine and the like; CONR'R", where R' and R" are independently H, optionally substituted $C_1$-$C_{20}$ alkyl, optionally substituted $C_2$-$C_{20}$ alkenyl or optionally substituted $C_6$-$C_{10}$ aryl or where NR'R" represents a cyclic moiety such as morpholine, piperidine, piperazine and the like; $C_1$-$C_{20}$ alkanoyl; $C_1$-$C_{20}$ alkylamido; $C_6$-$C_{20}$ aroyl or heteroaroyl; $SO_2R'''$ where R''' is H, $C_1$-$C_{20}$ alkyl or aryl; morpholinocarbonylmethyl; piperazinocabonylmethyl; and piperadinocabonylmethyl;

$R_{12}$ and $R_{13}$ may be absent, or $R_{12}$ and $R_{13}$ together may be an optionally substituted heterocyclic ring, preferably morpholine, piperidine, piperazine, and N-methyl piperidine.

$R_{14}$ is selected from the group consisting of

H; optionally substituted $C_1$-$C_{20}$ linear or branched alkyl including chloroalkyl and fluoroalkyl; optionally substituted $C_2$-$C_{20}$ linear or branched alkenyl; optionally substituted $C_6$-$C_{10}$ aryl or heteroaryl; COOR where R is H, optionally substituted $C_1$-$C_{20}$ alkyl, optionally substituted $C_2$-$C_{20}$ alkenyl or optionally substituted $C_6$-$C_{10}$ aryl, sodium, potassium or other pharmaceutically acceptable counter-ion such as calcium, magnesium, ammonium, tromethamine and the like; CONR'R", where R' and R" are independently H, optionally substituted $C_1$-$C_{20}$ alkyl, optionally substituted $C_2$-$C_{20}$ alkenyl or optionally substituted $C_6$-$C_{10}$ aryl or where NR'R" represents a cyclic moiety such as morpholine, piperidine, piperazine and the like; cyano; and tetrazolyl;

$R_{15}$, $R_{16}$, and $R_{17}$ are each independently selected from the group consisting of H; optionally substituted $C_1$-$C_{20}$ linear or branched alkyl including chloroalkyl and fluoroalkyl; optionally substituted $C_2$-$C_{20}$ linear or branched alkenyl; optionally substituted $C_6$-$C_{10}$ aryl or heteroaryl; COOR where R is H, optionally substituted $C_1$-$C_{20}$ alkyl, optionally substituted $C_2$-$C_{20}$ alkenyl or optionally substituted $C_6$-$C_{10}$ aryl, sodium, potassium or other pharmaceutically acceptable counter-ion such as calcium, magnesium, ammonium, tromethamine and the like; CONR'R", where R' and R" are independently H, optionally substituted $C_1$-$C_{20}$ alkyl, optionally substituted $C_2$-$C_{20}$ alkenyl or optionally substituted $C_6$-$C_{10}$ aryl or where NR'R" represents a cyclic moiety such as morpholine, piperidine, piperazine and the like; $NH_2$; $C_1$-$C_{20}$ alkylamino, bis(alkylamino), cycloalkylamino or cyclic amino; OH; $C_1$-$C_{20}$ alkoxy; $C_1$-$C_{20}$ alkanoyl; $C_1$-$C_{20}$ acyloxy; halo; $C_1$-$C_{20}$ alkylcarboxylamino; cyano; nitro; $SO_2NR'''R''''$ where R''' and R'''' are independently H, $C_1$-$C_{20}$ alkyl or aryl; $SO_2R'''$ where R''' is H, $C_1$-$C_{20}$ alkyl or aryl; $SO_3R'''$ where R''' is H, $C_1$-$C_{20}$ alkyl or aryl; and tetrazolyl;

X is independently selected from the group consisting of

O; N; S; S=O; $SO_2$; or NR'''', where R'''' may be H or optionally substituted $C_1$-$C_{20}$ alkyl, optionally substituted $C_2$-$C_{20}$ alkenyl, optionally substituted $C_1$-$C_{20}$ acyl, optionally substituted $C_1$-$C_{20}$ acyloxy and optionally substituted $C_1$-$C_{20}$ alkoxycarbonyl;

Y is independently O, S or NH;

Z is $OR_a$ where $R_a$ is selected from the group consisting of

H; optionally substituted $C_1$-$C_{20}$ linear or branched alkyl including chloroalkyl or fluoroalkyl and the like; optionally substituted $C_2$-$C_{20}$ linear or branched alkenyl; optionally substituted $C_6$-$C_{10}$ aryl or heteroaryl; optionally substituted $C_6$-$C_{20}$ aroyl or heteroaroyl; optionally substituted $C_1$-$C_{20}$ alkanoyl; and $SO_2R'''$ where $R'''$ is H, $C_1$-$C_{20}$ alkyl or aryl; or Z is $NR_bR_c$ where $R_b$ and $R_c$ are independently selected from the group consisting of H; optionally substituted $C_1$-$C_{20}$ linear or branched alkyl including chloroalkyl or fluoroalkyl and the like; optionally substituted $C_2$-$C_{20}$ linear or branched alkenyl; optionally substituted $C_6$-$C_{10}$ aryl or heteroaryl; $COOZ_1$ where $Z_1$ is optionally substituted $C_1$-$C_{20}$ alkyl, optionally substituted $C_2$-$C_{20}$ alkenyl or optionally substituted $C_6$-$C_{10}$ aryl; optionally substituted $C_6$-$C_{20}$ aroyl or heteroaroyl; optionally substituted $C_1$-$C_{20}$ alkanoyl; and $SO_2R'''$ where $R'''$ is H, $C_1$-$C_{20}$ alkyl or aryl; and wherein $R_b$ and $R_c$ together may be joined to form a 3-6 membered ring such as aziridine, morpholine, piperidine, piperazine and the like; or Z is $CR_dR_eR_f$ where $R_d$, $R_e$ and $R_f$ are each independently selected from the group consisting of H; optionally substituted $C_1$-$C_{20}$ linear or branched alkyl including chloroalkyl or fluoroalkyl and the like; optionally substituted $C_2$-$C_{20}$ linear or branched alkenyl; optionally substituted $C_6$-$C_{10}$ aryl or heteroaryl; COOR where R is H, optionally substituted $C_1$-$C_{20}$ alkyl, optionally substituted $C_2$-$C_{20}$ alkenyl or optionally substituted $C_6$-$C_{10}$ aryl, sodium, potassium or other pharmaceutically acceptable counter-ion such as calcium, magnesium, ammonium, tromethamine and the like; $NH_2$; $C_1$-$C_{20}$ alkylamino, bis(alkylamino); cycloalkylamino or cyclic amino; OH; optionally substituted $C_1$-$C_{20}$ alkoxy including trifluoromethoxy and the like; optionally substituted $C_1$-$C_{20}$ alkanoyl; optionally substituted $C_1$-$C_{20}$ acyloxy; optionally substituted $C_6$-$C_{20}$ aroyl or heteroaroyl; halo, cyano; nitro; optionally substituted $C_1$-$C_{20}$ alkylcarboxylamino; $SO_2NR'''R''''$ where $R'''$ and $R''''$ are independently H, $C_1$-$C_{20}$ alkyl or aryl; $SO_2R'''$ where $R'''$ is H, $C_1$-$C_{20}$ alkyl or aryl; and $SO_3R'''$ where $R'''$ is H, $C_1$-$C_{20}$ alkyl or aryl; and wherein $R_d$ and $R_e$ together may be joined to form a 3-6 membered ring such as aziridine, morpholine, piperidine, piperazine and the like; and the resulting stereocenter may have the R— or S— configuration; or the grouping —C(=Y)Z may represent hydrogen or $R_{12}$ or may be absent.

Q is $OR_a$ where $R_a$ is selected from the group consisting of

H; optionally substituted $C_1$-$C_{20}$ linear or branched alkyl including chloroalkyl or fluoroalkyl and the like; optionally substituted $C_2$-$C_{20}$ linear or branched alkenyl; optionally substituted $C_6$-$C_{10}$ aryl or heteroaryl; optionally substituted $C_6$-$C_{20}$ aroyl or heteroaroyl; optionally substituted $C_1$-$C_{20}$ alkanoyl; and $SO_2R'''$ where $R'''$ is H, $C_1$-$C_{20}$ alkyl or aryl; or Q is $NR_bR_c$ where $R_b$ and $R_c$ are independently selected from the group consisting of H; optionally substituted $C_1$-$C_{20}$ linear or branched alkyl including chloroalkyl or fluoroalkyl and the like; optionally substituted $C_2$-$C_{20}$ linear or branched alkenyl; optionally substituted $C_6$-$C_{10}$ aryl or heteroaryl; optionally substituted $C_3$-$C_{10}$ cycloalkyl or cycloalkenyl; $COOZ_1$ where $Z_1$ is optionally substituted $C_1$-$C_{20}$ alkyl, optionally substituted $C_2$-$C_{20}$ alkenyl or optionally substituted $C_6$-$C_{10}$ aryl; optionally substituted $C_6$-$C_{20}$ aroyl or heteroaroyl; optionally substituted $C_1$-$C_{20}$ alkanoyl; and $SO_2R'''$ where $R'''$ is H, $C_1$-$C_{20}$ alkyl or aryl; and wherein $R_b$ and $R_c$ together may be joined to form a 3-6 membered ring such as aziridine, morpholine, piperidine, piperazine and the like; or Q is $SR_g$, $SOR_g$ or $SO_2R_g$ where $R_g$ is selected from the group consisting of H; optionally substituted $C_1$-$C_{20}$ linear or branched alkyl including chloroalkyl or floroalkyl and the like; optionally substituted $C_2$-$C_{20}$ linear or branched alkenyl; optionally substituted $C_1$-$C_{20}$ acyl; optionally substituted $C_1$-$C_{20}$ alkoxycarbonyl; $C_2$-$C_{20}$ alkoxy; optionally substituted $C_6$-$C_{10}$ aryl or heteroaryl; and optionally substituted $C_6$-$C_{10}$ aroyl or heteroaroyl.

Group A is optionally substituted $C_2$-$C_{20}$ linear or branched alkenyl; optionally substituted $C_6$-$C_{20}$ aryl, linear or branched alkylaryl, linear or branched alkenylaryl; optionally substituted heteroaryls like pyridine, indole, morpholine, piperidine, piperazine, tetrazoly and the like; COR where R is optionally substituted $C_1$-$C_{20}$ linear or branched alkyl; optionally substituted $C_2$-$C_{20}$ linear or branched alkenyl; optionally substituted $C_6$-$C_{20}$ aryl linear or branched alkylaryl, linear or branched alkenylaryl; optionally substituted heteroaryls like pyridine, indole, morpholine, piperidine, piperazine, tetrazolyl and the like;

Group B is OH, $C_1$-$C_{20}$ alkoxy; $SO_2R$ where R may be H or linear or branched $C_1$-$C_{20}$ alkyl.

Group Het represents a heterocyclic ring which is pyridyl, indolyl, tetrazolyl, imidazolyl, morphonyl, piperidinyl, piperazinyl, thiophenyl or the like.

Preferably, the compounds of the present invention are represented by Formulas I or VIII. Preferred compounds represented by Formulas I or VIII include those where at least one of the bonds represented by a dashed line plus a solid line is a double bond or a single bond, for example, where the bond represented by a dashed line plus a solid line between the carbons with the group $R_8$ and $R_9$ attached is a double-bond. Furthermore, preferred compounds include those where at least one of $R_8$ or $R_9$ represents CONR'R", wherein R' and R" independently represent a hydrogen atom, or an alkoxy, optionally substituted $C_1$-$C_{20}$ alkyl, optionally substituted $C_2$-$C_{20}$ alkenyl, optionally substituted $C_3$-$C_{10}$ cycloalkyl, optionally substituted cycloalkenyl, optionally substituted $C_6$-$C_{10}$ aryl or optionally substituted $C_6$-$C_{10}$ heteroaryl, or where NR'R" represents a cyclic moiety; for example where, R' and R" independently represent a hydrogen atom, or an alkoxy, optionally substituted $C_1$-$C_{20}$ alkyl, optionally substituted $C_6$-$C_{10}$ aryl or optionally substituted $C_6$-$C_{10}$ heteroaryl. Preferably, R' and R" independently represent a hydrogen atom, or an alkoxy, or optionally substituted $C_1$-$C_{20}$ alkyl, for example, where each of R' and R" represent a hydrogen atom. Preferably, at least one of $R_8$ or $R_9$ represents a hydrogen atom, for example, where $R_8$ represents a hydrogen atom. X represents an oxygen or nitrogen atom, for example, an oxygen atom and Y represents an oxygen atom. Z represents $NR_bR_c$, for example, where $R_b$ and $R_c$ independently represent a hydrogen atom; or an optionally substituted $C_1$-$C_{20}$ linear or branched alkyl, optionally substituted $C_2$-$C_{20}$ linear or branched alkenyl, optionally substituted $C_6$-$C_{10}$ aryl, optionally substituted heteroaryl; optionally substituted $C_3$-$C_{10}$ cycloalkyl or optionally substituted $C_3$-$C_{10}$ cycloalkenyl. Preferably, $R_b$ and $R_c$ independently represent a hydrogen atom, or an optionally substituted $C_1$-$C_{20}$ linear or branched alkyl, optionally substituted $C_6$-$C_{10}$ aryl, optionally substituted heteroaryl, or optionally substituted $C_3$-$C_{10}$ cycloalkyl. More preferably, $R_b$ and $R_c$ independently represent a hydrogen atom, or an optionally substituted $C_1$-$C_8$ linear or branched alkyl, for example where at least one of $R_b$ or $R_c$ represents a hydrogen atom or Z represents the radical $NH_2$.

Additionally preferred compounds of Formulas I and VIII include those where $R_1$, $R_2$, $R_3$, $R_4$, $R_5$, $R_6$, $R_7$, $R_{10}$, $R_{11}$, and $R_{12}$ independently represent a hydrogen atom or an optionally substituted $C_1$-$C_{20}$ linear or branched alkyl, for example a $C_1$-$C_4$ linear or branched alkyl, or optionally substituted $C_1$-$C_{20}$ alkoxy, for example an optionally substituted $C_1$-$C_4$ alkoxy. Preferably, at least one of $R_1$, $R_2$, $R_3$, $R_4$, $R_5$, $R_6$, and $R_7$ independently represent an optionally substituted $C_1$-$C_4$ alkoxy, for example, where at least one of $R_1$ or $R_2$ independently represent an optionally substituted $C_1$-$C_4$ alkoxy. More preferably at least two of $R_1$, $R_2$, $R_3$, $R_4$, $R_5$, $R_6$ and $R_7$ independently represent an optionally substituted $C_1$-$C_4$ alkoxy, for example, where $R_1$ and $R_2$ independently represent an optionally substituted $C_1$-$C_4$ alkoxy, such as methoxy. Preferably, $R_1$ and $R_2$ are present in the 3 and 5 position on the aromatic ring. Other preferred compounds of the Formulas I and VIII include where the grouping —C(=Y)Z represents hydrogen, and alternatively compounds of Formula VIII including those combinations of the variables and preferences set forth above where the Het group represents pyridyl or indolyl, for example, pyridyl.

Representative preferred compounds of the Formulas I and VIII include 3-(3,5-Dimethoxyphenyl)-N,N-dimethyl-2-{4-[4-(3-oxo-3-ureido-propyl)-phenoxy]-phenyl}-acrilamide (13); 2-{4-[4-(2-Carbamoylethyl)-phenoxy]-phenyl}-3-(3,5-dimethoxyphenyl)-N,N-dimethylacrylamide (31); N,N-Dimethyl-2-{4-[4-(3-oxo-3-ureidopropyl)-phenoxy]-phenyl }-3-pyridin-3-yl-acrylamide (73); and 2-{4-[4-(2-Carbamoyl-ethyl)-phenoxy]-phenyl }-N,N-dimethyl-3-pyridin-3-yl-acrylamide (77).

These compounds are useful for treating diabetes and other diseases linked to insulin resistance, such as coronary artery disease and peripheral vascular disease, and also for treating or inhibiting inflammation or inflammatory diseases such as inflammatory arthritides and collagen vascular diseases, which are caused by, for example, cytokines or inducible enzymes such as TNF-alpha, IL-1, IL-6, PDE4, PDE3, p44/42 MAP kinase, iNOS and/or COX-2. The compounds are also useful for treating or preventing other diseases mediated by cytokines, PDE4, PDE3, p44/42 MAP kinase, iNOS and/or COX-2, such as cancer.

As indicated above, the compounds of the invention include bonds, designated in Formulas I-XIII with a dashed line plus a solid line, that may be either a double bond or a single bond. When such a bond is a double bond, it may have either the E or Z configuration. On the other hand, when such a bond is a single bond, the resulting stereocenters may be in the R— and/or S— configurations. Likewise, compounds of the invention with other stereocenters, designated in Formulas I-XIII with an asterisk, may be R— and/or S— stereoisomers. The invention contemplates racemic mixtures of such stereoisomers as well as the individual, separated stereoisomers. The individual stereoisomers may be obtained by the use of an optically active resolving agent. Alternatively, a desired enantiomer may be obtained by stereospecific synthesis using an optically pure starting material of known configuration.

Generally, R— or S— refers to the configuration of the stereoisomers. The determination of whether the configuration is R— (rectus) or S— (sinister) is based on the priority of the atoms in a compound. Similarly, E- or Z-configuration is used when describing compounds with double bonds and wherein the determination is based on the priority of the atom on each carbon of a double bond. In the preferred compounds of the present invention the double bond is in the "E" configuration.

The following compounds are representative of the preferred compounds according to Formula I:
3-(3,5-Dimethoxyphenyl)-2-{4-[4-(3-oxo-3-ureidopropyl)-phenoxy]-phenyl}-acrylic acid methyl ester (1);
3-(3,5-Dimethoxyphenyl)-2-{4-[4-(3-oxo-3-ureidopropyl)-phenoxy]-phenyl}-acrylic acid (6);
3-(3,5-Dimethoxyphenyl)-2-{4-[4-(3-ethoxycarbonylamino-3-oxo-propyl)-phenoxy]-phenyl}-acrilyc acid methyl ester (8);
2-{4-[4-(3-Benzoyloxycarbonylamino-3-oxo-propyl)-phenoxy]-phenyl}-3-(3,5-dimethoxyphenyl)-acrylic acid methyl ester (9);
3-(3,5-Dimethoxyphenyl)-2-{4-[4-(3-oxo-3-ureidopropyl)-phenoxy]-phenyl}-propionic acid (10);
3-(3,5-Dimethoxyphenyl)-2-{4-[4-(3-oxo-3-ureidopropenyl)-phenoxy]-phenyl}-acrylic acid (11);
3-(3,5-Dimethoxyphenyl)-2-{4-[4-(3-oxo-3-ureidopropyl)-phenoxy]-phenyl}-acrylic acid ethyl ester (12);
3-(3,5-Dimethoxyphenyl)-N,N-dimethyl-2-{4-[4-(3-oxo-3-ureidopropyl)-phenoxy]-phenyl}-acrylamide (13);
2-(4-{4-[3-(3-Cyclohexylureido)-3-oxopropyl]-phenoxy}-phenyl)-3-(3,5-methoxyphenyl)-acrylic acid (14).

The following are preferred compounds according to Formula II: [3-(4-Phenoxyphenyl)-propionyl]-urea (15); {3-[4-(4-Methoxyphenoxy)-phenyl]-acryloyl}-urea (16).

The following are preferred compounds according to Formula III:
2-{4-[4-(3-Acetylureidomethyl)-phenoxy]-phenyl}-3-(3,5-dimethoxyphenyl)-acrylic acid methyl ester (17);
2-{4-[4-(3-Acetylthioureidomethyl)-phenoxy]-phenyl}-3-(3,5-dimethoxyphenyl)-acrylic acid (18).

The following are preferred compounds according to Formula IV:
1-Acetyl-3-[4-(4-methoxyphenoxy)-benzyl]-urea (24);
Acetyl-3-[4-(3,4-dimethoxyphenoxy)-benzyl]-urea (25).

The following are more preferred compounds for their anti-inflammatory properties:
3-(3,5-Dimethoxyphenyl)-N,N-dimethyl-2-{4-[4-(3-oxo-3-ureidopropyl)-phenoxy]-phenyl}-acrylamide (13);
2-{4-[4-(2-Carbamoylethyl)-phenoxy]-phenyl}-3-(3,5-dimethoxyphenyl)-N,N-dimethylacrylamide (31);
3-(4-{4-[2-(3,5-Dimethoxyphenyl)-1-dimethylcarbamoylvinyl]-phenoxy}-phenyl)-propionic acid ethyl ester (37);
N-{4-[2-(3,5-Dimethoxyphenyl)-1-dimethylcarbamoylvinyl]-phenyl}-3-hydroxybenzamide (44);
3-(3,5-Dimethoxyphenyl)-2-(4-hydroxyphenyl)-N,N-dimethylacrylamide (49);
[3-(4-{4-[2-(3,5-Dimethoxyphenyl)-1-(piperidine-1-carbonyl)-vinyl]-phenoxy}-phenyl)-prpionyl]-urea (51);
2-{4-[4-(3-Acetylamino-3-oxopropyl)-phenoxy]-phenyl}-3-(4-fluorophenyl)-N,N-dimethylacrylamide (56);
2-(4-{4-[2-(3,5-Dimethoxyphenyl)-1-dimethylcarbamoylvinyl]-phenoxy}-benzyl)-malonic acid (58);
2-(4-{4-[2-(3,5-Dimethoxyphenyl)-1-dimethylcarbamoylvinyl]-phenoxy}-benzyl)-malonamide (59);
3-(3,5-Dimethoxyphenyl)-N,N-dimethyl-2-[4-(pyridin-2-yloxy)-phenyl]-acrylamide (66);
N-{4-[2-(3,5-Dimethoxyphenyl)-1-dimethylcarbamoyl-vinyl]-phenyl}-benzamide (67);
2-{4-[4-(1-Dimethylcarbamoyl-2-pyridin-3-yl-vinyl)-phenoxy]-benzyl }-malonamide (71);
3-{4-[4-(2-Benzo[1,3]dioxol-5-yl-1-dimethylcarbamoyl-vinyl)-phenoxy]-phenyl}-propionic acid ethyl ester (69);

3-Benzo[1,3]dioxol-5-yl-2-{4-[4-(2-carbamoylethyl)-phenoxy]-phenyl}-N,N-dimethyl-acrylamide (72);

N,N-Dimethyl-2-{4-[4-(3-oxo-3-ureidopropyl)-phenoxy]-phenyl}-3-pyridin-3-yl-acrylamide (73);

2-{4-[4-(2-Carbamoyl-ethyl)-phenoxy]-phenyl}-N,N-dimethyl-3-pyridin-3-yl-acrylamide (77).

The following are more preferred compounds for their antidiabetic properties:

3-(3,5-Dimethoxyphenyl)-2-{4-[4-(3-ethoxycarbonylamino-3-oxo-propyl)-phenoxy]-phenyl}-acrylic acid methyl ester (8);

(4-{4-[2-(3,5-Dimethoxyphenyl)-1-dimethylcarbamoyl-vinyl]-phenoxy}-benzyl)-carbamic acid methyl ester (29);

2-{4-[4-(2-Carbamoylethyl)-phenoxy]-phenyl}-3-(3,5-dimethoxyphenyl)-N,N-dimethylacrylamide (31);

3-(3,5-Dimethoxyphenyl)-N,N-dimethyl-2-{4-[4-(3-morpholin-4-yl-3-oxopropyl)-phenoxy]phenyl}-acrylamide (40);

[3-(4-{4-[2-(3,5-Dimethoxyphenyl)-1-(piperidine-1-carbonyl)-vinyl]-phenoxy}-phenyl)-propionyl]-urea (51);

2-{4-[4-(3-Acetylamino-3-oxopropyl)-phenoxy]-phenyl}-3-(4-fluorophenyl)-N,N-dimethylacrylamide (56);

3-(3,5-Dimethoxyphenyl)-2-{4-[4-(3-oxo-3-ureidopropyl)-phenoxy]-phenyl}-N-pyridin-4-ylacrylamide (60);

N-(4-Chlorophenyl)-3-(3,5-dimethoxyphenyl)-2-{4-[4-(3-oxo-3-ureidopropyl)-phenoxy]-phenyl}-acrylamide (61);

3-(3,5-Dimethoxyphenyl)-N,N-dimethyl-2-(4-{4-[2-(2-morpholin-4-yl-2-oxoethylcarbamoyl)-ethyl]-phenoxy}-phenyl)-acrylamide (63);

3-(3,5-Dimethoxyphenyl)-N,N-dimethyl-2-(4-{4-[3-(4-methylpiperazin-1-yl)-3-oxopropyl]-phenoxy}-phenyl)-acrylamide (64).

However, it will be appreciated that the invention also contemplates the provision and use of other compounds according to Formulas I-XIII.

The compounds according to the present invention may be combined with a physiologically acceptable carrier or vehicle to provide a pharmaceutical composition, such as, lyophilized powder in the form of tablet or capsule with various fillers and binders. Similarly, the compounds may be coadministered with other agents. Co-administration shall mean the administration of at least two agents to a subject so as to provide the beneficial effects of the combination of both agents. For example, the agents may be administered simultaneously or sequentially over a period of time. The effective dosage of a compound in the composition can be widely varied as selected by those of ordinary skill in the art and may be empirically determined. Moreover, the compounds of the present invention can be used alone or in combination with one or more additional agents depending on the indication and the desired therapeutic effect. For example, in the case of diabetes, insulin resistance and associated conditions or complications, including obesity and hyperlipidemia, such additional agent(s) may be selected from the group consisting of: insulin or an insulin mimetic, a sulfonylurea (such as acetohexamide, chlorpropamide, glimepiride, glipizide, glyburide, tolbutamide and the like) or other insulin secretagogue (such as nateglinide, repaglinide and the like), a thiazolidinedione (such as pioglitazone, rosiglitazone and the like) or other peroxisome proliferator-activated receptor (PPAR)-gamma agonist, a fibrate (such as bezafibrate, clofibrate, fenofibrate, gemfibrozol and the like) or other PPAR-alpha agonist, a PPAR-delta agonist, a biguanide (such as metformin), a statin (such as fluvastatin, lovastatin, pravastatin, simvastatin and the like) or other hydroxymethylglutaryl (HMG) CoA reductase inhibitor, an alpha-glucosidase inhibitor (such as acarbose, miglitol, voglibose and the like), a bile acid-binding resin (such as cholestyramine, celestipol and the like), a high density lipoprotein (HDL)-lowering agent such as apolipoprotein A-I (apoA1), niacin and the like, probucol and nicotinic acid, Preferred additional agents include, for example, sulfonylurea, thiazolidinedione, fibrate or statin, preferably sulfonylurea.

In the case of inflammation, inflammatory diseases, autoimmune disease and other such cytokine mediated disorders, the additional agent(s) may be selected from the group consisting of: a nonsteroidal anti-inflammatory drug (NSAID) (such as diclofenac, diflunisal, ibuprofen, naproxen and the like), a cyclooxygenase-2 inhibitor (such as celecoxib, rofecoxib and the like), a corticosteroid (such as prednisone, methylprednisone and the like) or other immunosuppressive agent (such as methotrexate, leflunomide, cyclophosphamide, azathioprine and the like), a disease-modifying antirheumatic drug (DMARD) (such as injectable gold, penicilliamine, hydroxychloroquine, sulfasalazine and the like), a TNF-alpha inhibitor (such as etanercept, infliximab and the like), other cytokine inhibitor (such as soluble cytokine receptor, anti-cytokine antibody and the like), other immune modulating agent (such as cyclosporin, tacrolimus, rapamycin and the like) and a narcotic agent (such as hydrocodone, morphine, codeine, tramadol and the like).

Preferred diseases that may be treated by the preferred methods include inflammatory or immunological disease, for example, rheumatoid arthritis, osteoarthritis, ankylosing spondylitis, psoriasis, psoriatic arthritis, asthma, acute respiratory distress syndrome, chronic obstructive pulmonary disease, or multiple sclerosis. Additional preferred diseases that may be treated by the preferred methods include diabetes, hyperlipidemia, includes coronary heart disease, cancer or proliferative disease.

Another aspect of the invention is a method of treating diabetes and related diseases comprising the step of administering to a subject suffering from a diabetic or related condition a therapeutically effective amount of a compound of Formulas I-XIII. Additionally, the invention provides a method of treating inflammation or inflammatory diseases or diseases mediated by cytokines, PDE4, PDE3, p44/42 MAP kinase, iNOS and/or COX-2 by administering to a subject in need of such treatment an effective amount of a compound according to Formulas I-XIII. Further, pharmaceutical compositions containing a therapeutically effective amount of one or more compounds according to Formulas I-XIII together with a pharmaceutically or physiologically acceptable carrier, for use in the treatments contemplated herein, are also provided.

A preferred method of the present invention, therefore, provides for inhibiting the activity of TNF-alpha, IL-1, IL-6, PDE4, PDE3, p44/42 MAP kinase, iNOS or COX-2 comprising administering to a host at least one preferred pharmaceutical composition as described above. Likewise, a preferred method of the present invention provides for inhibiting the undesired action of cytokine, phosphodiesterase, MAP kinase or cyclooxygenase comprising administering to a host at least one pharmaceutical composition as described above.

The compounds of the invention are useful for the treatment of diabetes, characterized by the presence of elevated blood glucose levels, that is, hyperglycemic disorders such as diabetes mellitus, including both type 1 and 2 diabetes, as well as other hyperglycemic related disorders such as obesity, increased cholesterol, hyperlipidemia such as hypertriglyceridemia, kidney related disorders and the like. The compounds are also useful for the treatment of disorders linked to insulin resistance and/or hyperinsulinemia, which include, in addition to diabetes, hyperandrogenic conditions such as polycystic ovary syndrome (Ibanez et al., J. Clin Endocrinol Metab, 85:3526-30, 2000; Taylor A. E., Obstet Gynecol Clin North Am, 27:583-95, 2000), coronary artery disease such as atherosclerosis and vascular restenosis, and peripheral vascular disease. Additionally, the compounds of the present invention are also useful for the treatment of inflammation and immunological diseases that include those mediated by signaling pathways linked to pro-inflammatory cytokines, such as rheumatoid arthritis, ankylosing spondylitis, multiple sclerosis, inflammatory bowel disease, psoriasis, and contact and atopic dermatitis.

By "treatment", it is meant that the compounds of the invention are administered in an amount which is at least sufficient to, for example, reduce the blood glucose level in a patient suffering from a hyperglycemic disorder or to inhibit or prevent the development of pro-inflammatory cytokine or like responses in a patient suffering from inflammatory or immunological disease. In the case of diabetes, the compound is usually administered in the amount sufficient to reduce the blood glucose level, free fatty acid level, triglyceride level and/or the like level sufficient to improve or alleviate the symptoms and/or reduce the risk of complications associated with elevated levels of these parameters. A variety of subjects may be treated with the present compounds to reduce blood glucose levels such as livestock, wild or rare animals, pets, as well as humans. The compounds may be administered to a subject suffering from hyperglycemic disorder using any convenient administration technique, including intravenous, intradermal, intramuscular, subcutaneous, oral and the like. However, oral daily dosage is preferred. The dosage delivered to the host will necessarily depend upon the route by which the compound is delivered, but generally ranges from about 0.1 to about 500 mg/kg human body weight or typically from about 0.1 to about 50 mg/kg human body weight. Generally similar types of administration and dosages are also contemplated when the compounds of the invention are used to treat inflammatory or immunological disease.

The compounds of this invention may be used in formulations using acceptable pharmaceutical vehicles for enteral, or parenteral, administration, such as, for example, water, alcohol, gelatin, gum arabic, lactose, amylase, magnesium stearate, talc, vegetable oils, polyalkylene glycol, and the like. The compounds can be formulated in solid form, e.g., as tablets, capsules, drages and suppositories, or in the liquid form, e.g., solutions, suspensions and emulsions. The preparations may also be delivered transdermally or by topical application.

The syntheses of representative compounds according to the present invention are illustrated in Schemes I and II. Further examples illustrating the syntheses of additional compounds according to the present invention are also given below.

SCHEME I

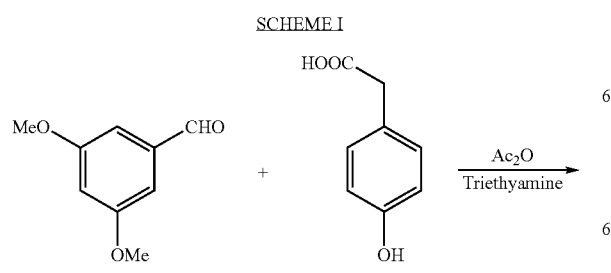

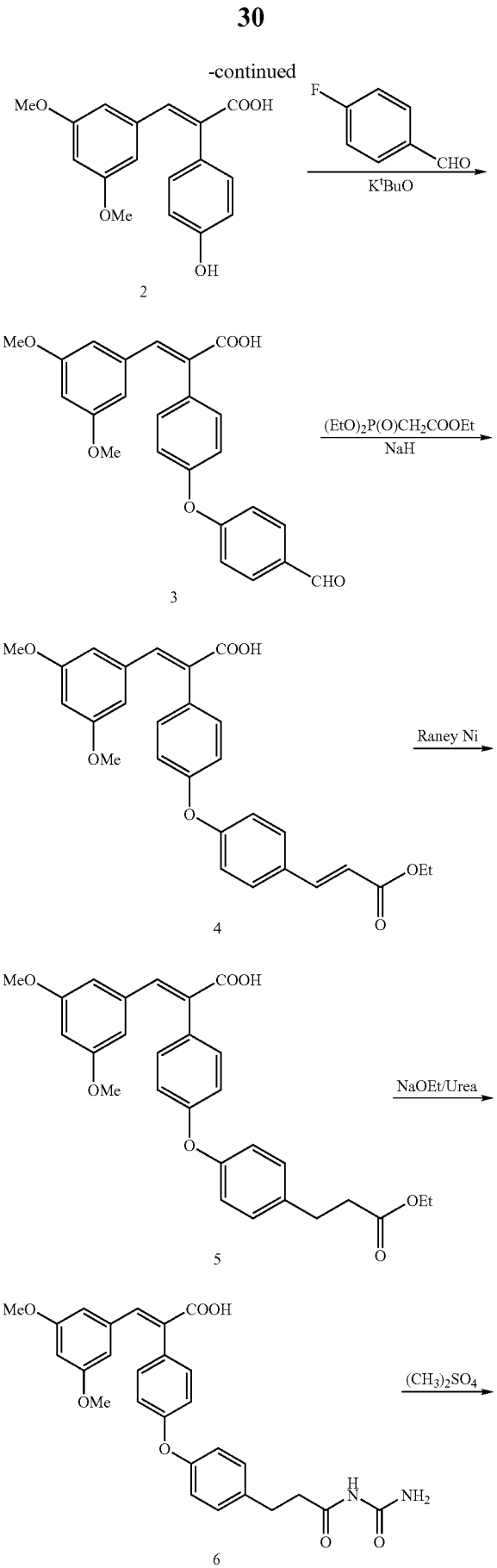

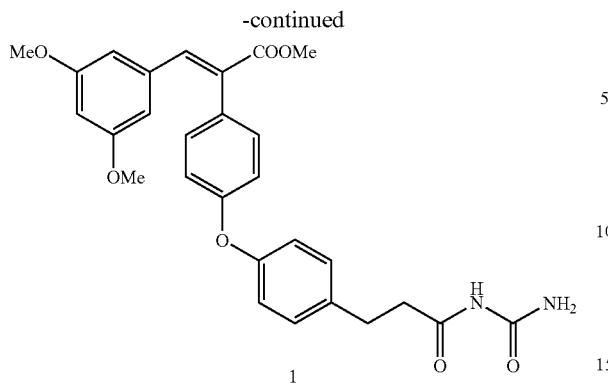

1

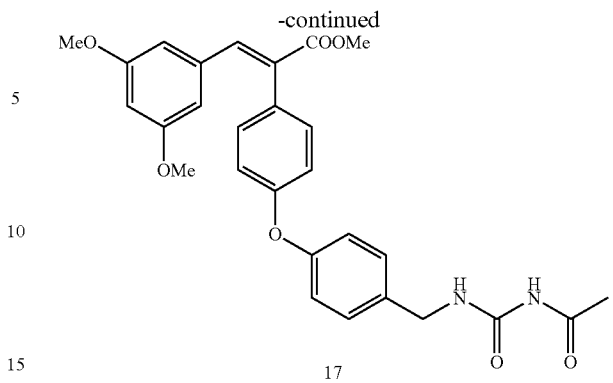

17

Scheme 1 details the synthesis of compounds 1-6. Scheme 2 details the synthesis of 17. It is to be understood that the Schemes 1 and 2 are representative schemes and are not intended to be limited to the compounds disclosed.

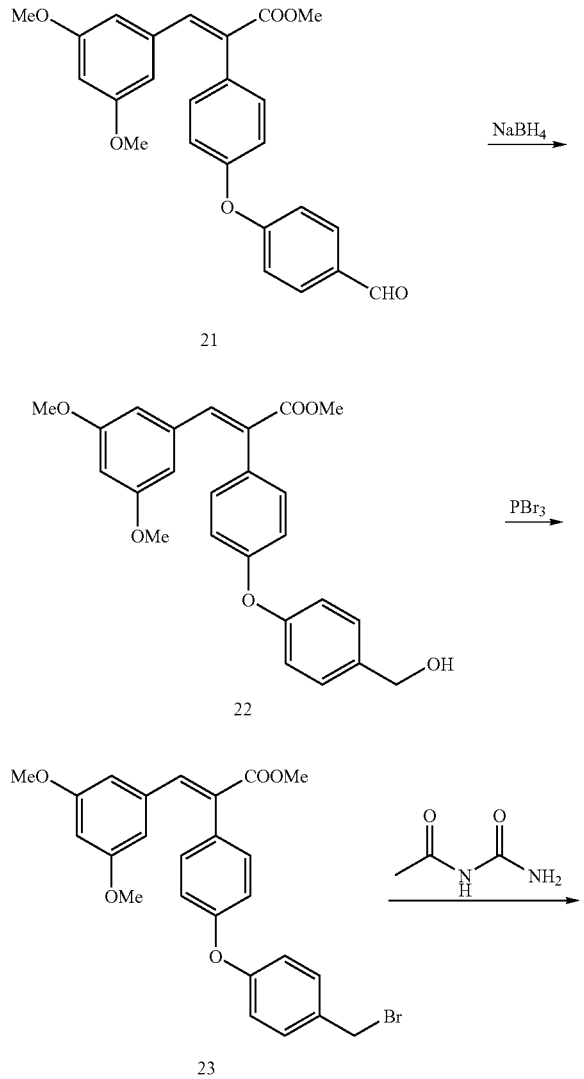

EXAMPLES

The following examples are provided to further illustrate the present invention and are not intended to limit the invention in any way.

Example 1

Synthesis of 3-(3,5-dimethoxyphenyl)-2-{4-[4-(3-oxo-3-ureidopropyl)-phenoxy]-phenyl}-acrylyc acid methyl ester (1) [see Scheme I]

Step 1: Synthesis of 3-(3 5-dimethoxyphenyl)-2-(4-hydroxyphenyl)-acrylic acid (2). To a mixture of 3,5-dimethoxybenzaldehyde (120 g, 0.72 mol) and p-hydroxyphenyl acetic acid (110 g, 0.72 mol) was added acetic anhydride (240 mL) and triethylamine (161 mL, 1.6 equiv.). This non-homogeneous mixture on heating becomes homogeneous at ~70° C. After being stirred at 130° C. for 4 hr, the mixture was cooled to room temperature. HCl (15%, 500 mL) was added to the reaction mixture slowly in 30 min keeping temperature below 5-10° C. The solid was dissolved in 3N aqueous NaOH (1.2 L) and stirred for 0.5 hr. The filtrate was acidified, maintaining a temperature at 25-30° C., with conc. HCl (~700 mL) to pH 1. The precipitated product was filtered and washed with water to give crude product (~300 g, wet cake). The crude product was dissolved by heating in ethanol and recrystallized by adding equal volume of water. The product was dried overnight in a vacuum oven at 40° C. Yield: 161 g, 74%. Analysis: $^1$HNMR (DMSO-$d_6$): δ 12.48 (br, 1H), 9.42 (s, 1H), 7.59 (s, 1H), 6.95 (d, J=8.0 Hz, 2H), 6.76 (d, J=8.0 Hz, 2H), 6.35 (t, J=2.2 Hz, 1H), 6.27 (d, J=2.2 Hz, 2H), 3.56 (s, 6H).

(b) Step 2: Synthesis of 3-(3,5-dimethoxyphenyl)-2-[4-(4-formylphenoxy)-phenyl]-acrylic acid (3). 2 (64.0 g, 0.21 mol) was dissolved in 320 mL anhydrous DMSO under nitrogen, and potassium tert-butoxide (48.0 g, 0.43 mol) was added in lots. When the solution became homogenous, p-fluorobenzaldehyde (27 mL, 0.22 mol) was added and the mixture was heated at 100° C. for 5 hr. After cooling to room temperature, the solution was poured into 1 L water and extracted with ether (2×500 mL). The aqueous phase was acidified with 5% HCl to ~pH 4 and the precipitated product was collected by suction filtration. The wet filter cake was dissolved in a minimum of boiling acetone and recrystallized with addition of water. After chilling to 4° C. for 3 hr, the solid was collected by vacuum filtration. The product was dried overnight at 40° C. in a vacuum oven. Yield: 62 g, 73%. Analysis: $^1$HNMR (DMSO-$d_6$): δ 12.87 (s, 1H), 9.94 (s, 1H), 7.95 (d, J=8.2 Hz, 2H), 7.72 (s, 1H), 7.27 (d, J=8.0 Hz, 2H), 7.19 (d, J=8.0 Hz, 2H), 7.15 (d, J=8.2 Hz, 2H), 6.42 (t, J=1.6 Hz, 1H), 6.29 (d, J=2.0 Hz, 2H), 3.60 (s, 6H).

(c) Step 3: Synthesis of 3-(3,5-dimethoxyphenyl)-2-{4-[4-(2-ethoxycarbonyl-vinyl)-phenoxy]-phenyl}-acrylic acid (4). Triethylphosphonoacetate (7.14 mL, 36 mmol) was added to a suspension of NaH (60% in mineral oil, 2.64 g, 66 mmol) in anhydrous THF (100 mL) at 0° C. under argon, and the mixture was stirred for 15 min. A solution of aldehyde 3, (12.12 g, 30 mmol) in THF (100 mL) was added and the mixture was stirred for 1 h. The mixture was quenched with saturated aqueous ammonium chloride solution (5 mL), diluted with ethyl acetate (300 mL) and acidified with 5% aqueous HCl to pH 1. The ethyl acetate layer was separated, and the aqueous layer was extracted with ethyl acetate (100 mL). The combined organic layers were washed with brine, dried over anhydrous MgSO$_4$, filtered and concentrated. The crude product was purified by recrystallization from a mixture of chloroform/methanol. The compound was suspended in hot methanol (200 mL) and a minimum volume (~30-40 mL) of chloroform was added to yield 4. Yield: 12.39 g, 87.1%. Analysis: $^1$HNMR (DMSO-d$_6$): δ 7.77 (d, J=8.4 Hz, 2H), 7.69 (s.1H), 7.65 (d, J=16 Hz, 2H), 7.23 (d, 8.8 Hz, 2H), 7.11 (d, J=8.8 Hz, 2H), 7.01 (d, J=8.4 Hz, 2H), 6.57 (d, J=16 Hz, 2H), 6.41 (t, J=2 Hz, 1H), 6.28 (d, J=1.6 Hz, 2H), 4.18 (q, J=7.2 Hz, 2H), 3.59 (s, 6H), 1.26 (t, J=7.2 Hz, 3H).

(d) Step 4: Synthesis of 3-(3,5-dimethoxyphenyl)-2-{4-[4-(2-ethoxycarbonyl-ethyl)-phenoxy]-phenyl}-acrylic acid (5). To a suspension of Raney Ni (10.0 g, Raney 2800 nickel in water active catalyst) in ethanol-dioxane (2:1, 50 mL) was added a solution of 4 (13.0 g, 27.4 mmol) in a mixture of ethanol-dioxane (2:1, 400 mL), and the resulting mixture was stirred vigorously for 15 hr under hydrogen at atmospheric pressure. Completion of the reaction was monitored by HPLC (time varies with the speed of stirring). Catalyst was filtered through a bed of Celite® diatomaceous earth, the bed was washed with ethanol-dioxane (2:1, 200 mL), and solvent was evaporated. The solid obtained was dissolved in hot toluene (150 mL) and cooled at 4° C. overnight. Solid separated was filtered and washed with ice-cold toluene (50 mL) and dried at 55° C. for 6 hr. Yield: 11.61 g, 90.5%. Analysis: $^1$HNMR (DMSO-d$_6$): δ 12.75 (s, 1H), 7.68 (s, 1H), 7.26 (d, J=8.4 Hz, 2H), 7.17 (d, J=8.4 Hz, 2H), 6.99 (d, J=8.4 Hz, 2H), 6.94 (d, J=8.4 Hz, 2H), 6.39 (t, J=2.0 Hz, 1H), 6.27 (d, J=1.6 Hz, 2H), 4.06 (q, J=7.2 Hz, 2H), 3.57 (s, 6H), 2.84 (t, J=8 Hz, 2H), 2.60 (t, J=8 Hz, 2H), 1.15 (t, J=8 Hz, 3H).

(e) Step 5: Synthesis of 3-(3,5-dimethoxyphenyl)-2-{4-[4-(3-oxo-3-ureido -propyl)-phenoxy]-phenyl}-acrylic acid (6). To a solution of sodium ethoxide in ethanol (21% w/w, 65 mL) under argon was added ethyl acetate (3.12 mL), then refluxed for 20 min. Urea (18 g, 0.3 mol) was dissolved in the above-mentioned sodium ethoxide in ethanol solution at 75° C. To this solution was added 5 (13 g, 0.027 mol) in one lot. After all dissolved, the resulting mixture was stirred at 75° C. for another 5 min, cooled quickly in 15 min to 15-20° C., TFA (13 mL) added, and then adjusted to pH 4-5 with 5% HCl. After stirring at room temperature for 1 hr, the mixture was slowly added to water (520 mL). The solid separated was filtered and refluxed in 10% isopropanol in ethyl acetate (150 mL) for 20 min. The mixture was allowed to cool to room temperature, then incubated overnight at 4° C. The mixture was filtered and solid was dried. Yield: 8.5 g. Analysis: $^1$HNMR (DMSO-d$_6$): δ 12.35 (br, 1H), 10.20 (s, 1H), 7.75 (br, 1H), 7.68 (s, 1H), 7.26 (d, J=8.4 Hz, 2H), 7.17 (d, J=8.4 Hz, 2H), 6.99 (d, J8.4 Hz, 2H), 6.94 (d, J=8.4 Hz, 2H), 6.39 (t, J=2.4 Hz, 1H), 6.27 (d, J=2.4 Hz, 2H), 3.57 (s, 6H), 2.81 (t, J=7.2 Hz, 2), 2.54 (t, J=7.2 Hz, 2H).

(f) Step 6: Synthesis of 3-(3,5-dimethoxyphenyl)-2-{4-[4-(3-oxo-3-ureido -propyl)-phenoxy]-phenyl}acrylic acid methyl ester (1). To a stirred solution of 6 (5 g, 0.01 mol) in dry DMF (35 mL) under argon was added K$_2$CO$_3$ (1.38 g, 0.01 mol). To this, dimethyl sulfate (3.8 g, 0.03 mol) was added and stirred at room temperature for 30 min. The reaction mixture was acidified with 5% aqueous HCl and extracted with ethyl acetate. The organic layer was dried over anhydrous magnesium sulfate and evaporated. The oily residue was dissolved in hexane/ethyl acetate (2:3, 30 mL) with stirring, and incubated overnight at 4° C. for crystallization. The solid was collected by vacuum filtration and dried. Yield: 3.3 g, 65%. Analysis: $^1$HNMR (DMSO-d$_6$): δ 10.17 (br, 1H), 7.72 (br, 2H), 7.72 (s, 1H), 7.25 (d, J=8.4 Hz, 2H), 7.18 (d, J=6.8 Hz, 2H), 7.21 (s overlapped, 1H), 7.01 (d, J=6.8 Hz, 2H), 6.96 (d, J=8.4 Hz, 2H), 6.41 (t, J=2.2 Hz, 1H), 6.28 (d, J=2.2 Hz, 2H), 3.73 (s, 3H), 3.57 (s, 6H), 2.84 (t, J=7.2 Hz, 2H), 2.61 (t, J=7.2 Hz, 2H).

Example 2

Synthesis of 3-(3,5-dimethoxyphenyl)-2-{4-[4-(3-ethoxycarbonylamino-3-oxo-propyl)-phenoxy]-phenyl}-acrylic acid methyl ester (8)

2-{4-[4-(2-Carbamoyl-ethyl)-phenoxy]-phenyl}-3-(3,5-dimethoxyphenyl)-acrylic acid methyl ester (7) was obtained as a byproduct in the synthesis of 3-(3,5-dimethoxy-phenyl)-2-{4-[4-(2,4-dioxothiazolidin-5-ylmethyl)-phenoxy]-phenyl}-acrylic acid methyl ester, performed essentially as shown in PCT/US99/09982 (WO 99/58127). 7 (460 mg, 1.0 mmol) was taken up in dry THF (6 mL) and cooled to −78° C. To this solution, lithium diisopropyl amide (LDA) (2M, 0.55 mL, 1.1 mmol) was added and stirred for 10 min. Ethyl chloroformate (0.11 mL, 1.2 mmol) was added and stirred overnight at room temperature. The reaction was quenched with saturated aqueous ammonium chloride solution and ethyl acetate (50 mL) was added. The organic layer was washed with brine (2×20 mL), dried on anhydrous magnesium sulfate and evaporated under reduced pressure. The crude product was purified by silica gel chromatography and eluted with hexane-ethyl acetate (7:3). Yield: 264 mg, 49.8%.

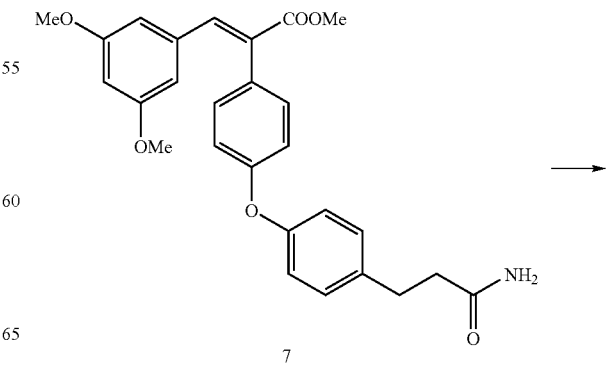

7

-continued

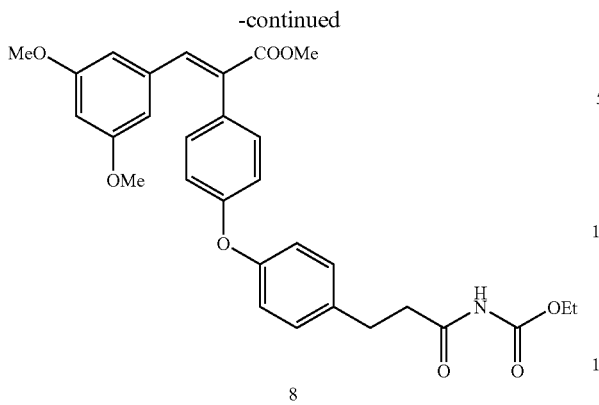

8

Analysis: ¹HNMR (DMSO-d₆): δ 10.52 (s, 1H), 7.70 (s, 1H), 7.24 (d, J=8.4 Hz, 2H), 7.17 (d, J=8.4 Hz, 2H), 6.99 (d, J=8.4 Hz, 2H), 6.94 (d, J=8.4 Hz, 2H), 6.40 (t, J=2.1 Hz, 1H), 6.27 (d, J=2.1 Hz, 2H), 4.07 (q, J=7.2 Hz, 2H), 3.70 (s, 3H), 3.56 (s, 6H), 2.76 (m, 4H), 1.19 (t, J=7.2 Hz, 3H).

Example 3

Synthesis of 2-{4-[4-(3-benzoyloxycarbonylamino-3-oxo-propyl)-phenoxy]-phenyl}-3-(3,5-dimethoxyphenyl)-acrylic acid methyl ester (9)

7 (1.38, 3.0 mmol) prepared as in Example 2 was taken up in dry THF (20 mL) and cooled to −78° C. To this solution, LDA (2M, 1.8 mL, 3.6 mmol) was added and stirred for 10 min. Benzyl chloroformate (0.67 g, 39 mmol) was added and stirred overnight at room temperature. The reaction was quenched with saturated aqueous ammonium chloride solution, and ethyl acetate (150 mL) was added. The organic layer was washed with brine (2×25 mL), dried on anhydrous magnesium sulfate and evaporated under reduced pressure. The crude product was purified by silica gel chromatography and eluted with hexane-ethyl acetate (7:3). Yield: 0.68 g, 37.3%.

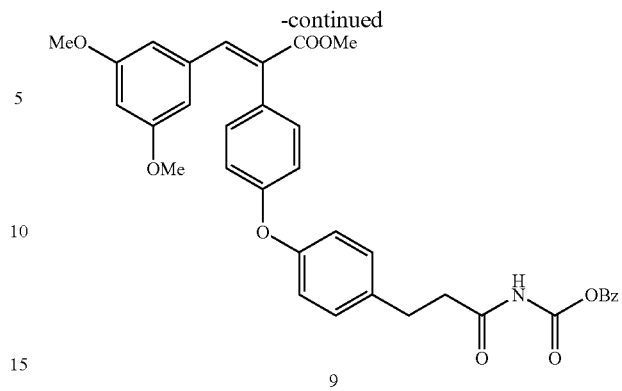

9

Analysis: ¹HNMR (DMSO-d₆): δ 10.65 (s, 1H), 7.72 (s, 1H), 7.38-7.39 (m, 5H), 7.25 (d, J=8.4 Hz, 2H), 7.18 (d, J=8.4 Hz, 2H), 7.00 (d, J=8.4 Hz, 2H), 6.94 (d, J=8.4 Hz, 2H), 6.41 (t, J=2.0 Hz, 1H), 6.28 (d, J=2.0 Hz, 2H), 5.12 (s, 2H), 3.72 (s, 3H), 3.57 (s, 6H), 2.79 (m, 4H).

Example 4

Synthesis of 3-(3,5-dimethoxyphenyl)-2-{4-[4-(3-oxo-3-ureidopropyl)-phenoxy]-phenyl}-propionic acid (10)

3-(3,5-Dimethoxyphenyl)-2-{4-[4-(2-ethoxycarbonylvinyl)-phenoxy]-phenyl}-acrylic acid (4, 2.37 g, 5.0 mmol) was dissolved in a mixture of ethanol-dioxane (2:1, 150 mL), and palladium charcoal (10%, 500 mg) was added. The mixture was stirred under hydrogen for 15 hr. Catalyst was then removed by filtration, and solvent was evaporated under reduced pressure to yield 3-(3,5-dimethoxy-phenyl)-2-{4-[4-(2-ethoxycarbonylethyl)-phenoxy]-phenyl}-propionic acid (18) quantitatively. Urea (0.21 g, 3.58 mmol) was dissolved in sodium ethoxide (2.7 M, 2.2 mL, 5.92 mmol) at 80° C. under argon, and to this a solution of 18 (1.13 g, 2.37 mmol) in anhydrous ethanol (15 mL) was added and heated at this temperature for 13 hr. Ethanol was evaporated under reduced pressure, water (20 mL) was added, acidified to pH 1 by 5% aqueous HCl and extracted with ethyl acetate (50 mL). The organic layer was washed with water (2×25 mL), brine (2×20 mL), dried over anhydrous magnesium sulfate and evaporated. The crude product was purified by silica gel chromatography and eluted with hexane-ethyl acetate (3:7) containing acetic acid (1%), followed by recrystallization from ethanol. Yield: 256 mg, 22.8%.

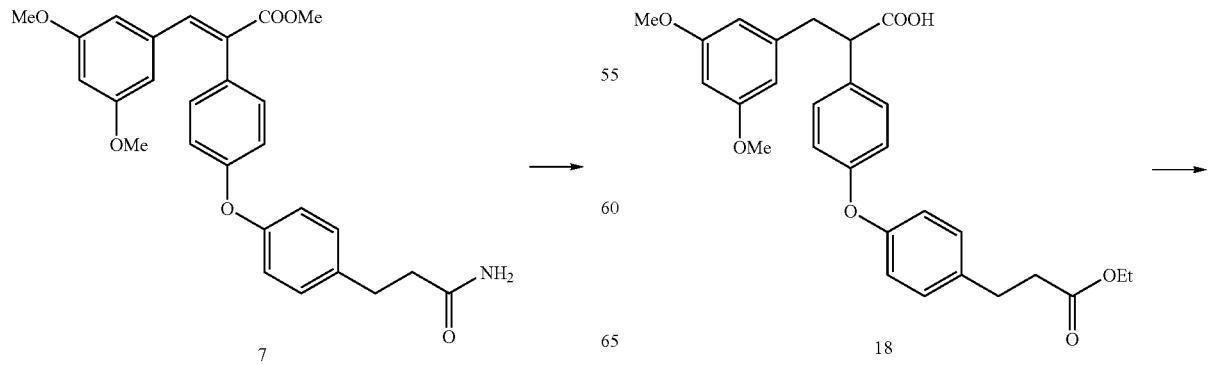

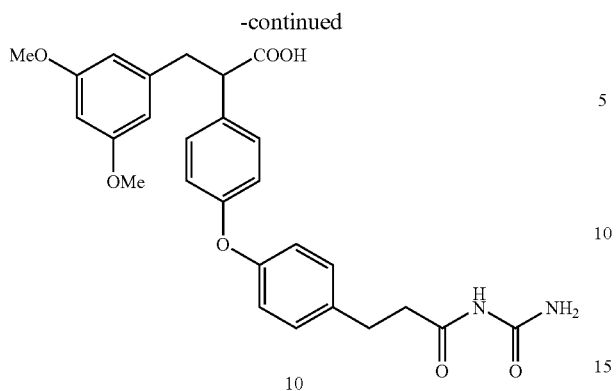

Analysis: ¹HNMR (DMSO-d$_6$): δ 12.37 (s, 1H), 10.17 (s, 1H), 7.74 (br, 1H), 7.31 (d, J=9.2 Hz, 2H), 7.21 (d, J=9.2 Hz, 2H), 6.91 (d, J=8.4 Hz, 2H), 6.90 (d, J=8.4 Hz, 2H), 6.33 (d, J=2.0 Hz, 2H), 6.29 (t, J=2.0 Hz, 1H), 3.83 (t, J=8.0 Hz, 1H), 3.68 (s, 6H), 3.19 (dd, J=14.4 & 8.4 Hz, 1H), 2.88-2.80 (m, 3H), 2.59 (t, J=8.0 Hz, 2H).

Example 5

Synthesis of 3-(3,5-dimethoxyphenyl)-2-{4-[4-(3-oxo-3-ureidopropenyl)-phenoxy]-phenyl}-acrylic acid (11)

Urea (0.21 g, 3.58 mmol) was dissolved in sodium ethoxide (2.7 M, 2.2 mL, 5.92 mmol) at 80° C. under argon, and to this a solution of 4 (1.14 g, 2.37 mmol) in anhydrous ethanol (15 mL) was added and heated at this temperature for 13 hr. Ethanol was evaporated under reduced pressure, water (20 mL) was added, acidified to pH 1 by 5% aqueous HCl and extracted with ethyl acetate (50 mL). The organic layer was washed with water (2×25 mL), brine (2×20 mL), dried over anhydrous magnesium sulfate and evaporated. The crude product was purified by silica gel chromatography and eluted with hexane-ethyl acetate (3:7) containing acetic acid (1%), followed by recrystallization from ethanol. Yield: 167 mg, 14.4%.

Analysis: ¹HNMR (DMSO-d$_6$): δ 12.51 (br, 1H), 10.30 (s, 1H), 7.92 (br, 1H), 7.77 (d, J=9.2 Hz, 2H), 7.68 (s, 1H), 7.65 (d, J=16.0 Hz, 1H), 7.30 (br, 1H), 7.22 (d, J=8.8 Hz, 2H), 7.10 (d, J=8.8 Hz, 2H), 7.03 (d, J=9.2 Hz, 2H), 6.73 (d, J=16.0 Hz, 1H), 6.40 (t, J=2.0 Hz, 1H), 6.28 (d, J=2 Hz, 2H), 3.59 (s, 6H).

Example 6

Synthesis of 3-(3,5-dimethoxyphenyl)-2-{4-[4-(3-oxo-3-ureidopropyl)-phenoxy]-phenyl}-acrylic acid ethyl ester (12)

To a stirred solution of 6 (0.40 g, 0.81 mmol) in dry DMSO (3 mL) was added K$_2$CO$_3$ (0.14 g, 0.98 mmol). To this, diethyl sulfate (0.115 g, 0.91 mmol) was added and stirred at room temperature for 30 min. The reaction mixture was poured into water (30 mL) and extracted with ethyl acetate. The organic layer was dried over anhydrous magnesium sulfate and evaporated. The crude product was purified by column chromatography over silica gel and eluted with hexanes-ethyl acetate (3:1). Yield: 0.39 g, 92.2%.

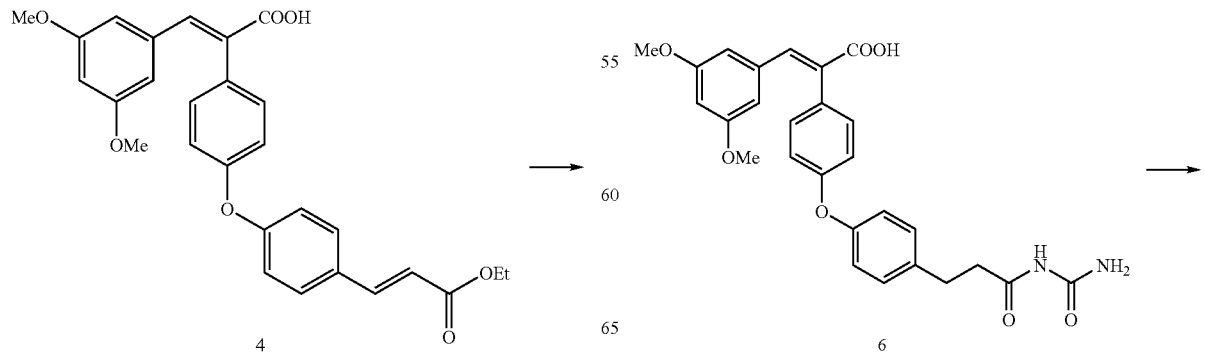

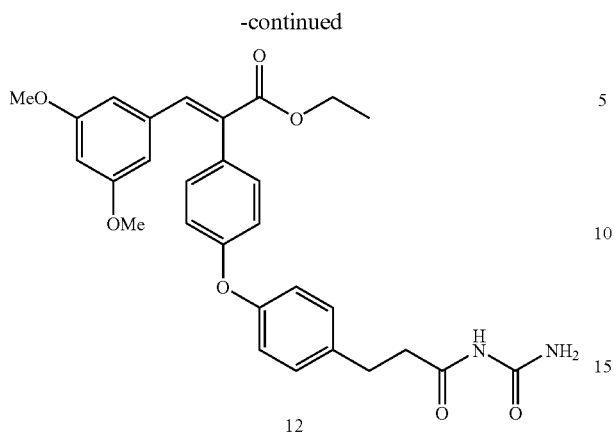

12

Analysis: ¹HNMR (DMSO-d$_6$): δ 10.17 (s, 1H), 7.74 (br, 1H), 7.70 (s, 1H), 7.25 (d, J=8.4 Hz, 2H), 7.24 (overlapped, 1H), 7.18 (d, J=8.4 Hz, 2H), 7.00 (d, J=8.4 Hz, 2H), 6.95 (d, J=8.4 Hz, 2H), 6.41 (t, J=1.6 Hz, 1H), 6.28 (d, J=1.6 Hz, 2H), 4.19 (q, J=8.0 Hz, 2H), 3.57 (s, 6H), 2.83 (t, J=7.2 Hz, 2H), 2.60 (t, J=7.2 Hz, 2H), 1.25 (t, J=8.0 Hz, 3H).

Example 7

Synthesis of 3-(3,5-dimethoxyphenyl)-N,N-dimethyl-2-{4-[4-(3-oxo-3-ureido-propyl)-phenoxy]-phenyl}-acrylamide (13)

To a stirred solution of 6 (1.68 g, 3.43 mmol) in dry DMF (30 mL) was added carbonyldiimidazole (1.1 g, 6.86 mmol), and the reaction mixture was heated to 60° C. for 1 hr. The reaction mixture was cooled to 0° C. and a solution of dimethylamine in THF (2 M, 8.6 mL, 17.2 mmol) was added and stirred for 18 hr. The reaction mixture was diluted with water (100 mL) and extracted with ethyl acetate (100 mL). The organic phase was then rinsed sequentially with 10% citric acid (2×50 mL), water (2×50 mL), and brine (20 mL), then dried over anhydrous magnesium sulfate and evaporated. The crude product was purified by silica gel chromatography using hexane-ethyl acetate (3:7) containing 1% acetic acid. Yield: 1.77 g, 100%.

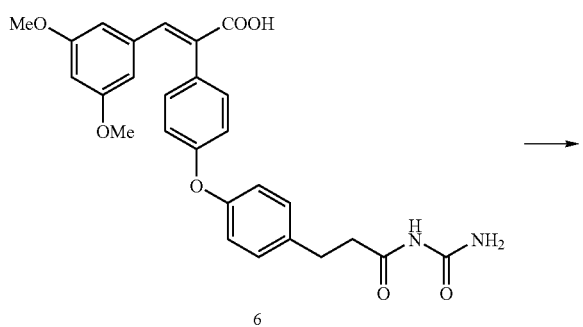

6

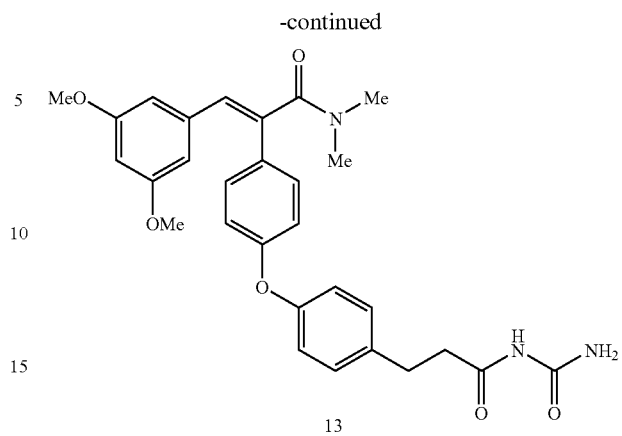

13

Analysis: ¹HNMR (DMSO-d6): δ 10.17 (br, 1H), 7.74 (br, 1H), 7.27 (d, J=9.2 Hz, 2H), 7.23 (d, J=8.8 Hz, 2H), 7.23 (br, 1H), 6.79 (d, J=9.2 Hz, 2H), 6.93 (d, J=8.8 Hz, 2H), 6.56 (s, 1H), 6.34 (t, J=2 Hz, 1H), 6.29 (s, 1H), 6.28 (s, 1H), 3.58 (s, 6H), 3.05 (br, 3H), 2.90 (br, 3H), 2.82 (t, J=7.2 Hz, J=8.0 Hz, 2H), 2.59 (t, J=8.0 Hz, J=7.2 Hz, 2H).

Example 8

Synthesis of 2-(4-{4-[3-(3-cyclohexylureido)-3-oxopropyl]-phenoxy}-phenyl)-3-(3,5-dimethoxyphenyl)-acrylic acid (14)

Cyclohexylurea (1.3 g, 9 mmol) was dissolved in sodium ethoxide in ethanol (21% w/w, 3 mL) at 75° C. To this solution 5 was added (0.5 g, 1.1 mmol) in one lot. The resulting mixture was stirred at 75° C. for 5 min, then cooled quickly to 40-50° C. TFA (0.5 mL) was added and then 5% aqueous HCl (1N, 0.6 mL). After stirring at room temperature for 1 hr, the mixture was left overnight at 4° C. The solid separated was filtered and refluxed in ethyl acetate (4 mL) for 20 min. The mixture was allowed to cool to room temperature, filtered and the crude product was purified by silica gel chromatography using hexane-ethyl acetate (1:1). Yield: 0.27 g, 45%.

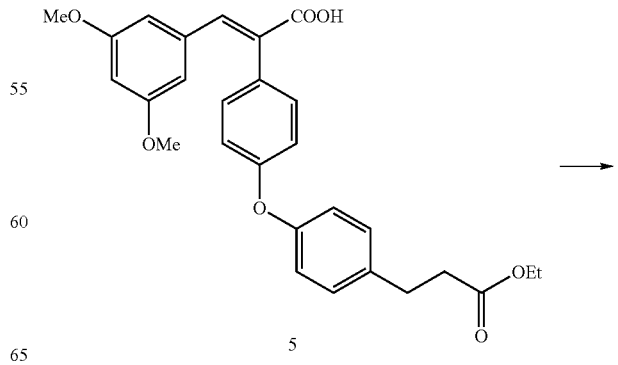

5

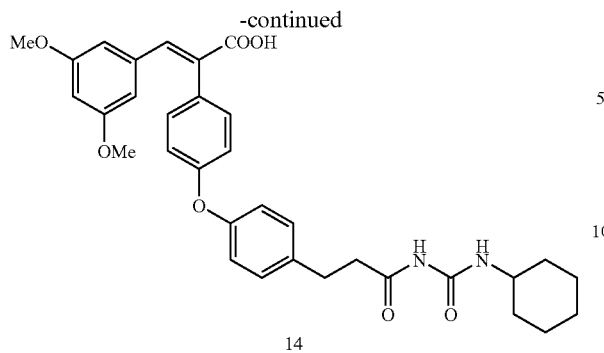

14

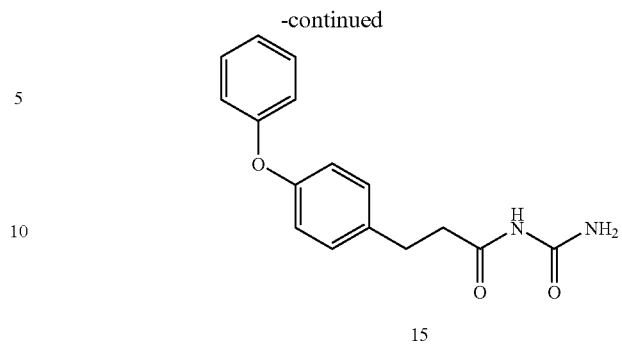

15

Analysis: ¹HNMR (DMSO-d₆): δ 12.74 (s, 1H), 10.30 (s, 1H), 8.32 (br, 1H), 7.67 (s, 1H), 7.24 (d, J=8.8 Hz, 2H), 7.16 (d, J=8.8 Hz, 2H), 6.90 (d, J=8.4 Hz, 2H), 6.94 (d, J=8.4 Hz, 2H), 6.34 (t, J=2.4 Hz, 1H), 6.27 (d, J=2.4 Hz, 2H), 3.58 (s, 6H), 2.83 (t, J=7.6 Hz, 2H), 2.59 (t, J=7.6 Hz, 2H), 1.78 (m, 2H), 1.61 (m, 2H), 1.51 (m, 1H), 1.32-1.16 (m, 5H).

Analysis: ¹HNMR (DMSO-d₆): δ 10.18 (s, 1H), 7.74 (br, 1H), 7.38 (d, J=7.6 Hz, 1H), 7.36 (d, J=7.6 Hz, 1H), 7.22 (d, J=8.8 Hz, 2H), 7.17 (t, J=7.2 Hz, 1H), 6.97 (d, J=7.2 Hz, 2H), 6.93 (d, J=8.8 Hz, 2H), 2.82 (t, J=7.2 Hz, 2H), 2.59 (t, J=7.2 Hz, 2H).

Example 10

Synthesis of 2-{4-[4-(3-acetylureidomethyl)-phenoxy]-phenyl}-3-(3,5-dimethoxyphenyl)-acrylic acid methyl ester (17) [see Scheme II]

Step 1: Synthesis of 3-(3,5-dimethoxyphenyl)-2-[4-(4-hydroxymethyl-phenoxy)-phenyl]-acrylic acid methyl ester (22). 3-(3,5-dimethoxy-phenyl)-2-[4-(4-formylphenoxy)-phenyl]-acrylic acid methyl ester (21) was first prepared by converting the corresponding free acid (3) to the methyl ester by addition of DMF, K₂CO₃ and dimethyl sulfate in a manner analogous to Example 1 (f) above. Sodium borohydride (0.125 g, 3.3 mmol) was added to a suspension of 21 (1.26 g, 3 mmol) in ethanol (20 mL) and stirred at room temperature for 1 hr. The reaction was quenched with 5% aqueous HCl, and ethanol was evaporated under reduced pressure. Residue was taken up in ethyl acetate (50 mL) and washed with brine (2×20 mL), dried over anhydrous magnesium sulfate and evaporated. The crude product was purified by silica gel chromatography and eluted with hexanes-ethyl acetate (1:1). Yield: 1.14 g, 95.0%. Analysis: ¹HNMR (DMSO-d₆): δ 7.72 (s, 1H), 7.36 (d, J=8.8 Hz, 2H), 7.19 (d, J=8.8 Hz, 2H), 7.01 (d, J=8.4 Hz, 2H), 6.99 (d, J=8.4 Hz, 2H), 6.41 (t, J=2.4 Hz, 1H), 6.28 (d, J=2.4 Hz, 2H), 5.18 (t, J=6.4 Hz, 1H), 4.49 (d, J=4.8 Hz, 2H), 3.72 (s, 3H), 3.57 (s, 6H).

Example 9

Synthesis of [3-(4-phenoxyphenyl)-propionyl]-urea (15)

4-phenoxy-benzaldehyde was reacted with triethyl phosphonoacetate to yield 3-(4-phenoxyphenyl)-acrylic acid ethyl ester, which was then reduced with H₂ using palladium-on-carbon catalyst to yield 3-(4-phenoxyphenyl)-propionic acid methyl ester (19). Urea (1.20 g, 19.99 mmol) was dissolved in sodium ethoxide (2 M, 6.7 mL, 13.4 mmol) at 80° C. under argon, and to this a solution of 19 (1.71 g, 6.67 mmol) in anhydrous ethanol (8 mL) was added and heated at this temperature for 1 hr. Ethanol was evaporated under reduced pressure, water (20 mL) was added, acidified to pH 1 by 5% aqueous HCl and extracted with ethyl acetate (50 mL). The organic layer was washed with water (2×25 mL), brine (2×20 mL), dried over anhydrous magnesium sulfate and evaporated. The crude product was purified by silica gel chromatography and eluted with hexane-ethyl acetate (1:1) containing acetic acid (1%) followed by recrystallization from ethanol. Yield: 113 mg, 5.6%.

(b) Step 2: Synthesis of 2-[4-(4-bromomethylphenoxy)-phenyl]-3-(3,5-dimethoxyphenyl)-acrylic acid methyl ester (23). To a stirred solution of 22 (1.05 g, 2.5 mmol) in dichloromethane (10 mL) at 10° C., PBr₃ (1 M, 3.75 mL) was added and stirred for 1 hr. The reaction was quenched with saturated aqueous sodium bicarbonate solution. The organic layer was washed with water (20 mL), brine (2×30 mL), dried over anhydrous magnesium sulfate and evaporated. The crude product was purified by silica gel chromatography and eluted with hexanes-ethyl acetate (4:1). Yield: 0.85 g, 70.4%. Analysis: ¹HNMR (DMSO-d₆): δ 7.73 (s, 1H), 7.49 (d, J=8.4 Hz, 2H), 7.22 (d, J=8.4 Hz, 2H), 7.07 (d, J=8.4 Hz, 2H), 7.00 (d, J=8.4 Hz, 2H), 6.42 (t, J=2.4 Hz, 1H), 6.28 (d, J=2.4 Hz, 2H), 4.74 (s, 2H), 3.73 (s, 3H), 3.58 (s, 6H).

(c) Synthesis of 2-{4-[4-(3-acetylureidomethyl)-phenoxy]-phenyl}-3-(3,5-dimethoxyphenyl)-acrylic acid methyl ester (17). To a stirred suspension of sodium hydride

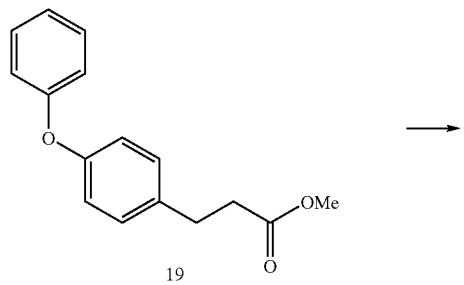

19

(60% in oil, 0.11 g, 2.8 mmol) in dimethylformamide (2 mL), N-acylurea (0.11 g, 1.12 mmol) was added and stirred at room temperature for 30 min. A solution of 23 (0.54 g, 1.12 mmol) in dimethylformamide (3 mL) was added and heated overnight at 80° C. The reaction was quenched with water and extracted with ethyl acetate (3×30 mL). The combined organic layer was washed with brine (2×25 mL), dried over anhydrous magnesium sulfate and evaporated. The crude product was purified by silica gel column chromatography and eluted with hexanes-ethyl acetate (3:7) containing 1% acetic acid. Yield: 0.16 g, 28.4%. Analysis: $^1$HNMR (DMSO-$d_6$): δ 8.34 (t, J=5.6 Hz, 1H), 7.72 (s, 1H), 7.29 (d, J=8.4 Hz, 1H), 7.19 (d, J=8.4 Hz, 2H), 7.02 (d, J=8.4 Hz, 2H), 6.99 (d, J=8.4 Hz, 2H), 6.42 (t, J=8.4 Hz, 1H), 6.28 (d, J=2.4 Hz, 2H), 4.24 (d, J=5.2 Hz), 3.73 (s, 3H), 3.57 (s, 6H), 1.87 (s, 3H).

General Procedure for Conversion of Carboxylic Acids to Amides

A mixture of carboxylic acid (1.1 mmol) and carbonyldiimidazole (1.3 mmol) in DMF (20 mL) was heated at 60° C. for 30 min. After the reaction mixture was cooled to room temperature, a solution of amine (2M, 1 mL, 2.0 mmol) was added and stirred for 18 hr. To the reaction mixture water (100 mL) was added and extracted with ethyl acetate (3×60 mL). The organic phase was washed with 10% citric acid (20 mL), water (2×50 mL), and brine (50 mL), then dried over anhydrous magnesium sulfate and removed the solvent. The crude product was purified by silica gel chromatography.

Example 11

Synthesis of N,N-dimethyl-2-{4-[4-(3-oxo-3-ureidopropyl)-phenoxy]-phenyl}-acetamide (26)

Urea (0.78 g, 13 mmol) and 3-[4-(4-carboxymethylphenoxy)-phenyl]-propionic acid ethyl ester, 24 (0.5 g, 1.5 mmol) were dissolved in sodium ethoxide in ethanol (2M, 6.5 mL, 13 mmol) at 80° C. under argon, and the reaction mixture was heated at this temperature for 1 h. The reaction was then quenched by TFA (0.5 mL) after cooling to 5° C. Water (40 mL) was added to the reaction mixture. The crude product was filtered and purified by silica gel chromatography and eluted with hexane-ethyl acetate (1:1) containing acetic acid (1%) followed by recrystallization from toluene yielded 25 (0.28 g, 54%).

Analysis: $^1$HNMR (DMSO-$d_6$): δ 12.28 (br, 1H), 7.73 (br, 1H), 7.24 (d, J=8.8 Hz, 2H), 7.23, (br, 1H), 7.21 (d, J=8.8 Hz, 2H), 6.93, (d, J=8.8 Hz, 2H), 6,92 (d, J=8.8 Hz, 2H), 3.54 (s, 2H), 2.81 (t, J=7.2 Hz, 2H), 2.58 (t, J=7.2 Hz, 2H).

Following the general procedure for conversion of carboxylic acids to amides mentioned above and using dimethyl amine as amine, 25 was converted to 26 in 97% yield.

Analysis: $^1$HNMR (DMSO-$d_6$): δ 10.17(s, 1H), 7.73 (s, 1H), 7.22 (s, 1H), 7.21 (d, J=8.0 Hz, 2H), 7.19 (d, J=8.0 Hz, 2H), 6.92 (d, J=8.0 Hz, 2H), 6.90 (d, J=8.0 Hz, 2H), 3.65 (s, 2H), 3.00 (s, 3H), 2.81 (t, J=8.0 Hz, 2H), 2.58 (t, J=8.0 Hz, 2H).

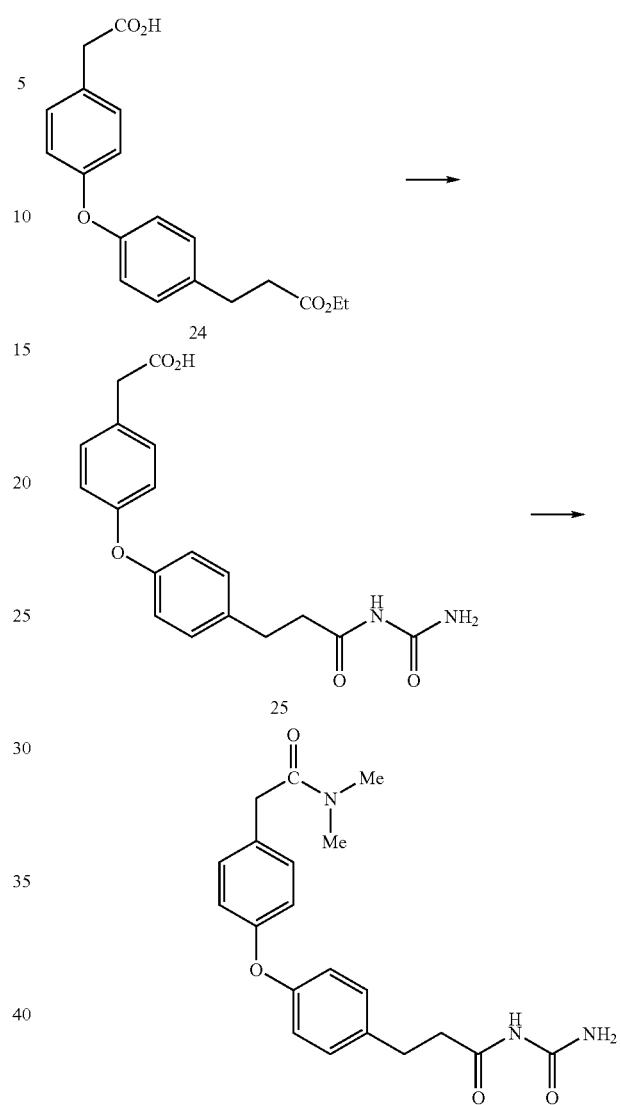

Example 12

Synthesis of (4-{4-[2-(3,5-dimethoxyphenyl)-1-dimethylcarbamoyl-vinyl]-phenoxy}-benzyl)-carbamic acid methyl ester (29)

Reaction of 3-(3,5-dimethoxyphenyl)-2-{4-[4-(2,4-dioxothiazolidin-3-ylmethyl)-phenoxy]-phenyl-}-acid, 27, (0.4 g, 0.77 mmol) with 5% LiOH (2 mL) in methanol (19 mL) was carried out at room temperature for 18 h. The reaction mixture was acidified to pH 3 by 5% aqueous HCl and extracted with ethyl acetate (2×50 mL). The organic layer was washed with water (2×50 mL), brine (2×20 mL), dried over anhydrous magnesium sulfate and evaporated. The crude product was purified by silica gel chromatography and eluted with hexane-ethyl acetate (1:1) containing acetic acid (1%). Yield (28): 0.31 g, 83%.

Analysis: $^1$HNMR (DMSO-$d_6$): δ 12.75 (br, 1H), 7.68 (t, J=4.6 Hz, 1H), 7.67 (s, 1H), 7.28 (d, J=8.8 Hz, 2H), 7.17 (d, J=8.8 Hz, 2H), 7.01 (d, J=8.8 Hz, 2H), 6.96 (d, J=8.8 Hz, 2H), 6.39 (t, J=2.8 Hz, 1H), 6.27 (d, J=2.4 Hz, 2H), 4.17 (d, J=6.4 Hz, 2H), 3.58 (S, 6H), 3.55 (s, 3H). Following the general procedure for conversion of carboxylic acids to amides mentioned above and using dimethyl amine as amine, 28 was converted to 29 in 96% yield.

Analysis: $^1$HNMR (DMSO-$d_6$): δ 7.68 (t, J=4.6 Hz, 1H), 7.28 (d, J=8.8 Hz, 2H), 7.27 (d, J=8.8 Hz, 2H), 6.98 (d, J=8.8 Hz, 2H), 6.96 (d, J=8.8 Hz, 2H), 6.57 (s, 1H), 6.35 (t, J=2.8 Hz, 1H), 6.28 (d, J=2.4 Hz, 2H), 4.16 (d, J=6.4 Hz, 2H), 3.59 (S, 6H), 3.55 (s, 3H), 3.05 (br, 3H), 2.91 (br, 3H).

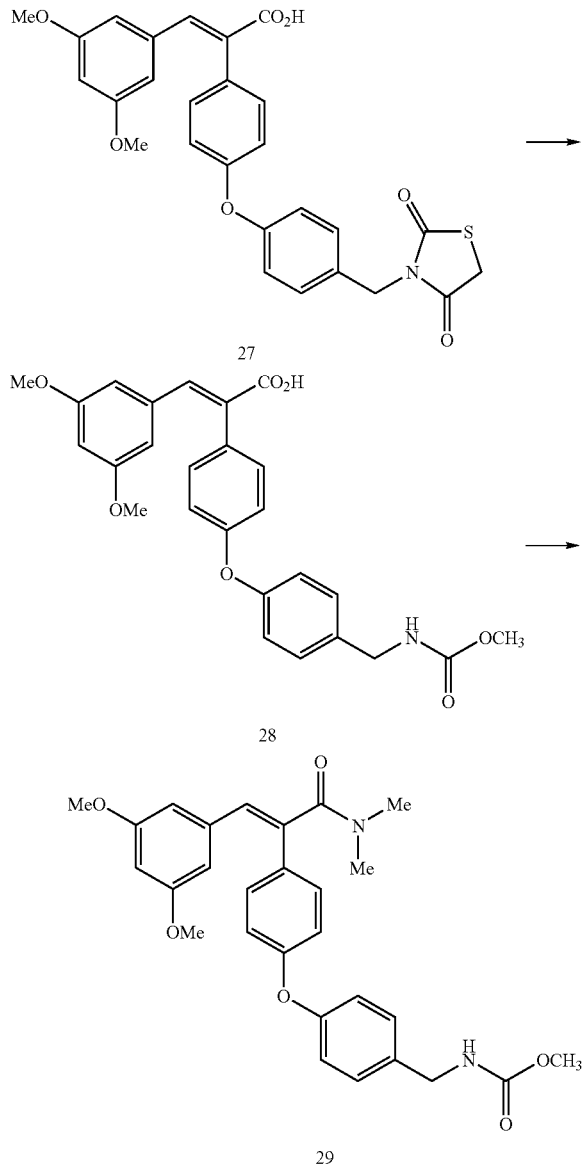

Example 13

Synthesis of 2-{4-[4-(2-carbamoylethyl)-phenoxy]-phenyl}-3-(3,5-dimethoxyphenyl) -N,N-dimethylacrylamide (31)

Urea (0.78 g, 13 mmol) and 3-(3,5-dimethoxyphenyl)-2-{4-[-4-(2-ethoxycarbonylethyl)-phenoxy]-phenyl}-acid 5 (0.45 g, 1.5 mmol) were dissolved in sodium ethoxide in ethanol (2M, 6.5 mL, 13 mmol) at 80° C. under argon, and the reaction mixture was heated at this temperature for 5 h. The reaction was then quenched by TFA (0.5 mL) after cooling to 5° C. Water (40 mL) was added to the reaction mixture. The crude product was filtered and purified by silica gel chromatography and eluted with hexane-ethyl acetate (1:1) containing acetic acid (1%). Yield (30): 0.39 g, 93%.

Analysis: $^1$HNMR (DMSO-$d_6$): δ 12.73 (br, 1H), 7.68 (s, 1H), 7.29 (br, 1H), 7.24 (d, J=8.8 Hz, 2H), 7.65 (d, J=8.8 Hz, 2H), 6.99 (d, J=8.8 Hz, 2H), 6.92 (d, J=8.8 Hz, 2H), 6.78 (br, 1H), 6.39 (t, J=2.4 Hz, 1H), 6.27 (d, J=2 Hz, 2H), 3.57 (s, 6H), 2.79 (t, J=8.0 Hz, 2H), 2.35 (t, J=8.0 Hz, 2H).

Following the general procedure for conversion of carboxylic acids to amides mentioned above and using dimethyl amine as amine, 30 was converted to 31 in 98% yield.

Analysis: $^1$HNMR (DMSO-$d_6$): δ 7.30 (br, 1H), 7.28 (d, J=8.8 Hz, 2H), 7.23 (d, J=8.8 Hz, 2H), 6.95 (d, J=8.8 Hz, 2H), 6.92 (d, J=8.8 Hz, 2H), 6.79 (br, 1H), 6.65 (s, 1H), 6.34 (t, J=2.4 Hz, 1H), 6.28 (d, J=2 Hz, 2H), 3.58 (s, 6H), 3.05 (br, 3H), 2.90 (br, 3H), 2.77 (t, J=8.0 Hz, 2H), 2.34 (t, J=8.0 Hz, 2H).

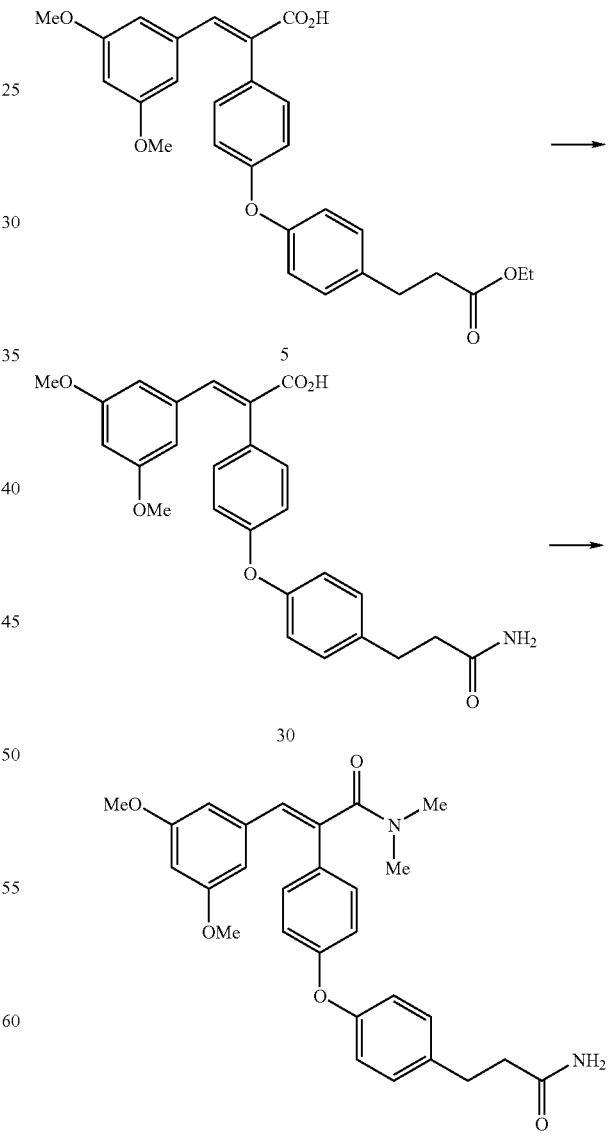

Example 14

Synthesis of 2-[4-(4-acetylaminophenoxy)-phenyl]-3-(3,5-dimethoxyphenyl)-N,N-dimethylacrylamide (34)

Compound 2 was reacted with 1-fluoro-4-nitrobenzene in the presence of NaH in DMF to give 3-(3,5-dimethoxyphenyl)-2-[4-(4-nitrophenoxy)-phenyl]-acrylic acid (32). Reduction of 32 (10 g, 24 mmol) with zinc dust (15 g, 230 mmol) in acetic acid (100 mL) was accomplished at 120° C. for 15 h, the mixture was cooled to room temperature. Water (250 mL) was slowly added to the reaction mixture. The precipitated product was filtered and washed with water (70 mL) to give crude product. The product was recrystallized from toluene. Yield (33): 9.7 g, 94%.

Analysis: $^1$HNMR (DMSO-$d_6$): δ 12.35 (br, 1H), 9.96 (s, 1H), 7.67 (s, 1H), 7.60 (d, J=8.8 Hz, 2H), 7.15 (d, J=8.8 Hz, 2H), 6.97 (d, J=8.8 Hz, 2H), 6.96 (d, J=8.8 Hz, 2H), 6.34 (t, J=2.8 Hz, 1H), 6.28 (d, J=2.4 Hz, 2H), 3.58 (S, 6H), 2.03 (s, 3H).

Following the general procedure for conversion of carboxylic acids to amides mentioned above and using dimethylamine as amine, 33 was converted to 34 in 98% yield.

Analysis: $^1$HNMR (DMSO-$d_6$): δ 9.96 (s,1H), 7.60 (d, J=8.8 Hz, 2H), 7.25 (d, J=8.8 Hz, 2H), 6.97 (d, J=8.8 Hz, 2H), 6.93 (d, J=8.8 Hz, 2H), 6.55 (s, 1H), 6.34 (t, J=2.8 Hz, 1H), 6.28 (d, J=2.4 Hz, 2H), 3.58 (S, 6H), 3.04 (br, 3H), 2.90 (br, 3H), 2.03 (s, 3H).

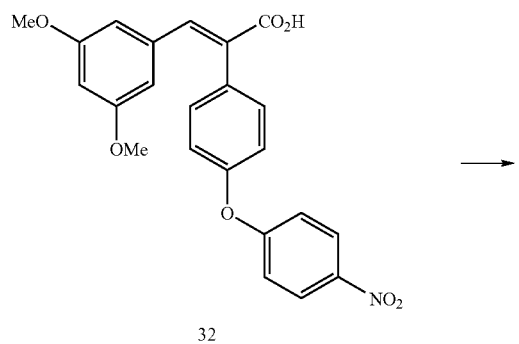

32

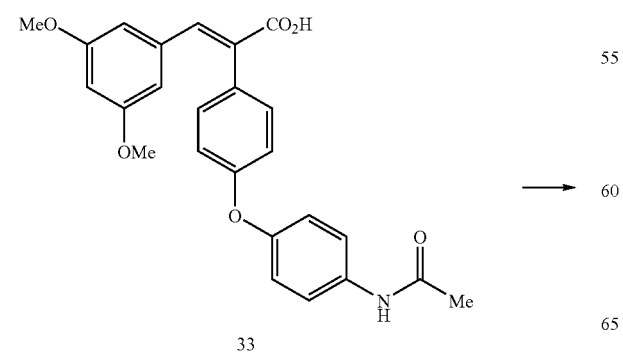

33

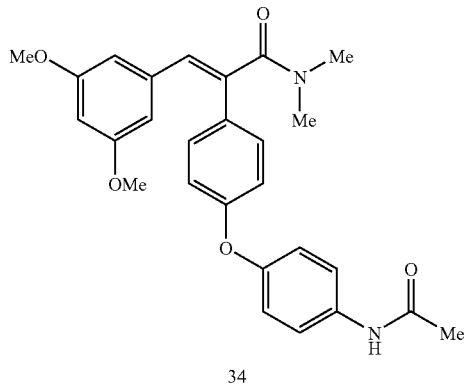

34

Example 15

Synthesis of 3-(3,5-dimethoxyphenyl)-2-[4-(4-methanesulfonylphenoxy)-phenyl]-N,N-dimethylacrylamide (36)

Compound 2 (3 g, 10 mmol) was dissolved in anhydrous DMF (70 mL) under nitrogen, and potassium carbonate (1.4 g, 10 mol) was added in lots. When the solution became homogeneous, 4-fluorophenyl methyl sulfone (1.74 g, 10 mmol) was added and the mixture was heated at 150° C. for 2 h. After cooling to room temperature, the solution was poured into water (150 mL). The mixture was acidified with 5% HCl to ~pH 4 and the solidified product was collected by suction filtration. The crude product was recrystallized with toluene. Yield(35): 4.3 g, 96%.

Analysis: $^1$HNMR (DMSO-$d_6$): δ 12.72 (br, 1H), 7.94 (d, J=8.8 Hz, 2H), 7.72 (s, 1H), 7.80 (d, J=8.4 Hz, 2H), 7.18 (d, J=8.8 Hz, 2H), 7.17 (d, J=8.4 Hz, 2H), 6.42 (t, J=2.8 Hz, 1H), 6.28 (d, J=2.4 Hz, 2H), 3.59 (S, 6H), 3.21 (s, 3H).

Following the general procedure for conversion of carboxylic acids to amides mentioned above and using dimethylamine as amine, 35 was converted to 36 in 96% yield.

Analysis: $^1$HNMR (DMSO-$d_6$): δ 7.93 (d, J=8.8 Hz, 2H), 7.38 (d, J=8.4 Hz, 2H), 7.17 (d, J=8.8 Hz, 2H), 7.16 (d, J=8.4 Hz, 2H), 6.62 (s, 1H), 6.36 (t, J=2.8 Hz, 1H), 6.29 (d, J=2.4 Hz, 2H), 3.59 (S, 6H), 3.20 (s, 3H), 3.08 (br, 3H), 2.92 (br, 3H).

2

-continued

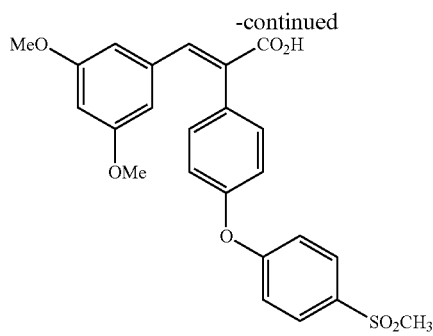

35

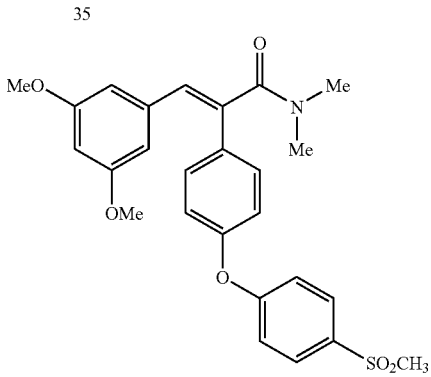

36

Example 16

Synthesis of 3-(4-{4-[2-(3,5-dimethoxyphenyl)-1-dimethylcarbamoylvinyl]-phenoxy}-phenyl)-propionic acid ethyl ester (37)

Following the general procedure for conversion of carboxylic acids to amides mentioned above and using dimethyl amine as amine, 5 was converted to 37 in 97% yield.

Analysis: $^1$HNMR (DMSO-$d_6$): δ 7.28 (d, J=8.8 Hz, 2H), 7.23 (d, J=8.8 Hz, 2H), 6.95 (d, J=8.8 Hz, 2H), 6.92 (d, J=8.8 Hz, 2H), 6.56 (s, 1H), 6.34 (t, J=2.4 Hz, 1H), 6.28 (d, J=2 Hz, 2H), 4.04 (q, J=6.8 Hz, 2H), 3.58 (s, 6H), 3.05 (br, 3H), 2.90 (br, 3H), 2.84 (t, J=8.4 Hz, 2H), 2.61 (t, J=8.4 Hz, 2H), 1.15 (t, J=6.4 Hz, 3H).

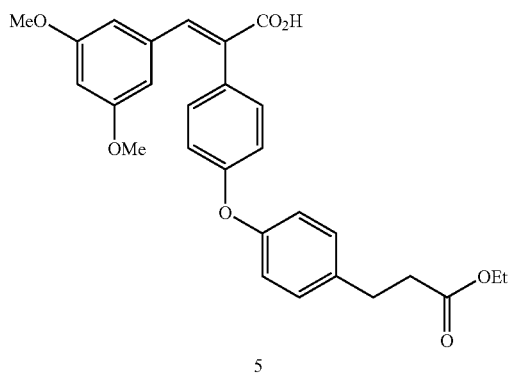

5

-continued

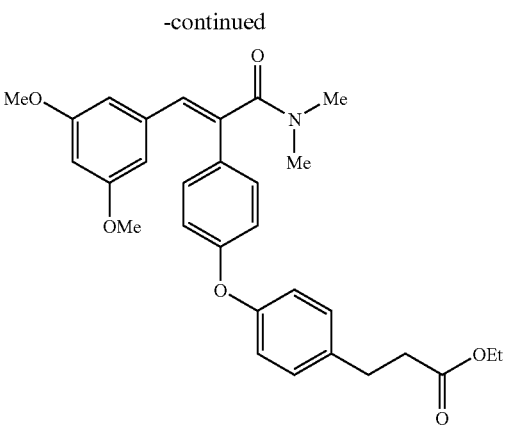

37

Example 17

Synthesis of 2-{4-[4-(N-ureido-2-carbamoylethyl)-phenoxy]-phenyl}-3-(3,5-Dimethoxyphenyl)-N,N-dimethylacrylamide (39)

Hydrolysis of 13 with 1N NaOH yielded 38. The 1,1-carbonyl-diimidazole (CDI) derivative was made by the general procedure for conversion of carboxylic acids to amides mentioned above. The CDI intermediate of 38 was converted to 39 by reacting this with semicarbazide in 73% yield.

Analysis: $^1$HNMR (DMSO-$d_6$): δ 9.48 (br, 1H), 7.72 (br, 1H), 7.28 (d, J=8.8 Hz, 2H), 7.25 (d, J=8.8 Hz, 2H), 6.95 (d, J=8.8 Hz, 2H), 6.92 (d, J=8.8 Hz, 2H), 6.56 (s, 1H), 6.34 (t, J=2.4 Hz, 1H), 6.28 (d, J=2 Hz, 2H), 5.86 (s, 2H), 3.58 (s, 6H), 3.05 (br, 3H), 2.90 (br, 3H), 2.77 (t, J=8.0 Hz, 2H), 2.39 (t, J=8.0 Hz, 2H).

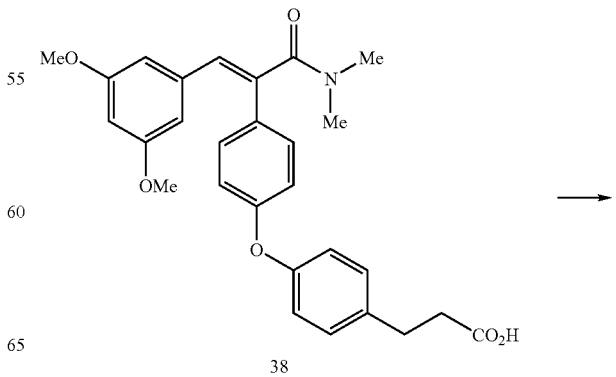

38

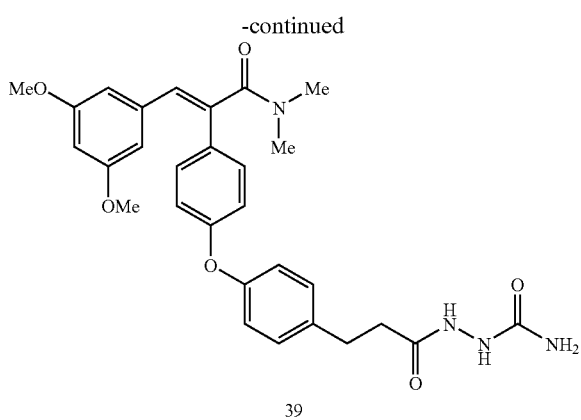

39

Example 18

Synthesis of 3-(3,5-dimethoxyphenyl)-N,N-dimethyl-2-{4-[4-(3-morpholin-4-yl-3-oxopropy)-phenoxy]-phenyl}-acrylamide (40)

The CDI intermediate of 38 was converted to 40 by reacting it with morpholine in 94% yield.

Analysis: $^1$HNMR (DMSO-d$_6$): δ 7.27 (d, J=8.8 Hz, 2H), 7.26 (d, J=8.8 Hz, 2H), 6.95 (d, J=8.8 Hz, 2H), 6.92 (d, J=8.8 Hz, 2H), 6.56 (s, 1H), 6.34 (t, J=2.4 Hz, 1H), 6.28 (d, J=2 Hz, 2H), 3.58 (s, 6H), 3.49 (m, 4H), 3.41 (m, 4H), 3.05 (br, 3H), 2.90 (br, 3H), 2.77 (t, J=8.0 Hz, 2H), 2.39 (t, J=8.0 Hz, 2H).

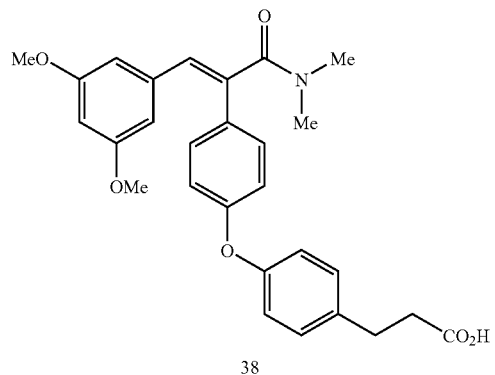

38

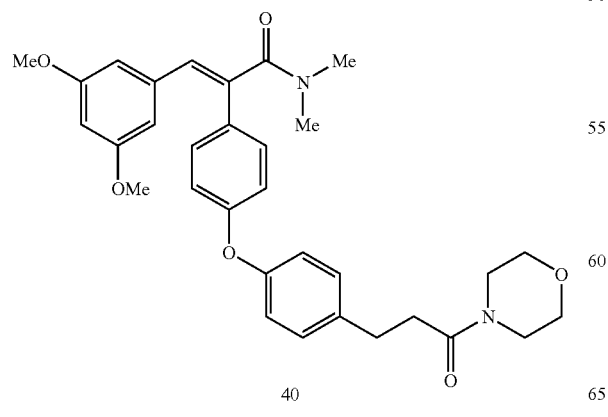

40

Example 19

Synthesis of 2-(4-{4-[2-(3,5-dimethoxyphenyl)-1-dimethylcarbamoylvinyl]-phenoxy}-benzyl)-malo acid dimethyl ester (43)

Condensation of 3 with malonic acid dimethyl ester in the presence of sodium hydride as base resulted in 41, which on reduction with zinc/acetic acid yielded 42. Conversion of 42 to 43 was accomplished by the general procedure for conversion of carboxylic acids to amides mentioned above in 94% yield.

Analysis: $^1$HNMR (DMSO-d$_6$): δ 7.29 (d, J=8.8 Hz, 2H), 7.23 (d, J=8.8 Hz, 2H), 6.96 (d, J=8.8 Hz, 2H), 6.92 (d, J=8.8 Hz, 2H), 6.57 (s, 1H), 6.34 (t, J=2.4 Hz, 1H), 6.28 (d, J=2 Hz, 2H), 3.87 (t, J=8 Hz, 1H), 3.61 (s, 6H), 3.58 (s, 6H), 3.08 (d, J=7.6 Hz, 2H), 3.05 (br, 3H), 2.91 (br, 3H).

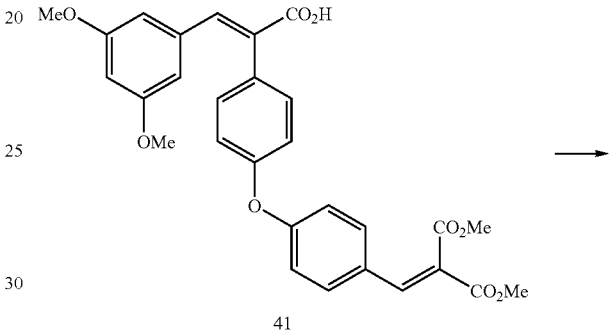

41

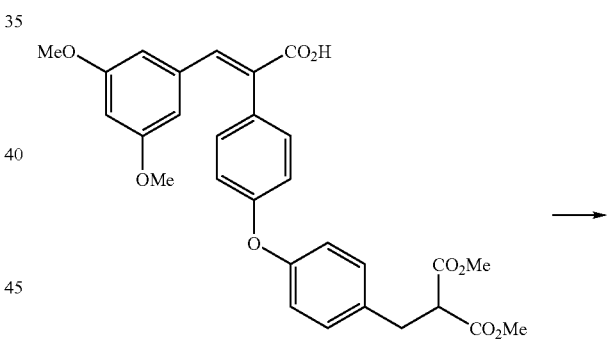

42

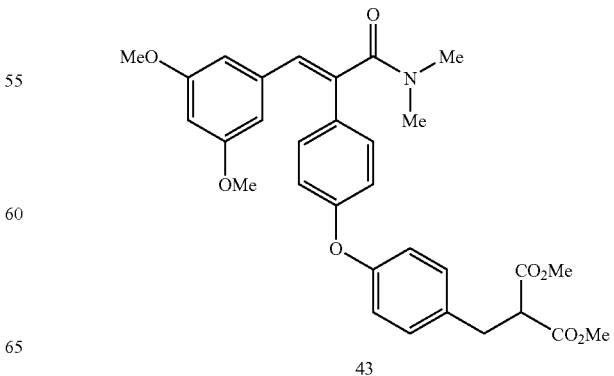

43

Example 20

Synthesis of N-{4-[2-(3,5-dimethoxyphenyl)-1-dimethylcarbamoylvinyl]-phenyl}-3-hydroxybenzamide (44)

A mixture of 2-(4-aminophenyl)-3-(3,5-dimethoxyphenyl)-N,N-dimethylacrylamide, 43, (0.59 g, 1.5 mmol), benzotriazol-1-yloxytris-(dimethylamino)-phosphonium hexafluorophosphate (BOP, 0.88 g, 2.0 mmol), 3-hydroxybenzoic acid (0.28 g, 2.0 mmol), triethylamine (0.2 g, 2.0 mmol) in DMF (8.0 mL) was stirred for 3 h at room temperature. The reaction mixture was poured in water (50 mL) and solid separated was filtered, dried and purity was checked by HPLC (97.6%).

Analysis: $^1$HNMR (DMSO-$d_6$): δ 10.29 (s, 1H), 9.81 (s, 1H), 7.79 (d, J=6.8 Hz, 2H), 7.43 (d, J=8.0 Hz, 1H), 7.37 (t, J=7.6 Hz, 2H), 7.29 (d, J=8.4 Hz, 2H), 7.02 (m, 1H), 6.60 (s, 1H), 6.40 (t, J=2.0 Hz, 1H), 6.36 (d, J=2.0 Hz, 2H), 3.63 (s, 6H), 3.08 (brs, 3H), 2.96 (brs, 3H).

Analysis: $^1$HNMR (DMSO-$d_6$): δ 12.78 (br, 1H), 10.29 (s, 1H), 8.42 (dd, J=4.8, 1.6 Hz, 1H), 8.35 (d, J=2.4 Hz, 1H), 7.92 (br, 1H), 7.66 (d, J=16 Hz, 1H), 7.64 (d, J=8.8 Hz, 2H), 7.36 (tt, J=8.4, 1.6 Hz, 1H), 7.30 (br, 1H), 7.28 (m, 1H), 7.23 (d, J=8.8 Hz, 2H), 7.11 (d, J=8.8 Hz, 2H), 7.09 (d, J=8.8 Hz, 2H), 6.73 (d, J=16 Hz, 1H).

Following the general procedure for conversion of carboxylic acids to amides mentioned above, 46 was converted to 47.

Analysis: $^1$HNMR (DMSO-$d_6$): δ 10.30 (s, 1H), 8.39 (dd, J=4.8, 1.6 Hz, 1H), 8.34 (d, J=2.4 Hz, 1H), 7.92 (br, 1H), 7.66 (d, J=16 Hz, 1H), 7.64 (d, J=8.8 Hz, 2H), 7.45 (tt, J=8.4, 1.6 Hz, 1H), 7.32 (br, 1H), 7.29 (d, J=8.8 Hz, 2H), 7.26 (m, 1H), 7.11 (d, J=8.8 Hz, 2H), 7.05 (d, J=8.8 Hz, 2H), 6.73 (d, J=16 Hz, 1H), 6.70 (s, 1H), 3.07 (br, 3H), 2.93 (br, 3H).

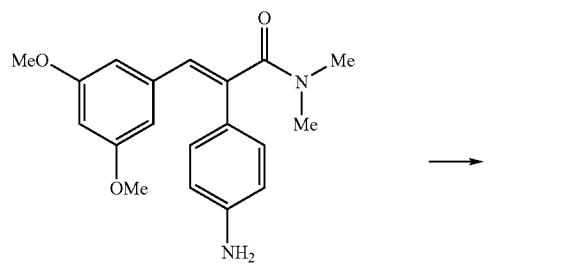

43

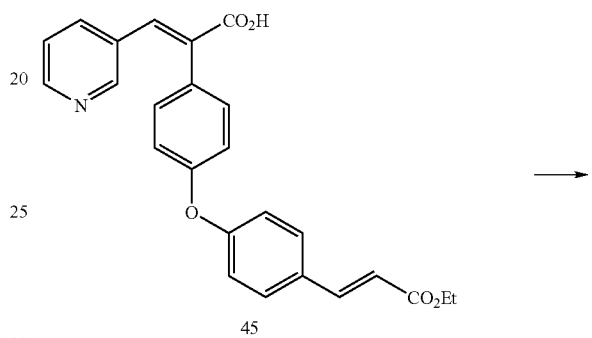

45

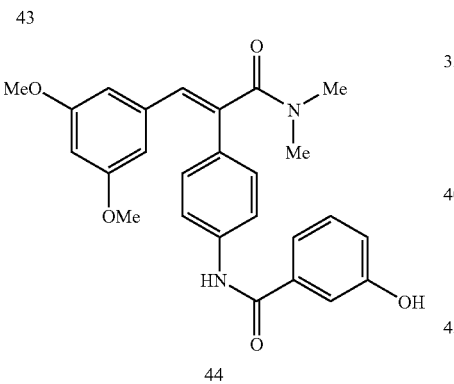

44

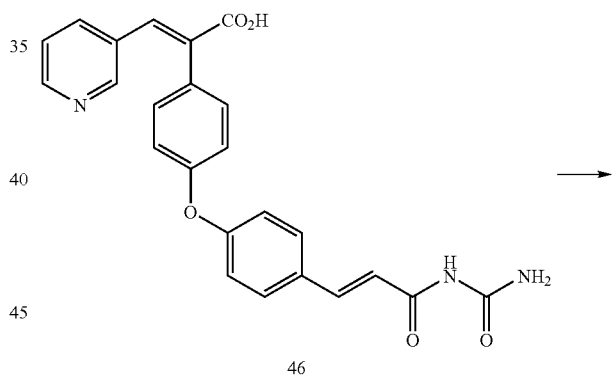

46

Example 21

Synthesis of N,N-Dimethyl-2-{4-[4-(3-oxo-3-ureidopropenyl)-phenoxy]-phenyl}-3-pyridin-3-ylacrylamide (47)

Synthesis of 45 from 3-pyridinecarboxaldehyde was performed following Scheme I. Urea (0.78 g, 13 mmol) and 2-{4-[4-(2-ethoxycarbonyl-vinyl)-phenoxy]-phenyl}-3-pridin-3-ylacrylic acid, 45 (0.5 g, 1.2 mmol) was dissolved in sodium ethoxide in ethanol (2M, 6.5 mL, 13 mmol) at 80° C. under argon, and the reaction mixture was heated at this temperature for 1 h. The reaction was then quenched by TFA (0.5 mL) after cooling to 5° C. Water (40 mL) was added to the reaction mixture. The crude product was filtered and purified by silica gel chromatography and eluted with hexanes-ethyl acetate (1:1) containing acetic acid (1%) followed by recrystallization from toluene. Yield (46): 0.33 g, 63%.

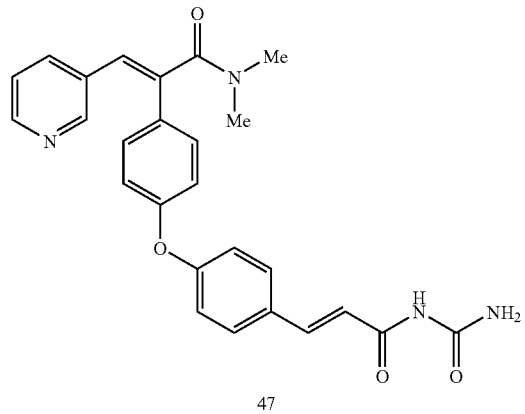

47

Example 22

Synthesis of 3-(3,5-dimethoxyphenyl)-2-(4-hydroxyphenyl)-N,N-dimethylacrylamide (49)

Following the general procedure for conversion of carboxylic acids to amides mentioned above and using dimethyl amine as amine, 2 was converted to 49.

Analysis: $^1$HNMR (DMSO-d$_6$): δ 9.59 (s, 1H), 7.07 (d, J=8.8, 2H), 6.73 (d, J=8. 8 Hz, 2H), 6.43 (s, 1H), 6.23 (t, J=2.4 Hz, 1H), 6.29 (d, J=2.4 Hz, 2H), 3.57 (s, 6H), 2.99 (brs, 3H), 2.89 (brs, 3H).

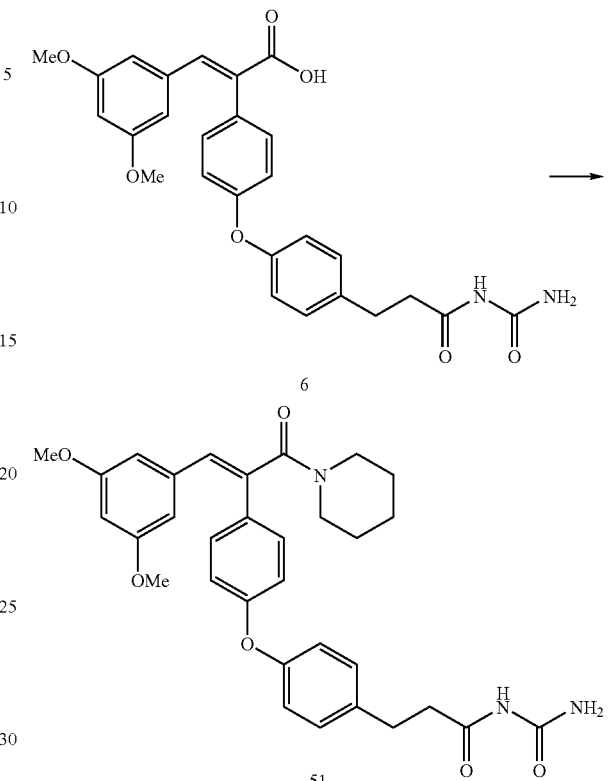

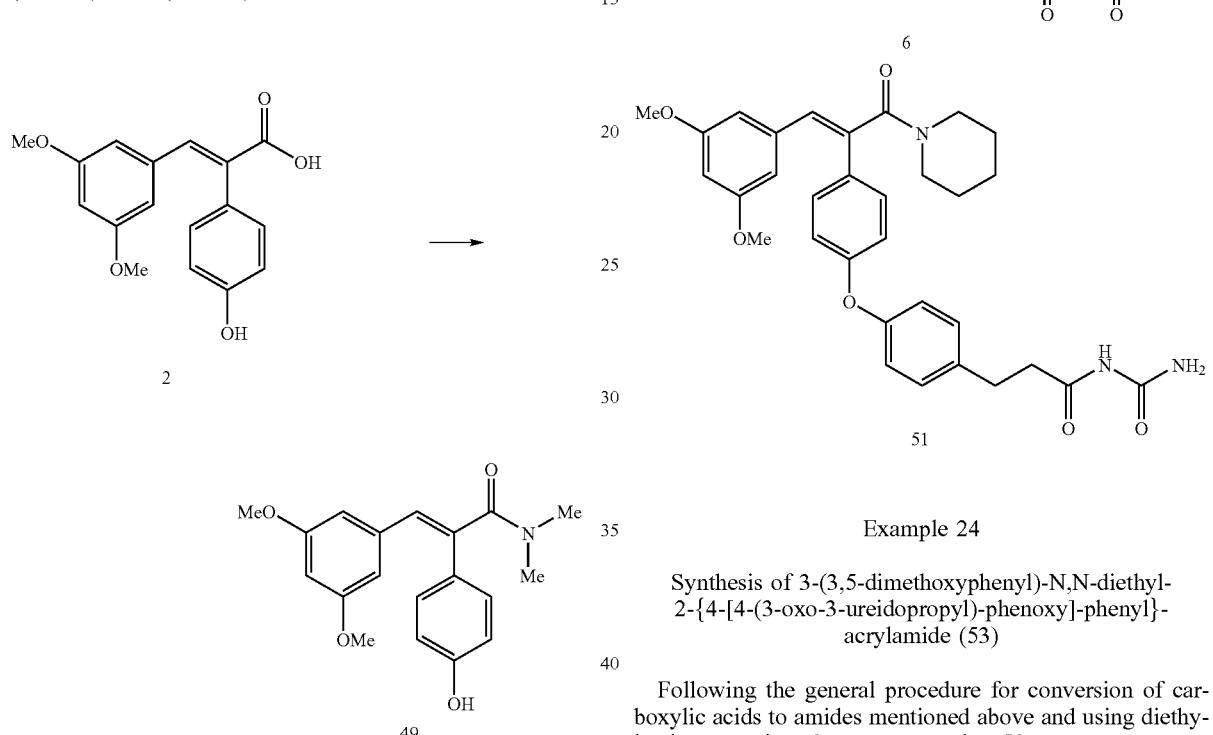

Example 23

Synthesis of [3-(4-{4-[2-(3,5-dimethoxyphenyl)-1-(piperidine-1-carbonyl)-vinyl]-phenoxy}-phenyl)-propionyl]-urea (51)

Following the general procedure for conversion of carboxylic acids to amides mentioned above and using piperidine as amine, 6 was converted to 51.

Analysis: $^1$HNMR (DMSO-d$_6$): δ 10.16 (s, 1H), 7.73 (brs, 1H), 7.26 (d, J=8.8 Hz, 2H), 7.23 (d, J=8.8 Hz, 2H), 6.98 (d, J=8.8 Hz, 2H), 6.93 (d, J=8.8 Hz, 2H), 6.55 (s, 1H), 6.34 (t, J=2.4 Hz, 1H), 6.29 (d, J=2.4 Hz, 2H), 3.58 (s, 6H), 3.50 (br, 4H), 2.82 (t, J=7.6 Hz, 2H), 2.59 (t, J=7.6 Hz, 2H), 1.58 (br, 2H) 1.40-1.45 (br, 4H).

Example 24

Synthesis of 3-(3,5-dimethoxyphenyl)-N,N-diethyl-2-{4-[4-(3-oxo-3-ureidopropyl)-phenoxy]-phenyl}-acrylamide (53)

Following the general procedure for conversion of carboxylic acids to amides mentioned above and using diethylamine as amine, 6 was converted to 53.

Analysis: $^1$HNMR (DMSO-d$_6$): δ 10.17 (s, 1H), 7.70 (brs, 1H), 7.26 (overlapped d, J=8.8 Hz, 2H), 7.23 (overlapped d, J=8.8 Hz, 2H), 6.97 (d, J=8.8 Hz, 2H), 6.92 (d, J=8.8 Hz, 2H), 6.54 (s, 1H), 6.34 (t, J=2.0 Hz, 1H), 6.29 (d, J=2.0 Hz, 2H), 3.32-3.37 (br, 4H), 3.59 (s, 6H), 2.82 (t, J=7.6 Hz, 2H), 2.59 (t, J=7.6 Hz, 2H), 1.03 (br, 3H), 0.92 (br, 3H).

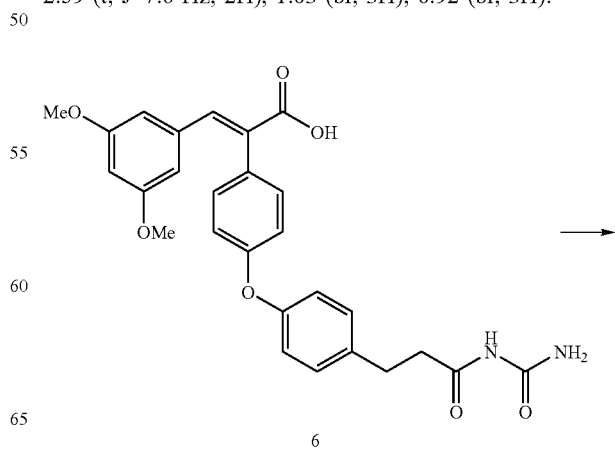

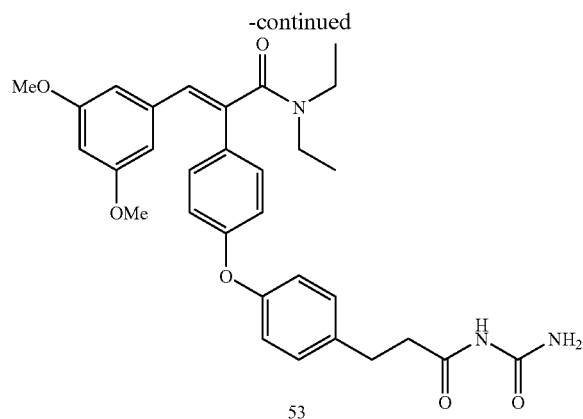

Example 25

Synthesis of 2-{4-[4-(3-acetylamino-3-oxopropyl)-phenoxy]-phenyl}-3-(4-fluorophenyl)-N,N-dimethylacrylamide (56)

To a solution of {4-[4-(2-carbamoylethyl)-phenoxy]-phenyl}-acetic acid, 54, (0.45 g, 1.5 mmol) in acetic anhydride (15 mL) was added 4-fluorobenzaldehyde (0.17 mL, 1.6 mmol) and potassium acetate (0.17 g, 1.8 mmol) and refluxed overnight. Reaction mixture was poured in water (50 mL) and extracted with ethyl acetate (2×50 mL). The crude product was purified by silica gel chromatography to yield 55.

Analysis: $^1$HNMR (DMSO-$d_6$): δ 12.50 (br, 1H), 10.64 (s, 1H), 7.74 (s,1H), 7.27 (d, J=8.4 Hz, 2H), 7.10-7.15 (m, 6H), 6.99 (d, J=8.4 Hz, 2H), 6.97 (d, J=8.4 Hz, 2H), 2.81 (d, J=6.8 Hz, 2H), 2.76 (d, J=6.8 Hz, 2H), 2.15 (s, 3H).

Following the general procedure for conversion of carboxylic acids to amides mentioned above and using dimethylamine as amine, 55 was converted to 56.

Analysis: $^1$HNMR (DMSO-$d_6$): δ 10.62 (s, 1H), 7.26 (d, J=8.4 Hz, 2H), 7.22 (d, J=8.4 Hz, 2H), 7.15 (d, J=8.4 Hz, 2H), 7.05 (d, J=8.4 Hz, 2H), 6.97 (d, J=8.0 Hz, 2H), 6.94 (d, J=8.0 Hz, 2H), 6.63 (s, 1H), 2.81 (d, J=6.8 Hz, 2H), 2.76 (d, J=6.8 Hz, 2H), 2.15 (s, 3H).

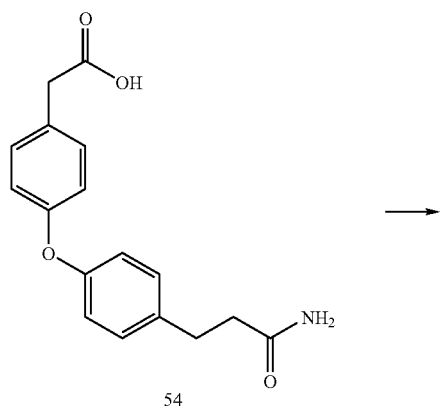

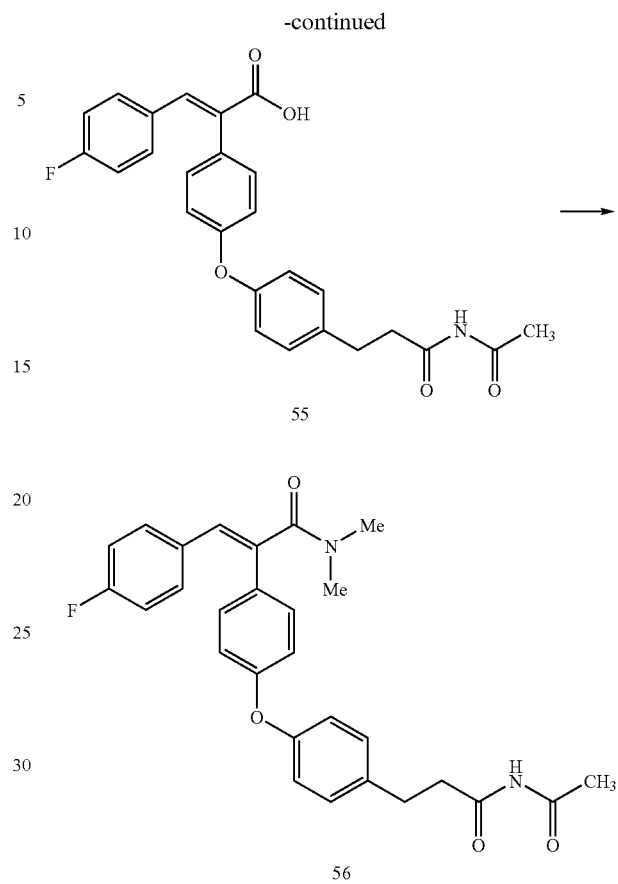

Example 26

Synthesis of 2-(4-{4-[2-(3,5-dimethoxyphenyl)-1-dimethylcarbamoylvinyl]-phenoxy}-benzyl)-malo acid (58) and 2-(4-{4-[2-(3,5-dimethoxyphenyl)-1-dimethylcarbamoylvinyl]-phenoxy}-benzyl)-malonamide (59)

To a solution of 2-(4-{4-[2-(3,5-dimethoxyphenyl)-1-dimethylcarbamoylvinyl]-phenoxy}-benzyl)-malonic acid dimethyl ester, 43 (0.40 g, 0.73 mmol) in DMF (6 mL) and ethanol (10 mL), ammonium hydroxide (20 mL, 28%) and 1N NaOH (0.36 mL, 0.36 mmol) was added and stirred overnight at room temperature. Solvent was evaporated and the crude product was purified by silica gel chromatography to yield 58 and 59.

Analysis: $^1$HNMR (DMSO-$d_6$+$D_2O$) of 58: δ 7.20 (d, J=8.4 Hz, 2H), 7.17 (d, J=8.4 Hz, 2H), 6.90 (d, J=8.4 Hz, 2H), 6.81 (d, J=8.4 Hz, 2H), 6.51 (s, 1H), 6.29 (t, J=2.0 Hz, 1H), 6.21 (d, J=2.0 Hz, 2H), 3.53 (s, 6H), 3.13 (br, 1H), 3.01 (brs 3H), 2.92 (br, 2H), 2.86 (brs, 3H).

Analysis: $^1$HNMR (DMSO-$d_6$) of 59: δ67 7.28 (d, J=8.8 Hz, 2H), 7.26 (br, 2H), 7.22 (d, J=8.8 Hz, 2H), 7.03 (br, 2H), 6.97 (d, J=8.8 Hz, 2H), 6.90 (d, J=8.8 Hz, 2H), 6.56 (s, 1H), 6.34 (t, J=2.4 Hz, 1H), 6.28 (d, J=2 Hz, 2H), 3.58 (s, 6H), 3.29 (t, J=8.8 Hz, 1H), 3.05 (br, 3H), 2.95 (d, J=7.6 Hz, 2H), 2.91 (br, 3H).

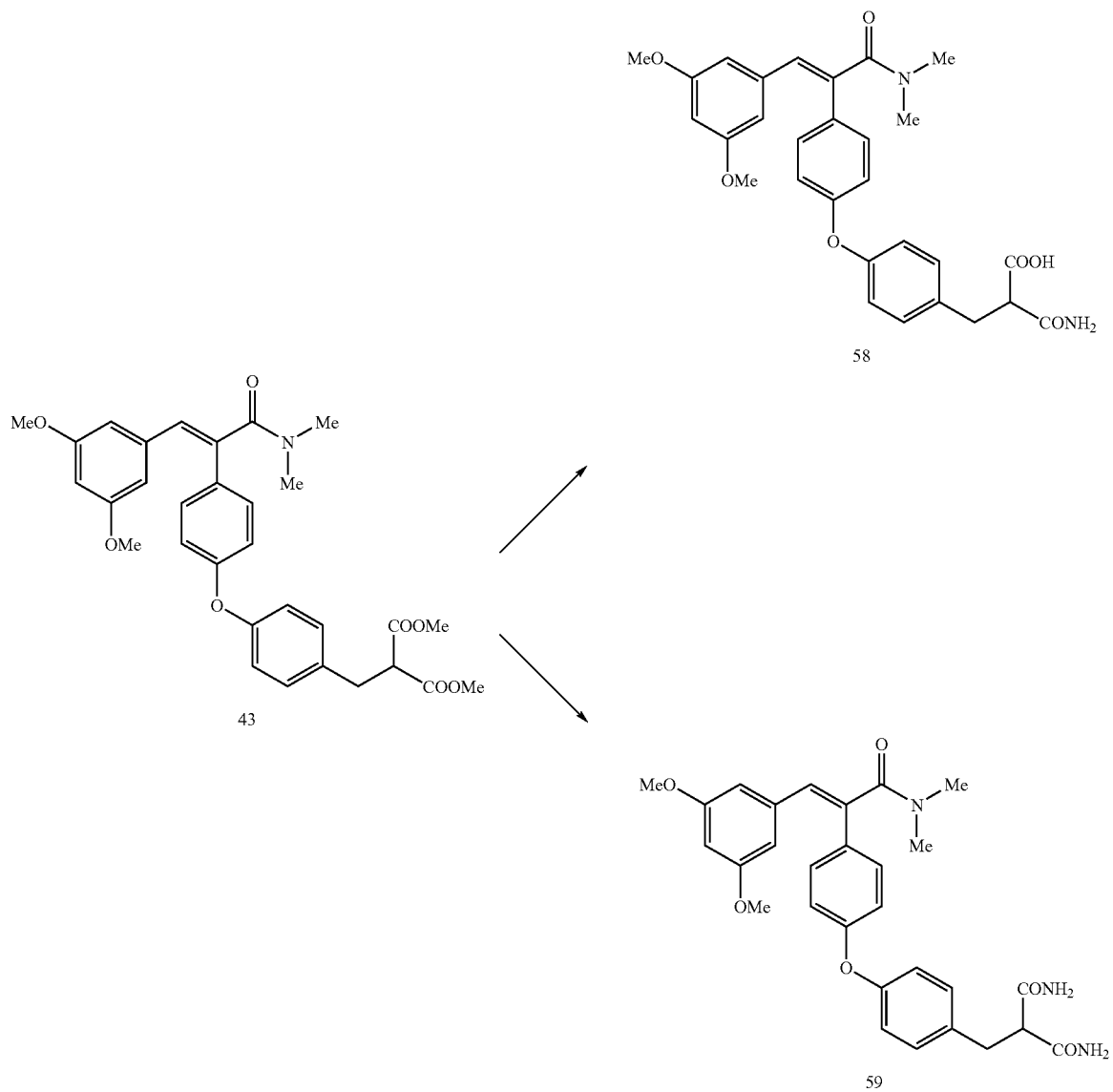
Example 27
Synthesis of 3-(3,5-dimethoxyphenyl)-2-{4-[4-(3-oxo-3-ureidopropyl)-phenoxy]-phenyl}-N-pyridin-4-ylacrylamide (60)
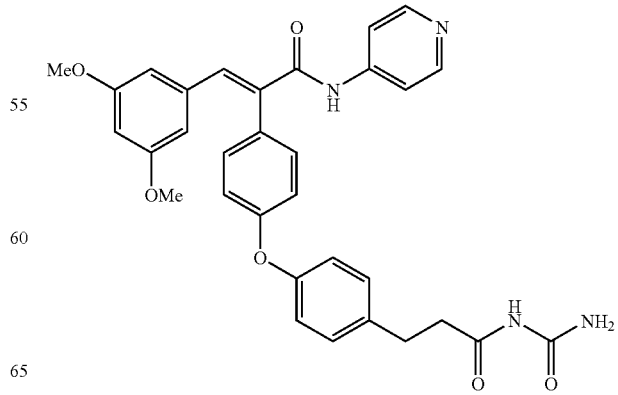
Following the general procedure for conversion of carboxylic acids to amides mentioned above and using 4-aminopyridine as amine, 6 was converted to 60.
Analysis: $^1$HNMR (DMSO-$d_6$): δ10.17 (s, 1H), 8.24 (brs, 1H), 7.71 (br, 2H), 7.53 (d, J=8.8 Hz, 2H), 7.44 (s, 1H), 7.25 (d, J=8.4 Hz, 2H), 7.22 (br, 1H), 7.03 (d, J=9.2 Hz, 2H), 7.99 (d, J=8.4 Hz, 2H), 6.47 (d, J=2.4 Hz, 2H), 6.43 (t, J=2.4 Hz, 2H), 3.65 (s, 6H), 2.83 (t, J=7.6 Hz, 2H), 2.60 (t, J=7.6 Hz, 2H).

Example 28

Synthesis of N-(4-chlorophenyl)-3-(3,5-dimethoxyphenyl)-2-{4-[4-(3-oxo-3-ureidopropyl)-phenoxy]-phenyl}-acrylamide (61)

Following the general procedure for conversion of carboxylic acids to amides mentioned above and using 4-chloroaniline as amine, 6 was converted to 61.

Analysis: $^1$HNMR (DMSO-$d_6$): δ 10.16 (s, 1H), 8.24 (brs, 1H), 7.65 (brs, 1H), 7.53 (d, J=8.8 Hz, 2H), 7.44 (s, 1H), 7.25 (d, J=8.8 Hz, 2H), 7.22 (br, 1H), 7.03 (d, J=8.8 Hz, 2H), 7.00 (d, J=8.8 Hz, 2H), 6.47 (d, J=2.4 Hz, 2H), 6.43 (d, J=2.4 Hz, 1H), 3.66 (s, 6H), 2.83 (t, J=8.0 Hz, 2H), 2.60 (t, J=8.0 Hz, 2H).

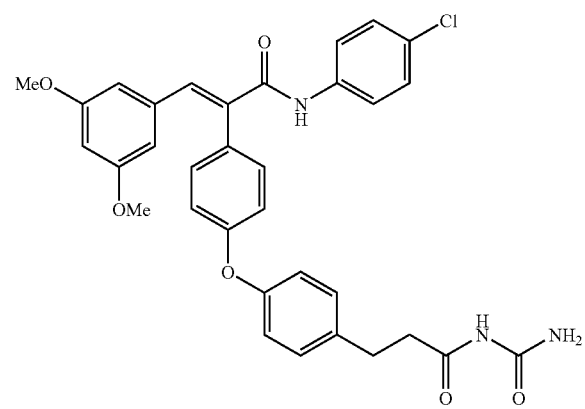

61

Example 29

Synthesis of 3-(3,5-dimethoxyphenyl)-N,N-dimethyl-2-(4-{4-[2-(2-morpholin-4-yl-2-oxoethylcarbamoyl)-ethyl]-phenoxyl}-phenyl)-acrylamide (63)

Following the general procedure for conversion of carboxylic acids to amides mentioned above and using 2-amino-1-morpholin-4-yl-ethanone as amine, 3-(4-{4-[2-(3,5-dimethoxyphenyl)-1-dimethylcarbamoylvinyl]-phenoxy}-phenyl)-propionic acid, 38, was converted to 63.

Analysis: $^1$HNMR (DMSO-$d_6$): δ 7.99 (t, J=5.6 Hz, 1H), 7.27 (d, J=8.8 Hz, 2H), 7.24 (d, J=8.8 Hz, 2H), 6.97 (d, J=8.8 Hz, 2H), 6.92 (d, J=8.8 Hz, 2H), 6.56 (s, 1H), 6.34 (t, J=2.0 Hz, 1H), 6.28 (d, J=2.0 Hz, 2H), 3.93 (d, J=5.6 Hz, 2H) 3.56 (s, 6H), 3.52-3.56 (m, 4H), 3.40-3.42 (m, 4H), 3.05 (brs, 3H), 2.91 (brs, 3H), 2.80 (t, J=7.6 Hz, 2H), 2.46 (t, J=7.6 Hz, 2H).

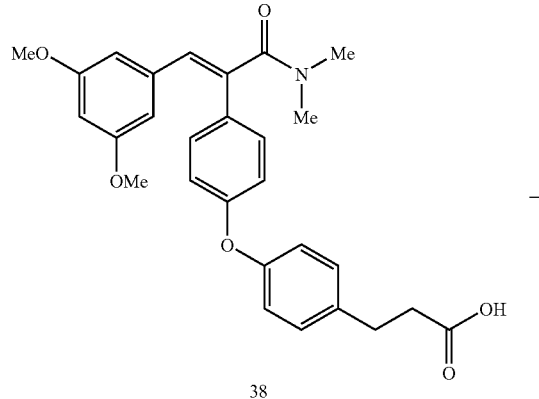

-continued

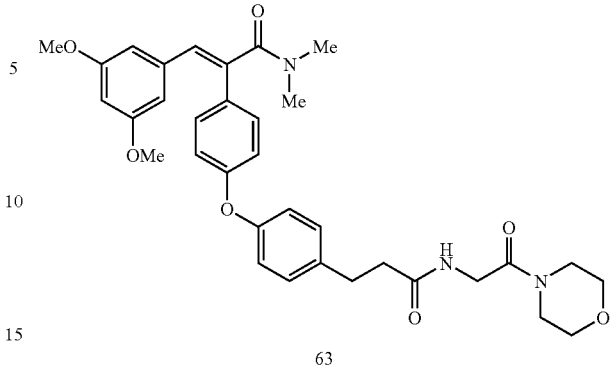

63

Example 30

Synthesis of 3-(3,5-dimethoxyphenyl)-N,N-dimethyl-2-(4-{4-[3-(4-methylpiperazin-1-yl)-3-oxopropyl]-phenoxy}-phenyl)-acrylamide (64)

Following the general procedure for conversion of carboxylic acids to amides mentioned above and using 4-methylpiperazine as amine, 3-(4-{4-[2-(3,5-dimethoxyphenyl)-1-dimethylcarbamoylvinyl]-phenoxy}-phenyl)-propionic acid, 38, was converted to 64.

Analysis: $^1$HNMR (DMSO-$d_6$): δ 7.28 (d, J=2.8 Hz, 2H), 7.25 (d, J=2.8 Hz, 2H), 6.96 (d, J=8.8 Hz, 2H), 6.92 (d, J=8.6 Hz, 2H), 6.56 (s, 1H), 6.34 (t, J=2.0 Hz, 1H), 6.28 (d, J=2.0 Hz, 2H), 6.19 (s, 6H), 3.40 (dt, 2=18.0 and 4.8 Hz), 3.04 (brs, 3H), 2.90 (brs, 3H), 2.79 (t, J=8.0 Hz, 2H), 2.60 (t, J=8.0 Hz, 2H), 2.20 (t, J=5.2 Hz, 2H), 2.14 (s, 3H).

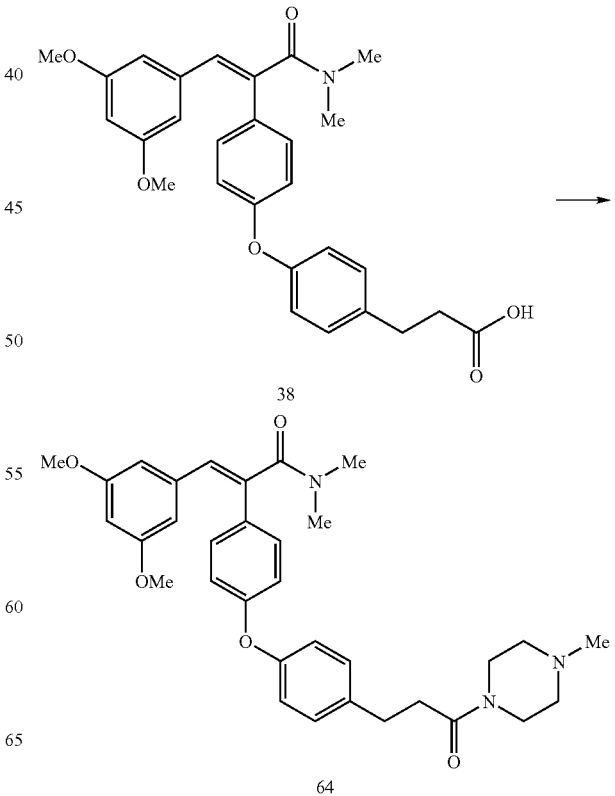

Example 31

Synthesis of 3-(3,5-dimethoxyphenyl)-N,N-dimethyl-2-[4-(pyridin-2-yloxy)-phenyl]-acrylamide (66)

A solution of 3-(3,5-dimethoxyphenyl)-2-(4-hydroxyphenyl)-acrylic acid, 2, (0.6 g, 2.0 mmol), 2-fluoropyridine (0.19 g, 2.0 mmol) in dimethyl acetamide (4.0 mL) was heated in presence of potassium carbonate (0.28 g, 2.0 mmol) at 175° C. for 2 h, and then quenched with water (25 mL), neutralized with dilute HCl and extracted with ethyl acetate (2×50 mL). Organic layer was dried and evaporated. The crude product was purified by silica gel chromatography to yield 65 (0.15 g, 19.9%).

A mixture of 3-(3,5-dimethoxyphenyl)-2-[4-(pyridin-2-yloxy)-phenyl]-acrylic acid, 65, (0.11 g, 0.3 mmol), benzotriazol-1-yloxytris-(dimethylamino)-phosphonium hexafluorophosphate (BOP, 0.15 g, 0.35 mmol), dimethylamine in THF (2M, 0.5 mL, 1.0 mmol), triethylamine ( 0.035 g, 035 mmol) in DMF (6.0 mL) was stirred for 3 h at room temperature. The reaction mixture was poured in water (50.0 mL) and extracted with ethyl acetate (2×50 mL). Solvent was evaporated under reduced pressure and residue was purified by silica gel chromatography to yield 66.

Analysis: $^1$HNMR (DMSO-$d_6$): δ 8.14 (m, 1H), 7.88 (m, 1H), 7.33 (d, J8.8 Hz, 2H), 7.14 (m, 3H), 7.05 (d, J=8.4 Hz, 2H), 6.59 (s, 1H), 6.34 (t, J=2.0 Hz, 1H), 6.31 (d, J=2.0 Hz, 2H), 3.58 (s, 6H), 3.10 (brs, 3H), 2.92 (brs, 3H).

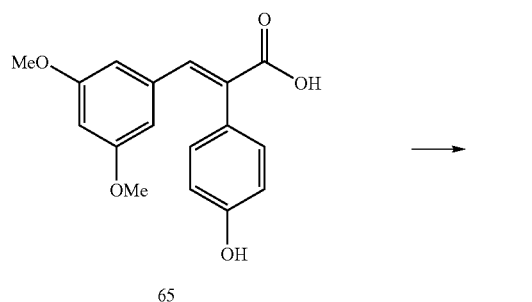

65

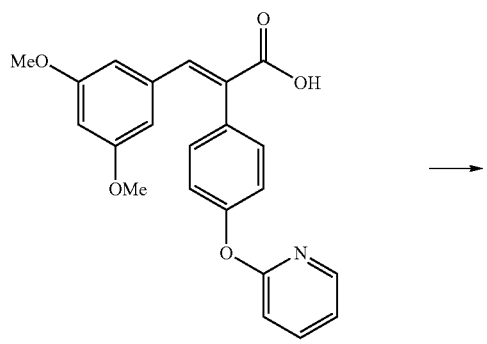

66

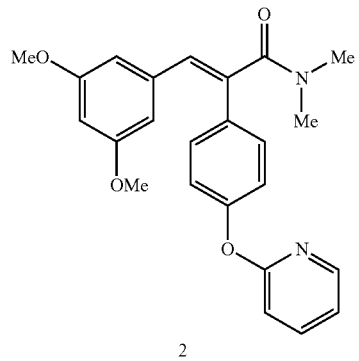

2

Example 32

Measurement of Increased Glucose Uptake in 3T3-L1 Adipocytes Treated With a Compound of the Present Invention The effect of treatment with 1 on glucose uptake was measured in 3T3-L1 differentiated adipocytes. The assay was conducted essentially according to the method of Tafuri S R, *Endocrinology*, 137, 4706-4712 (1996). The adipocytes were incubated with different concentrations of the test compound for 48 hours in Dulbecco's modified Eagle's medium (DMEM) containing 10% fetal bovine serum (FBS), then washed and incubated in glucose-free, serum-free medium for 60 minutes at 37° C. Then $^{14}$C-deoxyglucose was added and the cells were incubated for 30 minutes at room temperature. After washing, the cells were lysed (0.1% SDS) and the radioactivity was measured to determine the amount of glucose uptake. Glucose uptake was calculated as a percentage of the basal level seen in cells not treated with drug. As shown in FIG. 1, treatment with 1 resulted in a dose-dependent increase in glucose uptake.

Example 33

Measurement of Enhanced Glucose Uptake in 3T3-L1 Adipocytes Treated With Insulin in Combination with a Compound of the Present Invention The ability of 1 to enhance insulin-stimulated glucose uptake was assessed in 3T3-L1 adipocytes essentially as described above in Example 32. Adipocytes were incubated with either vehicle (0.1% DMSO) or test compound (5 μM 1) for 48 hours in DMEM plus 10% FBS. The cells were then serum-starved, incubated for 30 minutes with different concentrations of insulin, and then glucose uptake was carried out for 10 minutes at room temperature. When compared to treatment with vehicle, treatment with 1 enhanced the stimulation of glucose uptake by insulin (see FIG. 2).

Example 34

Measurement of the Glucose-Lowering Effect in ob/ob Mice Treated With a Compound of the Present Invention The glucose-lowering effect of 1 was measured in ob/ob mice, an animal model for type 2 diabetes. At the onset of diabetes, seven-week-old male ob/ob mice received daily oral doses of either vehicle (0.5% CMC) or 1 (10 mg/kg) by gavage for seven days. Blood glucose levels were measured on day 0 (24 hours prior to administration of the first dose), day 1 (immediately prior to the first dose), and on days 2, 4, 6 and 8 (24 hours following administration of the prior dose). Significant decreases in blood glucose levels were recorded on day 6 (36% decrease, p<0.05) and day 8 (23% decrease, p<0.05) in the drug-treated versus the vehicle-treated animals (see FIG. 3).

Example 35

Measurement of the Lipid-Lowering Effects in ob/ob Mice Treated With a Compound of the Present Invention The lipid-lowering effects of 1 also were measured in ob/ob mice following one week of treatment. In the experiment described above in Example 34, the concentrations of serum triglycerides and free fatty acids were determined on day 8. Significant decreases were observed in the levels of serum triglycerides (49% lower, p<0.05) and free fatty acids (19% lower, p<0.05) in the drug-treated versus the vehicle treated mice (see FIG. 4).

Example 36

Measurement of the Inhibition of LPS-induced TNF-alpha Production in RAW264.7 Cells Treated With a Compound of the Present Invention The ability of 1 to inhibit LPS-induced TNF-alpha production was assessed in the mouse macrophage cell line RAW264.7. The RAW cells were preincubated with either 1 µM dexamethasone (Dex) or 10, 30 or 100 µM 1 for 1 hour at 37° C. in RPMI-1640 containing 10% FBS. After 1 hour LPS (0.1 µg/ml) was added and cells were incubated an additional 6 hours. Cell supernatant was then collected, aliquoted and frozen at −70° C., and an aliquot used to determine the concentration of TNF-alpha by ELISA. As shown in FIG. 5, treatment with 1 significantly inhibited the LPS-induced production of TNF-alpha. The inhibitory effect approached that seen with dexamethasone.

Example 37

Measurement of the Inhibition of LPS-induced IL-1 Beta Production in RAW264.7 Cells Treated With a Compound of the Present Invention The ability of 1 to inhibit LPS-induced IL-1 beta production was also examined in RAW264.7 cells. The RAW cells were preincubated with either 1 µM dexamethasone (Dex) or 10, 30 or 100 µM 1 for 1 hour at 37° C. in RPMI-1640 containing 10% FBS. After 1 hour LPS (0.1 µg/ml) was added and cells were incubated an additional 6 hours. Cell supernatant was then collected, aliquoted and frozen at −70° C., and an aliquot used to determine the concentration of IL-1 beta by ELISA. As shown in FIG. 6, treatment with 1 significantly inhibited the LPS-induced production of IL-1 beta. The inhibition seen with 1 was of the same approximate magnitude as that seen with dexamethasone.

Example 38

Measurement of the Inhibition of LPS-induced IL-6 Production in RAW264.7 Cells Treated With a Compound of the Present Invention The ability of 1 to inhibit LPS-induced IL-6 production was also measured in RAW264.7 cells. The RAW cells were preincubated with either 1 µM dexamethasone (Dex) or 10, 30 or 100 µM 1 for 1 hour at 37° C. in RPMI-1640 containing 10% FBS. After 1 hour LPS (0.1 µg/ml) was added and cells were incubated an additional 6 hours. Cell supernatant was then collected, aliquoted and frozen at −70° C., and an aliquot used to determine the concentration of IL-6 by ELISA. As shown in FIG. 7, treatment with 1 significantly inhibited the LPS-induced production of IL-6. The inhibitory effect was greater than that observed with dexamethasone.

Example 39

Measurement of the Inhibition of LPS-induced iNOS and COX-2 Production in RAW264.7 Cells Treated With a Compound of the Present Invention The ability of 1 to inhibit LPS-induced production of iNOS and COX-2 was also measured in RAW264.7 cells. The RAW cells were preincubated with either 1 µM dexamethasone (Dex) or 10, 30 or 100 µM 1 (Test Cpd) or other reference compound (Ref Cpd A or Ref Cpd B) for 1 hour at 37° C. in RPMI-1640 containing 10% FBS. After 1 hour LPS (0.1 µg/ml) was added and cells were incubated an additional 6 hours. Cells receiving no drug treatment, incubated with or without LPS, served as controls. Cells were lysed and 25 µg/well of total protein was electrophoresed on 4-20% Tris-glycine SDS gels. Proteins were transferred to nitrocellulose membrane, and the resulting blot was probed with antibody to iNOS, then stripped and reprobed with antibody to COX-2, and then stripped and reprobed with antibody to COX-1. As shown in FIG. 8, treatment with 1 exhibited dose-dependent inhibition of LPS-induced iNOS production. In addition, treatment with 1 selectively inhibited production of COX-2 but not COX-1 in LPS-stimulated cells.

Example 40

Inhibition of LPS-induced TNF-alpha Release by Human Monocytes With Compounds of the Present Invention Frozen human elutriated monocytes (Advanced Biotechnologies Incorporated) were thawed and each 1-ml vial mixed with ~12 ml of 10% FBS complete medium (10% heat-inactivated fetal bovine serum in RPMI 1640 medium supplemented with 100 U/ml penicillin, 100 µg/ml streptomycin and 50 µM 2-mercaptoethanol). Cells were centrifuged at 800 rpm for 10 min at room temperature using a Beckman GS-6 centrifuge with GH-3.8 rotor, and the cell pellets were resuspended in 20% FBS complete medium (20% heat-inactivated FBS in RPMI 1640 medium supplemented with 100 U/ml penicillin, 100 µg/ml streptomycin and 50 µM 2-mercaptoethanol) and centrifuged again at 800 rpm for 10 min at room temperature. Cell pellets were resuspended in 20% FBS complete medium, and the cell suspensions were pooled and passed through a 70-micron cell strainer to remove any aggregates or clumps. The cell suspension was adjusted to 2.5×10⁶ cells/ml in 20% FBS complete medium. Cell suspension (160 µl, 4×10⁵ cells) was added into each well of a 96-well tissue-culture treated polystyrene plate and incubated at 37° C. for 1-2.5 h. Cells were pretreated with vehicle (DMSO) or test compound (0.3, 1.0, 3,0, 10 or 30 µM) in 20% FBS complete medium for 1 h at 37° C. After pretreatment, lipopolysaccharides (LPS) from *Salmonella typhimurium* in 20% FBS complete medium were added to the cells. The final concentrations were 0.1% DMSO and 10 ng/ml LPS in a final volume of 200 µl/well. The cells were incubated for 20 h at 37° C., and then the supernatants were harvested and aliquots of the supernatants frozen at −80° C. for subsequent analysis. Cells on the plates were assayed for cell viability using the MTS/PMS assay (Cory A H et al., Cancer Commun 3:207-212, 1991). The concentration of TNF-alpha in the cell supernatants was determined using quantitative sandwich enzyme immunoassay for human TNF-alpha (R&D Systems). The mean percent inhibition of TNF-alpha release relative to vehicle was calculated for each concentration of test compound from multiple determinations. As shown in Table 2, the compounds of the invention caused significant inhibition of LPS-induced TNF-alpha release by human monocytes.

TABLE 2

| Test Compound | Percent Inhibition of TNF-alpha Release | | | | |
|---|---|---|---|---|---|
| | 0.3 µM | 1.0 µM | 3.0 µM | 10 µM | 30 µM |
| 49 | — | — | 14% | 47% | 54% |
| 31 | — | 51% | 73% | 83% | 86% |
| 37 | — | 17% | 38% | 65% | 78% |
| 13 | 15% | 40% | 70% | 78% | 78% |
| 51 | — | — | 25% | 57% | * |
| 56 | 1% | — | 6% | — | 54% |
| 66 | 27% | — | 53% | — | 84% |
| 67 | 40% | — | 62% | — | 89% |
| 44 | 32% | — | 67% | — | 91% |
| 71 | 20% | — | 47% | — | 65% |
| 69 | 1% | — | 22% | — | 50% |
| 58 | 6% | — | 13% | — | 53% |
| 59 | 27% | — | 69% | — | 80% |
| 73 | 30% | — | 62% | — | 81% |

*Cell viability <70%

Example 41

Stimulation of Glucose Uptake in 3T3-L1 Adipocytes With Compounds of the Present Invention Differentiation of mouse 3T3-L1 adipocytes was carried out using the method of Greenberg A S, et al., J Biol Chem 276:45456-61, 2001. Briefly, 3T3-L1 fibroblasts were differentiated to adipocytes by incubation in DMEM containing 10% FBS, 72 µg/ml porcine insulin, 0.5 mM 3-isobutylmethylxanthine (IBMX) and 400 ng/ml dexamethasone for 2×48 h at 37° C. Differentiated cells were maintained in media containing 10% FBS without insulin, IBMX or dexamethasone until they were used for experiments. The effect of treatment with compounds of the invention on glucose uptake by differentiated adipocytes was assessed essentially according to the method of Tafuri S R, Endocrinology 137:4706-12, 1996. Adipocytes were incubated with vehicle (0.1% DMSO) or test compound (0.1, 1.0 or 10 µM) for 48 h in DMEM containing 10% FBS, then washed and incubated in high-glucose, serum-free medium for 3 h at 37° C. Cells were then washed, incubated for 20 min in glucose-free, serum-free medium containing 100 nM insulin, then supplemented with 2.5 µCi/ml ¹⁴C-deoxyglucose in 0.1 mM cold deoxyglucose and further incubated for 10 min at room temperature. After washing, cells were lysed with 0.5% SDS and the radioactivity was measured in a scintillation counter to determine the amount of glucose uptake. The mean percent stimulation of glucose uptake relative to vehicle (set at 100%) was calculated for each concentration of test compound from triplicate determinations. As shown in Table 3, the compounds of the invention caused significant stimulation of glucose uptake in differentiated adipocytes.

TABLE 3

| Test Compound | Percent Stimulation of Glucose Uptake | | |
|---|---|---|---|
| | 0.1 µM | 1.0 µM | 10 µM |
| 31 | 107% | 119% | 161% |
| 8 | 115% | 132% | 171% |
| 60 | 93% | 120% | 229% |
| 61 | 93% | 120% | 229% |
| 51 | 93% | 107% | 136% |
| 29 | 106% | 124% | 120% |
| 40 | 126% | 117% | 126% |
| 63 | 107% | 112% | 139% |
| 64 | 108% | 113% | 127% |
| 56 | 83% | 100% | 126% |

Example 42

Inhibition of PDE4 and PDE3 Activity With a Compound of the Present Invention

Compound 13 was examined for its ability to inhibit the activity of PDE4 and PDE3 enzymes. PDE4 partially purified from human U-937 promonocytic cells and PDE3 partially purified from human platelets were used. Test compound (1, 10 or 30 µM) or vehicle (0.1% DMSO) was incubated with 0.2 µg PDE4 enzyme or 1 µg PDE3 enzyme and 1 µM cAMP containing 0.01 µg [³H]cAMP in Tris buffer pH 7.5 for 20 min at 30° C. The reaction was terminated by boiling for 2 min and the resulting AMP was converted to adenosine by addition of 10 mg/ml snake venom nucleotidase and further incubation at 30° C. for 10 min. Unhydrolyzed cAMP was bound to AGI-X2 resin, and remaining [³H]adenosine in the aqueous phase was quantitated by scintillation counting. The mean percent inhibition of PDE4 or PDE3 activity was calculated from duplicate determinations (Table 4). Compound 13 exhibited significant inhibition of both PDE4 (IC$_{50}$<1 µM) and PDE3 (IC$_{50}$=13.6 µM) enzyme activities.

TABLE 4

| Enzyme Assay | Percent Inhibition of Enzyme Activity | | |
|---|---|---|---|
| | 1 µM | 10 µM | 30 µM |
| PDE4 | 85% | 98% | 102% |
| PDE3 | 20% | 52% | 55% |

Example 43

Inhibition of LPS-induced Phosphorylation of p44/42 MAP Kinase with a Compound of the Present Invention Compound 13 was examined for its ability to inhibit LPS-induced and LPS/IFN-gamma induced phosphorylation of p44/42 MAP kinase. RAW 264.7 gamma NO(−) cells were seeded at $1\times10^6$/well (2 ml per well) in 6-well tissue culture plates one day prior to the experiment. To start the experiment, cells were washed 2× with RPMI 1640 medium, 0.5% FBS, 100 U/ml penicillin, 100 µg/ml streptomycin, 1 mM sodium pyruvate, and then pretreated with vehicle (0.1% DMSO) or test compound (10 or 30 µM) at 37° C. for 1 h. After pretreatment, cells were incubated in RPMI 1640 medium, 10% FBS, 100 U/ml penicillin, 100 µg/ml streptomycin, 1 mM sodium pyruvate, containing 10 ng/ml LPS or LPS (10 ng/ml)/IFN-gamma (10 U/ml) at 37° C. for 15 min. Cells were then washed 2× with cold PBS (pH 7.4) and lysed in 20 mM Tris-HCl (pH 7.5), 150 mM NaCl, 1 mM $Na_2EDTA$, 1 mM EGTA, 1% Triton, 2.5 mM sodium pyrophosphate, 1 mM beta-glycerophosphate, 1 mM $Na_3VO_4$, 1 µg/ml leupeptin, 1 mM PMSF on ice for 10 min. Lysed cells were collected and centrifuged at ~20,800×g for 10 min at 4° C. Supernatants (lysates) were collected, aliquoted, and stored frozen at −80° C. until use. Lysates (29 µg of total proteins per sample) were subjected to SDS-polyacrylamide (4-20%) gel electrophoresis, and the separated proteins were transferred to nitrocellulose membranes. Membranes were blocked with 5% non-fat dry milk, 10 mM Tris—HCl (pH 8.0), 150 mM NaCl, 0.1% Tween® −20 at room temperature for 1 h and then were blotted with mAb against phospho-p44/42 MAP kinase (Thr 202/Tyr 204) at room temperature for 1 h. The membranes were then washed and incubated with a horseradish peroxidase-linked anti-mouse secondary antibody at room temperature for 1 h. The signals were detected using ECL Western blotting detection reagents. The results showed that compound 13 inhibited LPS-induced phosphorylation of p44/42 MAP kinase at 30 µM but not 10 µM, while the compound inhibited LPS/IFN-gamma induced phosphorylation of p44/42 in a dose-dependent manner at 30 µM and 10 µM (data not shown).

Example 44

Inhibition of Anti-CD3/Anti-CD28 Stimulated Lymphocyte Proliferation with a Compound of the Present Invention Compound 13 was examined for its ability to inhibit anti-CD3/anti-CD28 stimulated lymphocyte proliferation. Binding of antigen, or antibodies, to CD3/CD28 triggers activation and proliferation of T-lymphocytes, which are key steps involved in mounting an immune response (Abbas, Lichtman and Pober, Cellular and Molecular Immunology, $3^{rd}$ edition, W. B. Saunders Company, Philadelphia, 1997). Mesenteric lymph nodes were collected from BALB/c mice (female, ~8 weeks old), and the cells were isolated in PBS (pH 7.4) and mixed with culture medium (RPMI 1640 medium, 10% FBS, 100 U/ml penicillin, 100 µg/ml streptomycin, 50 µM 2-mercaptoethanol). The cell suspension was centrifuged at 900 rpm for 10 min at room temperature using a Beckman GS-6 centrifuge with GH-3.8 rotor. After centrifugation, cell pellets were resuspended in culture medium and centrifuged again at 900 rpm for 10 min at room temperature. Cell pellets were resuspended in culture medium and cells were counted. $2\times10^5$ lymph node cells per well were added into a 96-well cell culture plate. For the treatment (n=4), vehicle (DMSO) or test compound was added into cells. Cells were treated with purified hamster anti-mouse CD3ε (2 µg/ml) and anti-mouse CD28 (0.2 µg/ml) monoclonal antibodies or with culture medium. The final concentrations were 0.1% DMSO and 10 µM test compound in a final volume of 200 µl per well. Cells were incubated at 37° C. for 67 h, and then cells on plates were centrifuged at 900 rpm for 10 min at room temperature using a Beckman GS-6 Centrifuge with GH-3.8 rotor. 150 µl of supernatant from each well was subsequently harvested and frozen at −80° C. for further analysis (ELISA). For the cells on the plate, 150 µl of culture medium was added into each well to replace the harvested supernatants and 40 µl of MTS/PMS solution was added into each well. After further incubation at 37° C. for 140 min, the plate was read at 505 nm in a microplate spectrophotometer. The O.D. values (after subtracting the mean O.D. of blank wells) were used to compare the proliferation of treated cells. As shown in Table 5, 10 µM of compound 13 caused about 50% inhibition of the proliferation of mouse mesenteric lymph node cells stimulated by anti-CD3/anti-CD28 monoclonal antibodies. Inhibition of CD3/CD28 mediated T-cell proliferation demonstrates compound 13 is able to block an immunologically-relevant cellular response, probably via interactions with a step in the signal transduction cascade. This indicates that compound 13 has immunomodulatory activity, which may be useful for the treatment of immunoproliferative disorders.

TABLE 5

| Treatment | O.D. (Mean ± SD) |
|---|---|
| DMSO | 0.020 ± 0.006 |
| DMSO + anti-CD3/anti-CD28 mAbs | 1.372 ± 0.125 |
| Test compound + anti-CD3/anti-CD28 mAbs | 0.578 ± 0.012 |

Example 45

Improvement of Collagen Induced Arthritis in Mice Using a Compound of the Present Invention Collagen-induced arthritis (CIA) was induced in 45 DBA/1J mice using immunization with chicken collagen Type II. The induction schedule was as follows: on Day 0, 100 µg/100 µl in Complete Freund's Adjuvant (CFA) intradermally; on Day 21, 100 µg/100 µl in Incomplete Freund's Adjuvant subcutaneously; on Day 31, 100 µg/100 µl in CFA subcutaneously; all given at the base of the tail. On Day 35 animals received lipopolysaccharides (detoxified from *E. coli* serotype O111:B4; 40 µg/mL) intraperitoneally. When signs of arthritis appeared, mice were assigned into four treatment groups: vehicle control (0.5% carboxymethylcellulose (CMC)); compound 31 (40 mg/kg suspension in CMC); compound 31 (100 mg/kg in CMC); positive control (dexamethasone; 5 mg/kg). The animals were dosed per oral by gavage, twice daily for 14 days, at a dose volume of 250 µl per mouse per dose. The study was scored blindly to the different treatment groups. Mice were weighed and arthritis was scored three times a week. Arthritis was scored as a count of affected limbs and digits, evaluated as: erythema and swelling of tarsal, the ankle to the metatarsal joints, up to restriction of movement and deformity of the joints. Plasma was collected from the animals 4 hours following the final dose, for measurement of circulating drug levels. At termination, animals were euthanized and hind limbs removed for histopathologic examination, hind limbs were collected in formalin. Decalcified tissue was sectioned longitudinally, parallel to the bones, and hematoxylin and eosin stained sections were scored using a standard rheumatoid arthritis scoring system by a veterinary histopathologist who was blinded to the treatment groups. Animals in all groups had moderate arthritis prior to the start of dosing (Day 0) as shown in FIG. 9. The vehicle group exhibited an increase in severity over the course of the study with a tendency to plateau from about Day 10. The low dose of compound 31 had no apparent effect on the animals compared with vehicle controls. The high dose prevented the increase in severity, to about the same extent as dexamethasone. Histology showed that the vehicle group and the low-dose compound 31 group had marked chronic inflammation of synovium with pannus formation and destruction of bone and cartilage, while in the dexamethasone group the joints were within normal limits. At high dose of compound 31 there was a reduction in incidence and severity of pannus formation, inflammation cell infiltration and bone/cartilage damage. Thus a dose-dependent effect of compound 31 was observed on both the soft tissue and bone and cartilage, consistent with a disease-modifying activity of the compound in this model.

It will be evident from the above that the compounds according to the present invention not only lower blood glucose level, triglyceride level and free fatty acid level in diabetic conditions, but also inhibit TNF-alpha, IL-6, IL-1 beta, COX-2 and iNOS production in inflammation, as well as inhibit PDE4 and PDE3 activity, phosphorylation of p44/42 MAP kinase and lymphocyte proliferation. The properties demonstrated above indicate that the compounds of the invention should be useful in the treatment of disorders associated with insulin resistance, hyperglycemia, hyperlipidemia, coronary artery disease and peripheral vascular disease and for the treatment of inflammation, inflammatory diseases, immunological diseases, proliferative diseases and cancer, especially those mediated by cytokines, cyclooxygenase, phosphodiesterase and/or MAP kinase.

Example 46

Synthesis of N-{4-[2-(3,5-dimethoxyphenyl)-1-dimethylcarbamoylvinyl]-phenyl}-benzamide (67)

A mixture of 2-(4-aminophenyl)-3-(3,5-dimethoxyphenyl)-N,N-dimethylacrylamide, 43, (0.49 g, 1.2 mmol) and benzoyl chloride (0.26 g, 1.8 mmol) in anhydrous benzene (18.0 mL) was heated at 90° C. for 2 h. Solvent was evaporated and crude product was purified by silica gel chromatography.

Analysis: $^1$HNMR (DMSO-$d_6$): δ 10.33 (s, 1H), 7.96 (d, J=8.8 Hz, 2H), 7.76 (d, J=8.8 Hz, 1H), 7.51-7.62 (m, 3H), 7.26 (d, J=9.2 Hz, 2H), 6.55 (s, 1H), 6.35 (t, J=2.0 Hz, 1H), 6.31 (d, J=2.0 Hz, 2H), 3.58 (s, 6H), 3.03 (brs, 3H), 2.91 (brs, 3H).

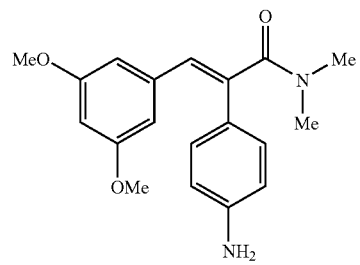

43

-continued

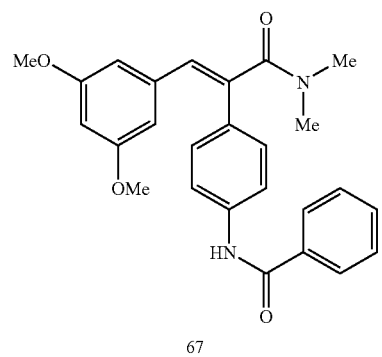

67

Example 47

Synthesis of 3-{4-[4-(2-benzo[1,3]dioxol-5-yl-1-dimethylcarbamoylvinyl)-phenoxy]-Phenyl}-propionic acid ethyl ester (69)

A mixture of 3-{4-[4-(2-ethoxycarbonylethyl)-phenoxy]-phenyl}-2-oxopropionic acid, 24 (1.0 g, 3.0 mmol), piperonal (0.67 g, 0.45 mmol), triethylamine (5.12 mL) and acetic anhydride (5 mL) was heated at 80° C. for 3 h. Reaction mixture was poured in water (50 mL). Solid separated was filtered and boiled in toluene, cooled and filtered. Crude solid was purified by silica gel chromatography to yield 68, 0.35 g (yield, 25.0%).

A mixture of 4-benzo[1,3]dioxol-5-yl-3-{4-[4-(2-ethoxycarbonylethyl)-phenoxy]-phenyl}-2-oxobut-3-enoic acid, 68, (0.08 g, 0.17 mmol), benzotriazol-1-yloxytris-(dimethylamino)-phosphonium hexafluorophosphate (BOP, 0.09 g, 0.21 mmol), triethylamine (36 μL, 0.25 mmol), dimethylamine in THF (2M, 0.25 mL, 0.5 mmol) in DMF (2.0 mL) was stirred for 10 min at room temperature. Reaction mixture was poured in water (20 mL). Solid separated was filtered and boiled in toluene, cooled and filtered. Crude solid was purified by silica gel chromatography to yield 69.

Analysis: $^1$HNMR (DMSO-$d_6$): δ 7.24 (d, J=8.8 Hz, 4H), 6.95 (overlapped d, J=8.8 Hz, 4H), 6.80 (d, J=8.0 Hz, 1H), 6.68 (d, J=8.0 Hz, 1H), 6.54 (s, 1H), 6.51 (s, 1H), 5.96 (s, 2H), 4.05 (q, J=4.0 Hz, 2H), 3.05 (brs, 3H), 2.85 (brs, 3H), 2.80 (t, J=6.0 Hz, 2H), 2.60 (t, J=6.0 Hz, 2H) and 1.15 (t, J=4.0 Hz, 3H).

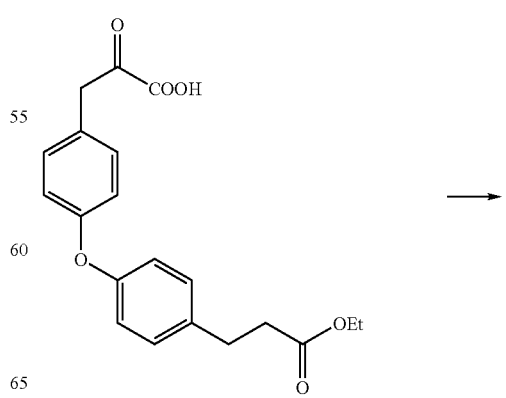

24

-continued

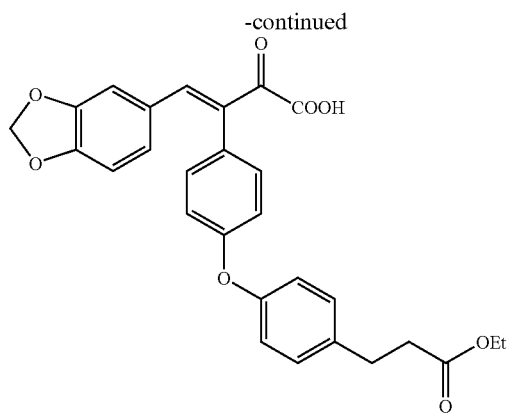

68

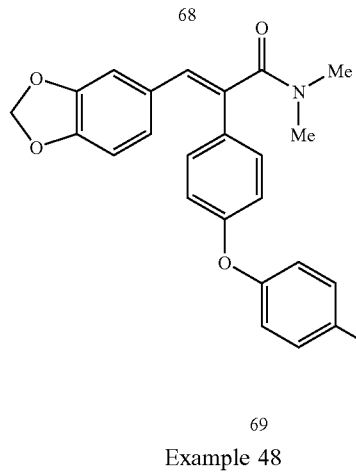

69

Example 48

Synthesis of 2-{4-[4-(1-dimethylcarbamoyl-2-pyridin-3-ylvinyl)-phenoxy]-benzyl}-malonamide (71)

To a solution of 2-{4-[4-(1-dimethylcarbamoyl-2-pyridin-3-ylvinyl)-phenoxy]-benzyl}-malonic acid dimethyl ester, 70 (0.49 g, 1.0 mmol), in DMF (5 mL), ammonium hydroxide (28% in water, 12 mL) was added and stirred overnight at room temperature. Reaction mixture was poured in water (30 mL) and extracted with chloroform (5×25 mL). The organic layer was dried on anhydrous magnesium sulfate and evaporated. The crude product was purified by silica gel chromatography to yield 71, 0.23 g (yield, 24.5%).

Analysis: $^1$HNMR (CDCl$_3$+CD$_3$OD): δ 8.32 (m, 2H), 7.40 (m, 1H), 7.18 (overlapped d, J=8.0 Hz, 2H), 7.20 (overlapped d, J=8.0 Hz, 2H), 7.12 (m,1H), 6.92 (d, J=8.0 Hz, 2H), 6.84 (d, J=8.0 Hz, 2H), 6.60 (s, 1H), 3.22 (d, J=12.0 Hz), 3.12 (brd, J=12.0 Hz), 2.98 (brs, 3H), 2.96 (brs, 3H).

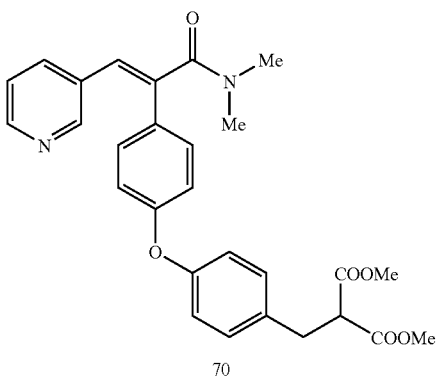

70

-continued

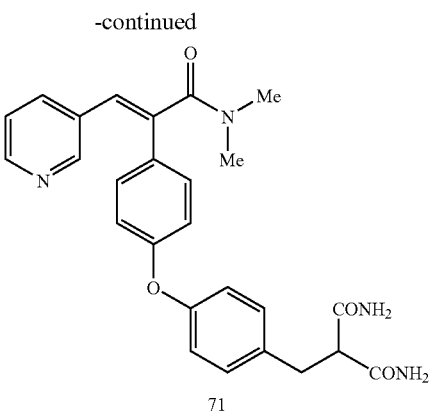

71

Example 49

Synthesis of N,N-dimethyl-2-{4-[4-(3-oxo-3-ureidopropyl)-phenoxy]-phenyl}-3-pyridin-3-yl-acrylamide (73)

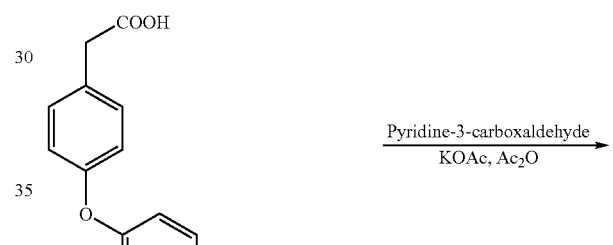

24

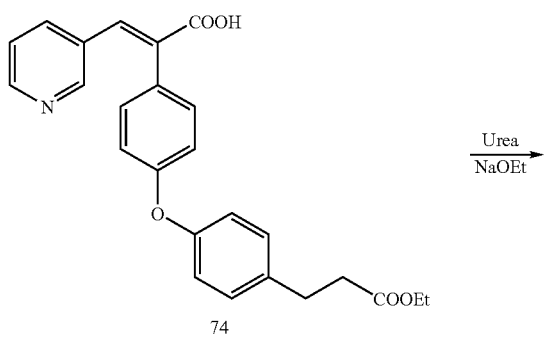

74

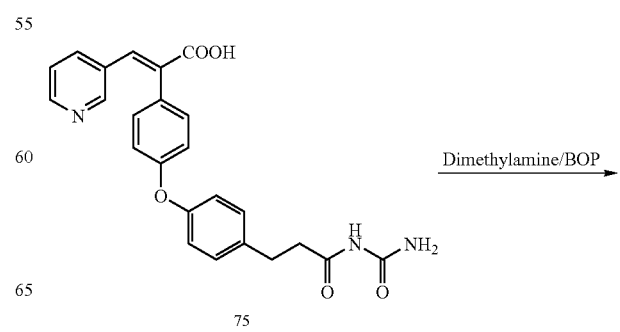

75

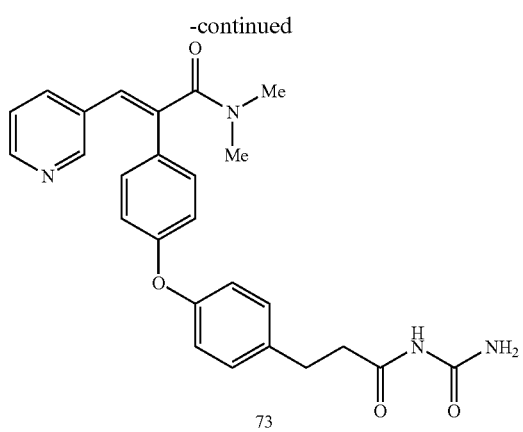

(a) Step 1: Synthesis of 2-{4-[4-(2-ethoxycarbonylethyl)-phenoxy]-phenyl}-3-pyridin-3-yl-acrylic acid (74). To a solution of 3-[4-(4-carboxymethylphenoxy)-phenyl]-propionic acid ethyl ester, 24, (14.94 g, 45.56 mmol) in DMF (100 mL) pyridine 3-carboxaldehyde (5.12 g, 47.84 mmol), potassium acetate (5.37 g, 54.67 mmol) and acetic anhydride (5.09 g, 49.09 mmol) were added and heated at 100° C. for 90 min. To the reaction mixture acetic acid (4.13 g, 68.34 mmol) and water (1 L) was added and extracted with ethyl acetate (3×400 mL). Organic layer was washed with water, brine, dried on anhydrous magnesium sulfate and evaporated. Crude product was purified by silica gel chromatography and eluted with ethyl acetate-acetic acid (99:1). Yield: 9.02 g (47.5%).

$^1$HNMR (DMSO-$d_6$): δ 12.91 (s, 1H), 8.39 (dd, J=4.8 & 1.6 Hz, 1H), 8.33 (d, J=2.0 Hz, 1H), 7.34 (dt, J=8.0 & 2.0 Hz, 1H), 7.25 (m, 3H), 7.15 (d, J=8.0 Hz, 2H), 6.97 (d, J=8.8 Hz, 2H), 6.95 (d, J=8.8 Hz, 2H), 4.02 (q, J=7.6 Hz, 2H), 2.83 (t, J=7.2 Hz, 2H), 2.60 (t, J=7.6 Hz, 2H), 1.13 (t, J=7.6 Hz).

(b) Step 2: Synthesis of 2-{4-[4-(3-oxo-3-ureidopropyl)-phenoxy]-phenyl}-3-pyridin-3-yl-acrylic acid (75). A mixture of sodium ethoxide (21% w/w, 30 mL) and ethyl acetate (1.0 mL) was refluxed for 30 min. Mixture was cooled down to 80° C., urea (4.81 g, 80.4 mmol) was added and heated till it dissolved completely. 2-{4-[4-(2-ethoxycarbonylethyl)-phenoxy]-phenyl}-3-pyridin-3-yl-acrylic acid, 74, (6.0 g, 14.3 mmol) was added and heated for 5 min. Reaction mixture was cooled, neutralized by trifluoroacetic acid and water (50 mL) was added. Solid separate was purified by repeated crystallization from ethyl acetate-methanol mixture. Yield: 2.91 g (46.9%).

$^1$HNMR (DMSO-$d_6$): δ 12.90 (s, 1H), 10.16 (s, 1H), 8.40 (dd, J=4.8 & 2.0 Hz, 1H), 8.32 (d, J=2.4 Hz, 1H), 7.76 (s, 1H), 7.68 (br, 1H), 7.40 (dt, J=8.0 & 2.0 Hz, 1H), 7.24-7.21 (m, 4H), 7.15 (d, J=8.0 Hz, 2H), 6.97 (d, J=8.8 Hz, 2H), 6.95 (d, J=8.4 Hz, 2H), 2.81 (t, J=7.2 Hz, 2H), 2.58 (t, J=7.6 Hz, 2H).

(c) Step 3: Synthesis of N,N-dimethyl-2-{4-[4-(3-oxo-3-ureidopropyl)-phenoxy]-phenyl}-3-pyridin-3-yl-acrylamide (73). To a solution of 2-{4-[4-(3-oxo-3-ureidopropyl)-phenoxy]-phenyl}-3-pyridin-3-yl-acrylic acid, 75, (2.70 g, 6.2 mmol) in DMF (10 mL) triethylamine (1.29 mL, 9.3 mmol) and BOP (3.0 g, 6.88 mmol) reagent was added and stirred at room temperature for 15 min. Dimethylamine (2.0 M in THF, 9.3 mL, 18.6 mmol) was added and stirred for another 15 min. Reaction mixture was poured into ice cold water (100 mL) and extracted with ethyl acetate (3×50 mL). Combined organic layer was washed with aqueous sodium hydroxide solution (0.5 M, 30 mL), water (3×50 mL), brine (2×50 mL), dried on anhydrous magnesium sulfate and concentrated to about one third of original volume. Solid separated was filtered and washed with ethyl acetate. Yield: 2.81 g (97.9%).

$^1$HNMR (DMSO-$d_6$): δ 10.16 (s, 1H), 8.36 (dd, J=4.8 & 1.6 Hz, 1H), 8.31 (d, J=2.4 Hz, 1H), 7.72 (br, 1H), 7.43 (dt, J=8.0 & 2.0 Hz, 1H), 7.26-7.21 (m, 6H), 6.97 (d, J=8.0 Hz, 2H), 6.93 (d, J=8.4 Hz, 2H), 6.65 (s, 1H), 3.03 (s, 3H), 2.90 (s, 3H), 2.81 (t, J=7.6 Hz, 2H), 2.58 (t, J=8.0 Hz, 2H).

Example 50

Synthesis of 2-{4-[4-(2-carbamoyl-ethyl)-phenoxy]-phenyl}-N,N-dimethyl-3-pyridin-3-yl-acrylamide (77)

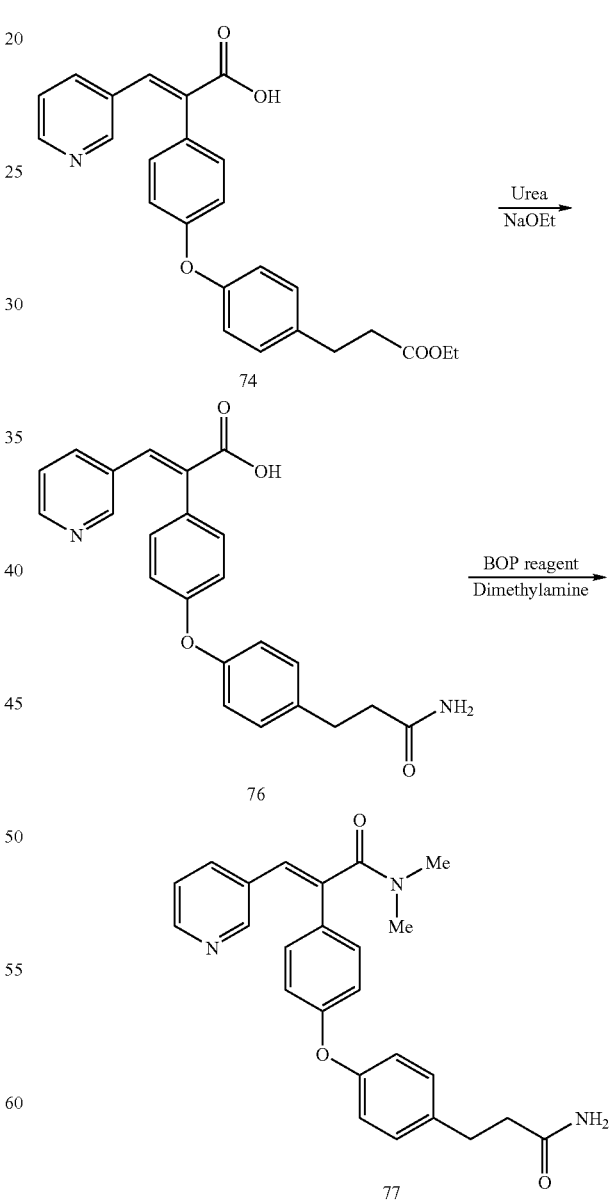

(a) Step 1: Synthesis of 2-f 4-F4-(2-carbamoylethyl)-phenoxyl -phenyl]-3-pyridin-3-yl-acrylic acid (76). A mixture of sodium ethoxide (21% w/w, 12 mL) and ethyl acetate (0.7 mL) was refluxed for 30 min. Urea (1.92 g, 32.0 mmol) was added and heated till it dissolved completely. 2-{4-[4-(2-ethoxycarbonyl-ethyl)-phenoxy]-phenyl}-3-pyridin-3-yl-acrylic acid, 74, (2.40 g, 5.7 mmol) was added and heated for 90 min at reflux. Reaction mixture was cooled to room temperature, neutralized by trifluoroacetic acid and water (50 mL) was added. Solid separate was purified by repeated crystallization from hot ethyl acetate. Yield: 2.2 g (97.6%).

$^1$HNMR (DMSO-d$_6$): δ 12.90 (s, 1H), 8.40 (dd, J=5.2 & 2.0 Hz, 1H), 8.33 (d, J=2.0 Hz, 1H), 7.76 (s, 1H), 7.36 (dt, J=8.0 & 2.0 Hz, 1H), 7.29 (br, 1H), 7.27-7.23 (m, 3H), 7.15 (d, J=8.0 Hz, 2H), 6.96 (overlapped d, J=8.0, 4H), 6.78 (br,1H), 2.78 (t, J=7.2 Hz, 2H), 2.33 (t, J=7.6 Hz, 2H).

(b) Step 2: Synthesis of 2-{4-[4-(2-carbamoyl-ethyl)-phenoxy]-phenyl}-N,N-dimethyl-3-pyridin-3-yl-acrylamide (77). To a solution of 2-{4-[4-(2-carbamoyl-ethyl)-phenoxy]-phenyl}-3-pyridin-3-yl-acrylic acid, 76, (2.00 g, 5.1 mmol) in DMF (5 mL) triethylamine (1.06 mL, 7.6 mmol) and BOP reagent (2.5 g, 5.66 mmol) were added and stirred at room temperature for 15 min. Dimethylamine (2.0 M in THF, 7.65 mL, 15.3 mmol) was added and stirred for another 15 min. Reaction mixture was poured into ice cold water (100 mL) and extracted with ethyl acetate (4×50 mL). Combined organic layer was washed with saturated aqueous sodium bicarbonate solution (30 mL), water (3×50 mL), brine (2×50 mL), dried on anhydrous magnesium sulfate. Crude product was purified by silica gel chromatography and product was eluted with chloroform-methanol (19:1). Yield: 1.4 g (65.4%).

$^1$HNMR (DMSO-d$_6$): δ 8.36 (dd, J=4.8 & 1.6 Hz, 1H), 7.43 (dt, J=8.0 & 2.0 Hz, 1H), 7.28 (br, 1H), 7.26-7.21 (m, 5H), 6.95 (d, J=8.8 Hz, 2H), 6.92 (d, J=8.8 Hz, 2H), 6.77 (br, 1H), 6.65 (s, 1H), 3.03 (s, 3H), 2.90 (s, 3H), 2.77 (t, J=7.6 Hz, 2H), 2.33 (t, J=8.0 Hz, 2H).

-continued

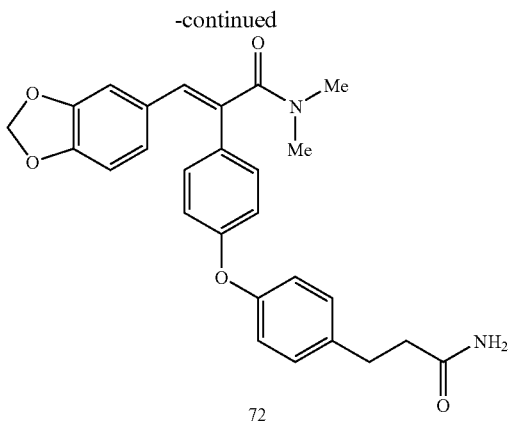

72

To a solution of 3-benzo[1,3]dioxol-5-yl-2-{4-[4-(2-carbamoylethyl)-phenoxy]-phenyl}-acrylic acid, 78, (2.00 g, 4.6 mmol) in DMF (10 mL) triethylamine (0.96 mL, 6.9 mmol) and BOP reagent (2.21 g, 5.0 mmol) were added and stirred at room temperature for 15 min. Dimethylamine (2.0 M in THF, 6.90 mL, 1.8 mmol) was added and stirred for another 15 min. Reaction mixture was poured into ice cold water (100 mL) and extracted with ethyl acetate (4×50 mL). Combined organic layer was washed with saturated aqueous sodium bicarbonate solution (30 mL), water (3×50 mL), brine (2×50 mL), dried on anhydrous magnesium sulfate. Crude product was purified by silica gel chromatography and product was eluted with chloroform-methanol (19:1). Yield: 1.91 g (90.0%).

$^1$HNMR (DMSO-d$_6$): δ 7.28 (br, 1H), 7.24 (d, J=7.6 Hz, 2H), 6.94 (d, J=8.4 Hz, 2H), 6.93 (d, J=8.4 Hz, 2H), 6.80 (d, J=8.4 Hz, 1H), 6.77 (br, 1H), 6.68 (dd, J=8.4 and 1.6 Hz, 1H), 6.52 (s, 1H), 6.50 (d, 1.6 Hz, 1H), 5.96 (s, 2H), 3.00 (s, 3H), 2.87 (s, 3H), 2.77 (t, J=8.0 Hz, 2H).

Example 51

Synthesis of 3-benzo[1,3]dioxol-5-yl-2-{4-[4-(2-carbamoyl-ethyl)-phenoxy]-phenyl}-N,N-dimethyl-acrylamide (72)

Example 52

Synthesis of 2-{4-[4-(2-carbamoylethyl)-phenoxy]-phenyl}-N,N-dimethyl-3-pyridin-3-yl-propionamide (81)

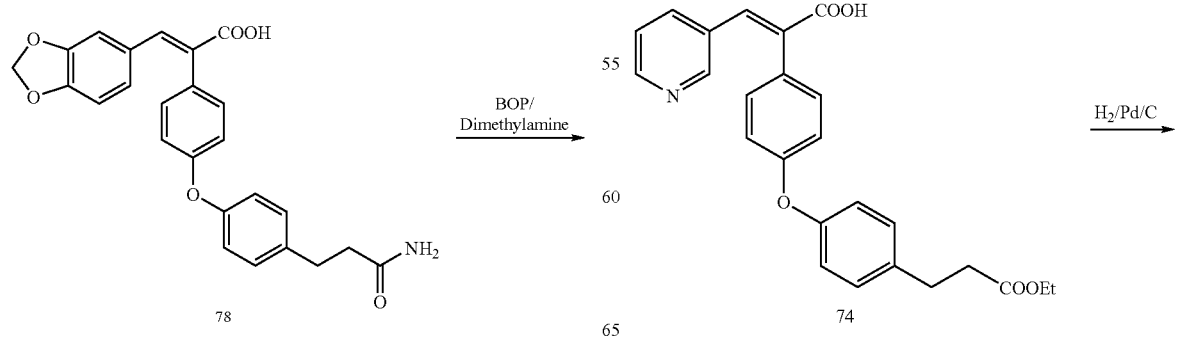

-continued

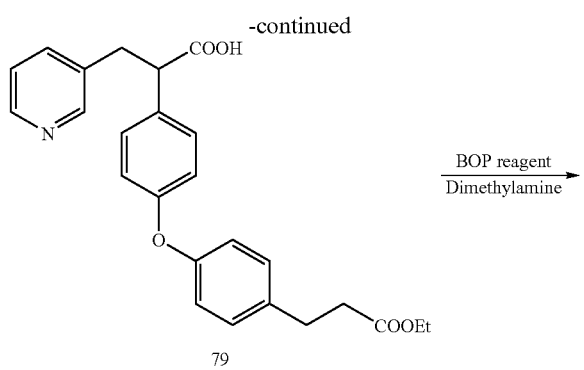

79

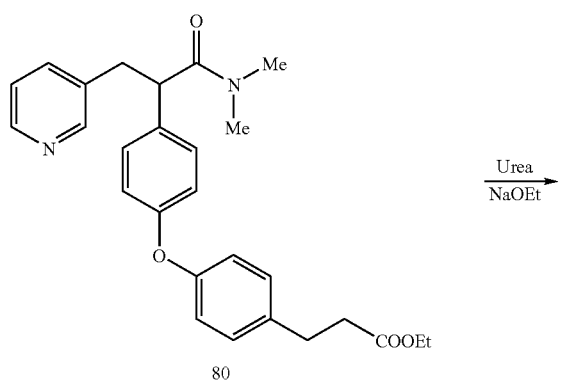

80

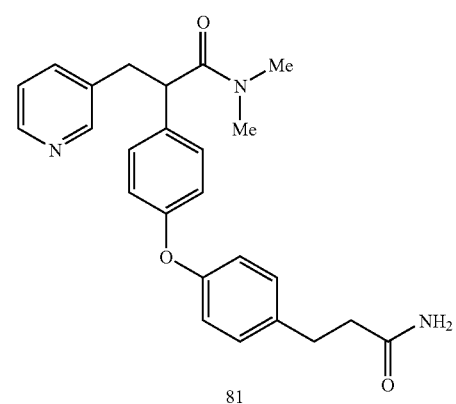

81

(a) Step 1: Synthesis of 2-{4-[4-(2-ethoxycarbonylethyl)-phenoxy]-phenyl}-3-pyridin-3-ylpropionic acid (79). To a solution of 2-{4-[4-(2-ethoxycarbonyl-ethyl)-phenoxy]-phenyl}-3-pyridin-3-yl-acrylic acid, 74, (6.00 g, 14.3 mmol) in 1,4-dioxane-ethanol (1:1, 80 mL) palladium on carbon (300 mg) was added, degassed and charged with hydrogen and stirred overnight. Catalyst was filtered and solvent was evaporated. Product obtained was used without further purification. Yield: 5.4 g (90.0%).

$^1$HNMR (DMSO-$d_6$): δ 8.35-8.33 (m, 2H), 7.58 (dt, J=7.6 & 2.0 Hz, 1H), 7.28 (d, J=8.8 Hz, 2H), 7.26-7.24 (m, 1H), 7.21 (d, J=8.4 Hz, 2H), 6.88 (d, J=8.8 Hz, 4H), 4.03 (q, J=6.8 Hz, 2H), 3.85 (t, J=7.6 Hz, 1H), 3.24 (dd, J=14.0 & 8.4 Hz, 1H), 2.93 (dd, J=13.6 & 7.2 Hz, 1H), 2.81 (t, J=7.6 Hz, 2H), 2.59 (t, J=7.6 Hz, 2H), 1.14 (t, J=6.8 Hz, 3H).

(b) Step 2: Synthesis of 3-{4-[4-(1-dimethylcarbamoyl-2-pyridin-3-ylethyl)-phenoxy]-phenyl}-propionic acid ethyl ester (80). To a solution of 2-{4-[4-(2-ethoxycarbonylethyl)-phenyl}-3-pyridin-3-ylpropionic acid, 79 (5.40 g, 12.8 mmol) in DMF (15 mL) triethylamine (2.60 mL, 19.2 mmol) and BOP reagent (6.20 g 14.1 mmol) was added and stirred at room temperature for 15 min. Dimethylamine (2.0 M in THF, 19.20 mL, 38.4 mmol) was added and stirred for another 10 min. Reaction mixture was poured into ice cold water (100 mL) and extracted with ethyl acetate (4×100 mL). Combined organic layer was washed with saturated aqueous sodium bicarbonate solution (2×100 mL), water (2×100 mL), brine (100 mL), dried on anhydrous magnesium sulfate. Crude product was purified by silica gel chromatography and product was eluted with chloroform-methanol (19:1). Yield: 4.80 g (83.5%).

$^1$HNMR (DMSO-$d_6$): δ 8.34-8.32 (m, 2H), 7.54 (dt, J=7.6 & 2.0 Hz, 1H), 7.26-7.21 (m, 5H), 6.88 (d, J=8.4 Hz, 4H), 4.28 (t, J=7.2 Hz, 1H), 4.03 (q, J=6.8 Hz, 2H), 3.21 (dd, J=14.0 & 8.4 Hz, 1H), 2.84 (s, 3H), 2.81 (t, J=7.2 Hz, 2H), 2.75 (s, 3H), 2.59 (t, J=7.6 Hz, 2H), 1.14 (t, J=6.8 Hz, 3H).

(c) Step 3: Synthesis of 2-{4-[4-(2-carbamoylethyl)-phenoxy]-phenyl}-N,N-dimethyl-3-pyridin-3-yl-propionamide (81). A mixture of sodium ethoxide (21% w/w, 7.46 mL, 20.0 mmol) and ethyl acetate (0.6 mL) was refluxed for 30 min. Urea (1.20 g, 20.0 mmol) was added and heated till it dissolved completely. 3-{4-[4-(1-Dimethylcarbamoyl-2-pyridin-3-ylethyl)-phenoxy]-phenyl}-propionic acid ethyl ester, 80, (1.60 g, 3.58 mmol) was added and heated for 90 min at reflux. Reaction mixture was cooled to room temperature, neutralized by trifluoroacetic acid and water (30 mL) was added and extracted with ethyl acetate (3×50 mL). Organic layer was washed with water (2×20 mL) and brine (50 mL). The compound was purified by silica gel chromatography and product was eluted with chloroform-methanol (19:1). Yield: 0.44 g (40.6%).

$^1$HNMR (DMSO-$d_6$): δ 8.34-8.30 (m, 2H), 7.53 (dt, J=7.6 & 2.0 Hz, 1H), 7.29 (br, 1H), 7.25 (d, J=8.8 Hz, 2H), 7.22 (m, 1H), 7.19 (d, J=8.8 Hz, 2H), 6.87 (d J=8.8 Hz, 2H), 6.77 (br, 1H), 4.27 (t, J=7.2 Hz, 1H), 3.21 (dd, J=13.6 & 8.0 Hz, 1H), 2.84 (s, 3H), 2.83 (dd, J=13.6 & 6.8 Hz, 1H), 2.76 (t, J=7.6 Hz, 2H), 2.75 (s, 3H), 2.32 (t, J=7.6 Hz, 2H).

Example 53

Synthesis of N,N-dimethyl-2-{4-[4-(3-oxo-3-ureido-propyl)-phenoxy]-phenyl}-3-pyridin-3-yl-propionamide (82)

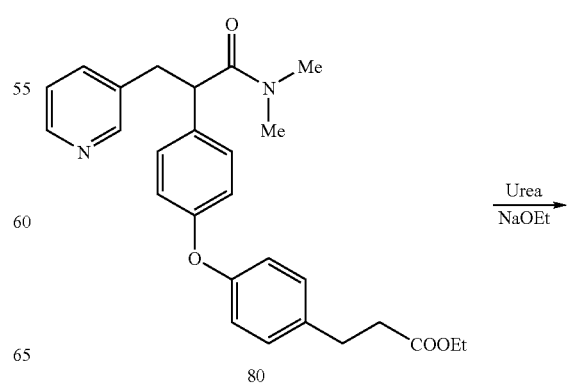

80

-continued

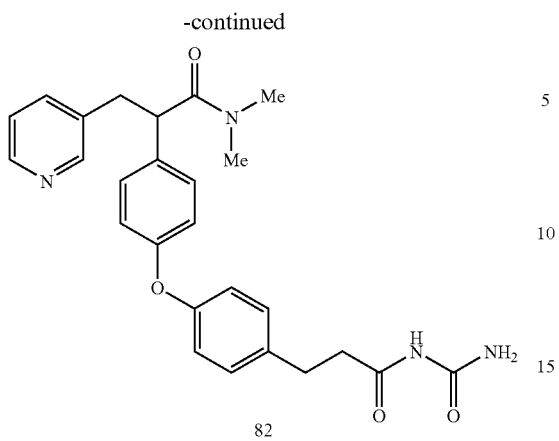

A mixture of sodium ethoxide (21% w/w, 8.10 mL, 21.8 mmol) and ethyl acetate (0.6 mL) was refluxed for 30 min. Urea (1.30 g, 21.8 mmol) was added and heated till it dissolved completely. 3-{4-[4-(1-Dimethylcarbamoyl-2-pyridin-3-ylethyl)-phenoxy]-phenyl}-propionic acid ethyl ester, 80 (1.74 g, 3.80 mmol) was added and heated for 5 min at 80° C. Reaction mixture was cooled to room temperature, neutralized by trifluoroacetic acid and water (50 mL) was added and extracted with ethyl acetate (3×50 mL). Organic layer was washed with water (2×20 mL) and brine (50 mL). The compound was purified by silica gel chromatography and product was eluted with chloroform-methanol (97:3). Yield: 0.30 g (16.7%).

$^1$HNMR (DMSO-d$_6$): δ 10.17 (s, 1H), 8.34-8.31 (m, 2H), 7.22 (br, 1H), 7.53 (dt, J=7.6 & 2.0 Hz, 1H), 7.27-7.19 (m, 6H), 6.89 (d, J=8.8 Hz, 2H), 6.88 (d, J=8.8 Hz, 2H), 4.28 (t, J=7.2 Hz, 1H), 3.21 (dd, J=13.6 & 8.0 Hz, 1H), 2.84 (s, 3H), 2.86-2.78 (m, 3H), 2.75 (s, 3H), 2.57 (t, J=8.4 Hz, 2H).

Example 54

Synthesis of 3-(3,5-dimethoxyphenyl)-N,N-dimethyl-2-{4-[4-(3-oxo-3-ureidopropyl)-phenoxy]-phenyl}-acrylamide (83)

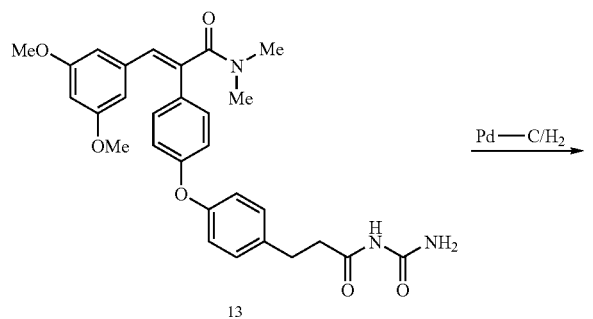

-continued

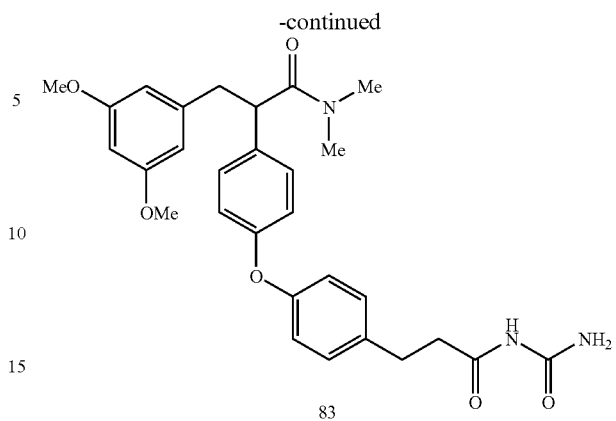

To a solution of 3-(3,5-dimethoxyphenyl)-N,N-dimethyl-2-{4-[4-(3-oxo-3-ureidopropyl)-phenoxy]-phenyl}-propionamide, 13 (0.50 g, 0.96 mmol) in acetic acid (10 mL) palladium on carbon (10%, wet) and ammonium formate (3.3 g, 53.1 mmol) was added and refluxed for 6 h. Catalyst was filtered and the product was crashed out by addition of water (30 mL). Solid was filtered and recrystallized from ethyl acetate. Yield 0.13 g (26.0%)

$^1$HNMR (DMSO-d$_6$): δ 10.16 (s, 1H), 7.74 (br, 1H), 7.27 (d, J=8.8 Hz, 2H), 7.21 (d, J 8.8 Hz, 2H), 6.90 (d, J=8.8 Hz, 2H), 6.88 (d, J=8.8 Hz, 2H), 6.27 (brs, 3H), 4.23 (t, J=7.6 Hz, 1H), 3.66 (s, 6H), 3.17 (dd, J=13.6 & 8.0 Hz, 1H), 2.88 (s, 3H), 2.81 (t, J=8.4 Hz, 2H), 2.78 (s,3H), 2.75 (dd, J=13.6 & 6.8 Hz,1H), 2.59 (t, 2H).

Example 55

Inhibition of LPS-Induced TNF-alpha Production in Mice Using Compounds of the Present Invention DBA/LacJ mice, six to eight weeks old, were administered orally compound 31 (50 or 100 mg/kg), compound 77 (50 or 100 mg/kg), methotrexate (10 mg/kg) as a positive control, or vehicle only (8% dimethyl sulfoxide [DMSO]/42% Solutol® HS-15). After one hour mice were challenged intraperitoneally with lipopolysaccharides (LPS) (3 mg/kg), and one hour after LPS challenge heparinized whole blood was collected by retro-orbital bleed and the plasma was isolated for analysis of tumor necrosis factor-alpha (TNF-alpha) content. Plasma TNF-alpha was measured using a commercial sandwich enzyme-linked immunoassay (ELISA) kit (R&D Systems) employing recombinant murine TNF-alpha to generate a standard curve. The mean value of triplicate determinations was calculated and expressed as a percentage of LPS-induced TNF-alpha production with vehicle (=100%). Statistical analysis was performed using a one-tailed, unpaired t-test with GraphPad Prism software. As shown in Table 6, both compounds 31 and 77 significantly inhibited LPS-induced TNF-alpha production in mice.

TABLE 6

| Treatment | Percent TNF Production (Mean ± SEM)* |
| --- | --- |
| Vehicle (DMSO/Solutol) (n = 7) | 100 ± 9 |
| Compound 77 (50 mg/kg) (n = 3) | 54 ± 10 |
| Compound 77 (100 mg/kg) (n = 5) | 67 ± 20 |

TABLE 6-continued

| Treatment | Percent TNF Production (Mean ± SEM)* |
|---|---|
| Compound 31 (50 mg/kg) (n = 3) | 68 ± 11 |
| Compound 31 (100 mg/kg) (n = 4) | 53 ± 20 |
| Methotrexate (10 mg/kg) (n = 3) | 61 ± 5 |

*All mean values p < 0.05 versus vehicle (unpaired t-test, one-tailed)

Having described specific embodiments of the present invention, it will be understood that many modifications thereof will readily appear or may be suggested to those skilled in the art, and it is intended therefore that this invention is limited only by the spirit and scope of the following claims.

What is claimed is:

1. A compound, or salt, hydrate or solvate thereof, represented by at least one of the following Formulas I, III, VI, VII, IX and XIII:

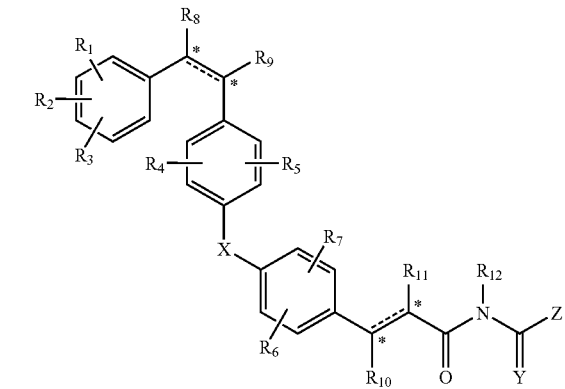

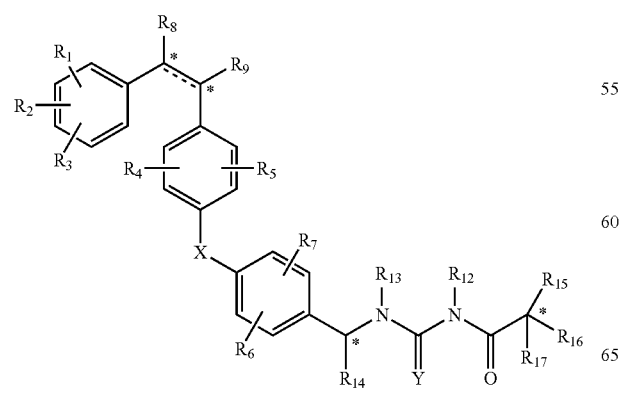

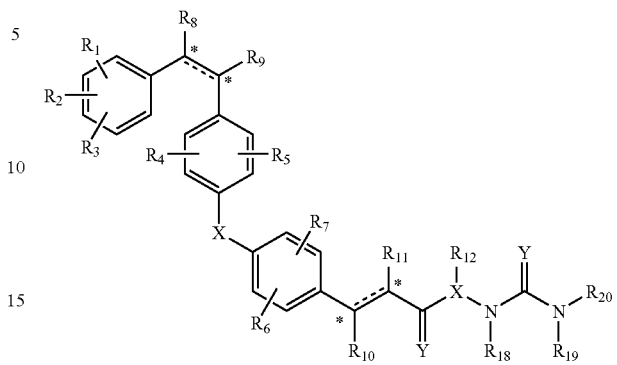

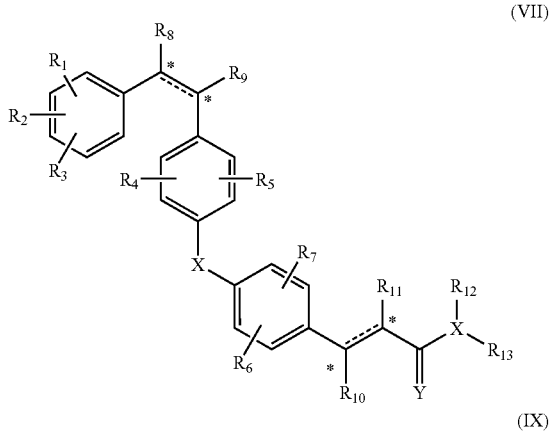

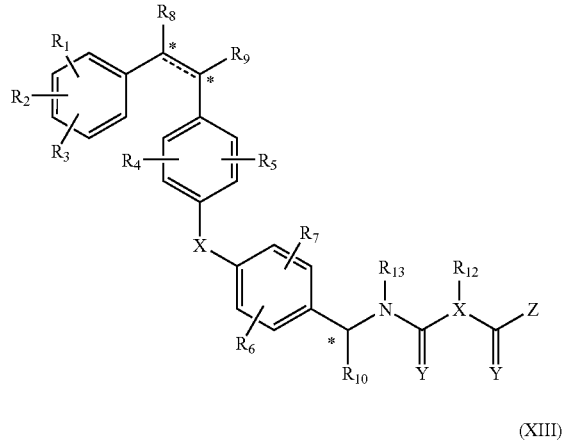

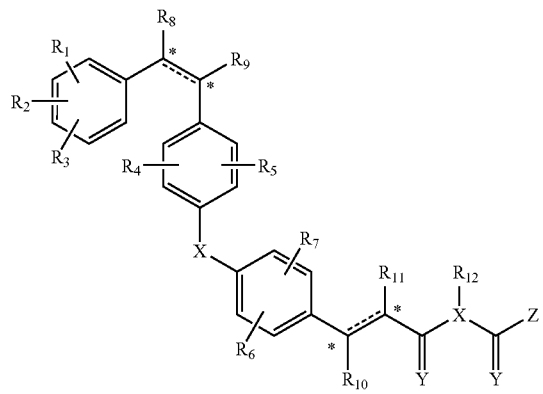

wherein the stereocenters marked with an asterisk (*) are R— or S—; the bond represented by a dashed line plus a solid line is a double bond or a single bond; and wherein $R_1$, $R_2$, $R_3$, $R_4$, $R_5$, $R_6$ and $R_7$ independently represent a hydrogen atom, or an optionally substituted $C_1$-$C_{20}$ linear or branched alkyl, chloroalkyl or fluoroalkyl; optionally substituted $C_2$-$C_{20}$ linear or branched alkenyl; optionally substituted $C_6$-$C_{20}$ aryl, linear or branched alkylaryl, linear or branched alkenylaryl; COOR where R independently represents a hydrogen atom, or an optionally substituted $C_1$-$C_{20}$ alkyl, optionally substituted $C_2$-$C_{20}$ alkenyl or optionally substituted $C_6$-$C_{10}$ aryl, or a pharmaceutically acceptable counter-ion; CONR'R", where R' and R" independently represent a hydrogen atom, or an optionally substituted $C_1$-$C_{20}$ alkyl, optionally substituted $C_2$-$C_{20}$ alkenyl or optionally substituted $C_6$-$C_{10}$ aryl; optionally substituted $C_1$-$C_6$ amidoalkyl; $NH_2$; $C_1$-$C_{20}$ alkylamino, bis(alkylamino) or cycloalkylamino; OH; optionally substituted $C_1$-$C_{20}$ alkoxy, optionally substituted $C_1$-$C_{20}$ alkanoyl; optionally substituted $C_1$-$C_{20}$ acyloxy; halo; optionally substituted $C_1$-$C_{20}$ alkylcarboxylamino; cyano; nitro; $SO_2NR'''R''''$ where R''' and R'''' are independently H, $C_1$-$C_{20}$ alkyl or aryl; $SO_2R'''$ where R'''' is H, $C_1$-$C_{20}$ alkyl or aryl; or $SO_3R'''$ where R''' is H, $C_1$-$C_{20}$ alkyl or aryl;

$R_8$ and $R_9$ independently represent a hydrogen atom, or an optionally substituted $C_1$-$C_{20}$ linear or branched alkyl; optionally substituted $C_2$-$C_{20}$ linear or branched alkenyl; optionally substituted $C_6$-$C_{10}$ aryl; COOR where R is H, optionally substituted $C_1$-$C_{20}$ alkyl, optionally substituted $C_2$-$C_{20}$ alkenyl or optionally substituted $C_6$-$C_{10}$ aryl, or a pharmaceutically acceptable counter-ion; CONR'R", where R' and R" are independently H, alkoxy, optionally substituted $C_1$-$C_{20}$ alkyl, optionally substituted $C_2$-$C_{20}$ alkenyl, optionally substituted $C_3$-$C_{10}$ cycloalkyl or cycloalkenyl or optionally substituted $C_6$-$C_{10}$ aryl; $NH_2$; $C_1$-$C_{20}$ alkylamino, bis(alkylamino) or cycloalkylamino; OH; $C_1$-$C_{20}$ alkoxy; $C_1$-$C_{20}$ alkanoyl; $C_1$-$C_{20}$ acyloxy; halo; $C_1$-$C_{20}$ alkylcarboxylamino; cyano; nitro; $SO_2NR'''R''''$ where R''' and R'''' are independently H, $C_1$-$C_{20}$ alkyl or aryl; $SO_2R'''$ where R''' is H, $C_1$-$C_{20}$ alkyl or aryl; or $SO_3R'''$ where R''' is H, $C_1$-$C_{20}$ alkyl or aryl;

$R_{10}$ and $R_{11}$ independently represent a hydrogen atom or an optionally substituted $C_1$-$C_{20}$ linear or branched alkyl; optionally substituted $C_2$-$C_{20}$ linear or branched alkenyl; optionally substituted $C_6$-$C_{10}$ aryl; COOR where R represents a hydrogen atom or an optionally substituted $C_1$-$C_{20}$ alkyl, optionally substituted $C_2$-$C_{20}$ alkenyl or optionally substituted $C_6$-$C_{10}$ aryl, or a pharmaceutically acceptable counter-ion; CONR'R", where R' and R' independently represent a hydrogen atom, optionally substituted $C_1$-$C_{20}$ alkyl, optionally substituted $C_2$-$C_{20}$ alkenyl or optionally substituted $C_6$-$C_{10}$ aryl; $NH_2$; $C_1$-$C_{20}$ alkylamino, bis(alkylamino) or cycloalkylamino; OH; $C_1$-$C_{20}$ alkoxy; $C_1$-$C_{20}$ alkanoyl; $C_1$-$C_{20}$ acyloxy; halo; $C_1$-$C_{20}$ alkylcarboxylamino; cyano; nitro; $SO_2NR'''R''''$ where R''' and R'''' independently represent a hydrogen atom, $C_1$-$C_{20}$ alkyl or aryl; $SO_2R'''$ where R''' represents a hydrogen atom, $C_1$-$C_{20}$ alkyl or aryl; or $SO_3R'''$ where R''' represents a hydrogen atom, $C_1$-$C_{20}$ alkyl or aryl;

$R_{12}$, $R_{13}$, $R_{18}$, $R_{19}$ and $R_{20}$ independently represent a hydrogen atom; or an optionally substituted $C_1$-$C_{20}$ linear or branched alkyl; optionally substituted $C_2$-$C_{20}$ linear or branched alkenyl; optionally substituted $C_6$-$C_{10}$ aryl; COOR where R represents an optionally substituted $C_1$-$C_{20}$ alkyl, optionally substituted $C_2$-$C_{20}$ alkenyl or optionally substituted $C_6$-$C_{10}$ aryl, or a pharmaceutically acceptable counter-ion; CONR'R", where R'' and R''' independently represent a hydrogen atom, optionally substituted $C_1$-$C_{20}$ alkyl, optionally substituted $C_2$-$C_{20}$ alkenyl or optionally substituted $C_6$-$C_{10}$ aryl; $C_1$-$C_{20}$ alkanoyl; $C_1$-$C_{20}$ alkylamido; $C_6$-$C_{20}$ aroyl; or $SO_2R'''$ where R''' represents a hydrogen atom, $C_1$-$C_{20}$ alkyl or aryl;

$R_{12}$ and $R_{13}$ may be absent;

$R_{14}$ represents a hydrogen atom, or an optionally substituted $C_1$-$C_{20}$ linear or branched alkyl including chloroalkyl and fluoroalkyl; optionally substituted $C_2$-$C_{20}$ linear or branched alkenyl; optionally substituted $C_6$-$C_{10}$ aryl; COOR where R represents a hydrogen atom, optionally substituted $C_1$-$C_{20}$ alkyl, optionally substituted $C_2$-$C_{20}$ alkenyl or optionally substituted $C_6$-$C_{10}$ aryl, or a pharmaceutically acceptable counter-ion; CONR'R", where R' and R" independently represent a hydrogen atom, or an optionally substituted $C_1$-$C_{20}$ alkyl, optionally substituted $C_2$-$C_{20}$ alkenyl or optionally substituted $C_6$-$C_{10}$ aryl; or cyano;

$R_{15}$, $R_{16}$ and $R_{17}$ independently represent a hydrogen atom, or an optionally substituted $C_1$-$C_{20}$ linear or branched alkyl including chloroalkyl and fluoroalkyl; optionally substituted $C_2$-$C_{20}$ linear or branched alkenyl; optionally substituted $C_6$-$C_{10}$ aryl; COOR where R represents a hydrogen atom, or an optionally substituted $C_1$-$C_{20}$ alkyl, optionally substituted $C_2$-$C_{20}$ alkenyl or optionally substituted $C_6$-$C_{10}$ aryl, or a pharmaceutically acceptable counter-ion; CONR'R", where R' and R" independently represent a hydrogen atom, an optionally substituted $C_1$-$C_{20}$ alkyl, optionally substituted $C_2$-$C_{20}$ alkenyl or optionally substituted $C_6$-$C_{10}$ aryl; $NH_2$, $C_1$-$C_{20}$ alkylamino, bis(alkylamino), or cycloalkylamino; OH; $C_1$-$C_{20}$ alkoxy; $C_1$-$C_{20}$ alkanoyl; $C_1$-$C_{20}$ acyloxy; halo; $C_1$-$C_{20}$ alkylcarboxylamino; cyano; nitro; $SO_2NR'''R''''$ where R''' and R'''' independently represent a hydrogen atom, $C_1$-$C_{20}$ alkyl or aryl; $SO_2R'''$ where R''' independently represents a hydrogen atom, $C_1$-$C_{20}$ alkyl or aryl; or $SO_3R'''$ where R''' independently represents a hydrogen atom, $C_1$-$C_{20}$ alkyl or aryl;

X represents O;

Y independently represents an oxygen atom or sulfur atom;

Z independently represents $OR_a$, wherein $R_a$ represents a hydrogen atom, or an optionally substituted $C_1$-$C_{20}$ linear or branched alkyl, chloroalkyl or fluoroalkyl, optionally substituted $C_2$-$C_{20}$ linear or branched alkenyl; optionally substituted $C_6$-$C_{10}$ aryl; optionally substituted $C_6$-$C_{20}$ aroyl; optionally substituted $C_1$-$C_{20}$ alkanoyl; or $SO_2R'''$ where R''' represents a hydrogen atom, $C_1$-$C_{20}$ alkyl or aryl; or $NR_bR_c$, wherein $R_b$ and $R_c$ independently represent a hydrogen atom, or an optionally substituted $C_1$-$C_{20}$ linear or branched alkyl, chloroalkyl or fluoroalkyl; optionally substituted $C_2$-$C_{20}$ linear or branched alkenyl; optionally substituted $C_6$-$C_{10}$ aryl; optionally substituted $C_3$-$C_{10}$ cycloalkyl or cycloalkenyl; $COOZ_1$ where $Z_1$ represents an optionally substituted $C_1$-$C_{20}$ alkyl, optionally substituted $C_2$-$C_{20}$ alkenyl or optionally substituted $C_6$-$C_{10}$ aryl; optionally substituted $C_6$-$C_{20}$ aroyl; optionally substituted $C_1$-$C_{20}$ alkanoyl; or $SO_2R'''$ where $R'''$ represents a hydrogen atom, or an $C_1$-$C_{20}$ alkyl or aryl; or $CR_dR_eR_f$, wherein $R_d$, $R_e$ and $R_f$ independently represent a hydrogen atom, or an optionally substituted $C_1$-$C_{20}$ linear or branched alkyl, chloroalkyl or fluoroalkyl, optionally substituted $C_2$-$C_{20}$ linear or branched alkenyl; optionally substituted $C_6$-$C_{10}$ aryl; optionally substituted $C_3$-$C_{10}$ cycloalkyl or cycloalkenyl; COOR where R represents a hydrogen atom, or an optionally substituted $C_1$-$C_{20}$ alkyl, optionally substituted $C_2$-$C_{20}$ alkenyl or optionally substituted $C_6$-$C_{10}$ aryl, sodium, potassium, calcium, magnesium, ammonium, or tromethamine; $NH_2$; $C_1$-$C_{20}$ alkylamino, bis(alkylamino) or cycloalkylamino; OH; optionally substituted $C_1$-$C_{20}$ alkoxy, trifluoromethoxy; optionally substituted $C_1$-$C_{20}$ alkanoyl; optionally substituted $C_1$-$C_{20}$ acyloxy; optionally substituted $C_6$-$C_{20}$ aroyl; halo; cyano; nitro; optionally substituted $C_1$-$C_{20}$ alkylcarboxylamino; $SO_2NR'''R''''$ where $R'''$ and $R'''$ independently represent a hydrogen atom, $C_1$-$C_{20}$ alkyl or aryl; $SO_2R'''$ where $R'''$ independently represents a hydrogen atom, $C_1$-$C_{20}$ alkyl or aryl; or $SO_3R'''$ where $R'''$ independently represents a hydrogen atom, $C_1$-$C_{20}$ alkyl or aryl; or the grouping —C (=Y)Z may represent hydrogen or $R_{12}$ or may be absents.

2. The compound according to claim 1 wherein said compound is represented by Formula I.

3. The compound according to claim 2 wherein the bond represented by a dashed line plus a solid line between the carbons with the group R8 and R9 attached is a double-bond.

4. The compound according to claim 3 wherein at least one of $R_8$ or $R_9$ represents CONR'R", wherein R' and R" independently represent a hydrogen atom, or an alkoxy, optionally substituted $C_1$-$C_{20}$ alkyl, optionally substituted $C_2$-$C_{20}$ alkenyl, optionally substituted $C_3$-$C_{10}$ cycloalkyl, optionally substituted cycloalkenyl, or optionally substituted $C_6$-$C_{10}$ aryl.

5. The compound according to claim 2 wherein at least one of $R_8$ or $R_9$ represents CONR'R", wherein each of R' and R" represent a hydrogen atom.

6. The compound according to claim 5 wherein $R_8$ represents a hydrogen atom.

7. The compound according to claim 6 wherein Y represents an oxygen atom.

8. The compound according to claim 2 wherein Z represents $NR_bR_c$, wherein $R_b$ and $R_c$ independently represent a hydrogen atom, optionally substituted $C_1$-$C_{20}$ linear or branched alkyl, optionally substituted $C_6$-$C_{10}$ aryl, or optionally substituted $C_3$-$C_{10}$ cycloalkyl.

9. The compound according to claim 2 wherein $R_1$ and $R_2$ independently represent an optionally substituted $C_1$-$C_4$ alkoxy.

10. The compound according to claim 9 wherein the grouping —C(=Y)Z represents hydrogen.

11. The compound 3-(3,5-Dimethoxyphenyl)-N,N-dimethyl-2-{4-[4-(3-oxo-3ureido-propyl)-phenoxy]-phenyl}-acrylamide (13).

12. The compound 2-{4-[4-(2Carbamoylethyl)-phenoxy]phenyl}-3-(3,5-dimethoxyphenyl)-N,N-dimethylacrylamide (31).

13. The compound N,N-Dimethy-2-{4-[4-(3-oxo-3-ureidopropyl)-phenoxyl]-phenyl}-3-pyridin-3-yl-acrylamide (73).

14. The compound 2-{4-[4-(2-Carbamoyl-ethyl)-phenoxy]-phenyl}-N,N-dimethyl-3-pyridin-3-yl-acrylamide (77).

15. A pharmaceutical composition comprising the compound of claim 1 and a pharmaceutically acceptable carrier.

16. A pharmaceutical composition comprising the compound of claim 2 and a pharmaceutically acceptable carrier.

17. The composition of claim 16, wherein the composition is suitable for oral administration.

* * * * *

UNITED STATES PATENT AND TRADEMARK OFFICE
CERTIFICATE OF CORRECTION

| | | |
|---|---|---|
| PATENT NO. | : 7,323,496 B2 | |
| APPLICATION NO. | : 10/430677 | |
| DATED | : January 29, 2008 | |
| INVENTOR(S) | : Partha Neogi et al. | |

It is certified that error appears in the above-identified patent and that said Letters Patent is hereby corrected as shown below:

In column 25 at line 33, please amend "}-3-pyridin-3-yl-acrylamide" to read as }-3-(pyridin-3-yl)-acrylamide;

In column 25 at lines 34-35, please amend "N-dimethyl-3-pyridin-3-yl-acrylamide" to read as N-dimethyl-3-(pyridin-3-yl)-acrylamide;

In column 26 at line 64, please amend "-2-pyridin-3-yl-vinyl)-" to read as -2-(pyridin-3-yl)-vinyl)-;

In column 27 at line 24, please amend "-N-pyridine-4-ylacrylamide (60);" to read as -N-(pyridine-4-yl)-acrylamide (60);;

In column 27 at line 4, please amend "-3-pyridin-3-yl-acrylamide" to read as -3-(pyridin-3-yl)-acrylamide;

In column 27 at line 6, please amend "-3-pyridin-3-yl-acrylamide" to read as -3-(pyridin-3-yl)-acrylamide;

In column 53 at line 53, please amend "-3-pyridin-3-ylacrylamide" to read as -3-(pyridin-3-yl)-acrylamide;

In column 53 at lines 58-59, please amend "-3-pyridin-3-ylacrylic" to read as -3-(pyridin-3-yl)-acrylic;

In column 59 at lines 54-55, please amend "-N-pyridine-4-ylacrylamide (60)" to read as -N-(pyridin-4-yl)-acrylamide (60);

In column 73 at lines 36-37, please amend "-2-pyridin-3-ylvinyl)-" to read as -2-(pyridin-3-yl)-vinyl)-;

In column 73 at lines 39-40, please amend "-2-pyridin-3-ylvinyl)-" to read as -2-(pyridin-3-yl)-vinyl)-;

In column 74 at lines 24-25, please amend "-3-pyridin-3-yl-acrylamide" to read as -3-(pyridin-3-yl)-acrylamide;

In column 75 at line 21, please amend "-3-pyridin-3-yl-acrylic" to read as -3-(pyridin-3-yl)-acrylic;

UNITED STATES PATENT AND TRADEMARK OFFICE
CERTIFICATE OF CORRECTION

PATENT NO. : 7,323,496 B2
APPLICATION NO. : 10/430677
DATED : January 29, 2008
INVENTOR(S) : Partha Neogi et al.

It is certified that error appears in the above-identified patent and that said Letters Patent is hereby corrected as shown below:

In column 75 at line 41, please amend "-3-pyridin-3-yl-acrylic" to read as
-3-(pyridin-3-yl)-acrylic;

In column 75 at line 46, please amend "-3-pyridin-3-yl-acrylic" to read as
-3-(pyridin-3-yl)-acrylic;

In column 75 at line 58, please amend "-3-pyridin-3-yl-acrylamide" to read as
-3-(pyridin-3-yl)-acrylamide;

In column 75 at line 60, please amend "-3-pyridin-3-yl-acrylic" to read as
-3-(pyridin-3-yl)-acrylic;

In column 76 at line 15, please amend "-3-pyridin-3-yl-acrylamide" to read as
-3-(pyridin-3-yl)-acrylamide;

In column 76 at line 67, please amend "-3-pyridin-3-yl-acrylic" to read as
-3-(pyridin-3-yl)-acrylic;

In column 77 at lines 4-5, please amend "-3-pyridin-3-yl-acrylic" to read as
-3-(pyridin-3-yl)-acrylic;

In column 77 at line 18, please amend "-3-pyridin-3-yl-acrylamide" to read as
-3-(pyridin-3-yl)-acrylamide;

In column 77 at line 20, please amend "-3-pyridin-3-yl-acrylic" to read as
-3-(pyridin-3-yl)-acrylic;

In column 78 at line 48, please amend "N-dimethyl-3-pyridin-3-yl-propionamide" to read as N-dimethyl-3-(pyridin-3-yl)-propionamide;

In column 79 at line 53, please amend "-3-pyridin-3-ylpropionic acid" to read as
-3-(pyridin-3-yl)-propionic acid;

In column 80 at line 2, please amend "2-pyridin-3-ylethyl)" to read as
2-(pyridin-3-yl)-ethyl);

In column 80 at line 4, please amend "-3-pyridin-3-ylpropionic acid" to read as
-3-(pyridin-3-yl)-propionic acid;

UNITED STATES PATENT AND TRADEMARK OFFICE
CERTIFICATE OF CORRECTION

PATENT NO. : 7,323,496 B2
APPLICATION NO. : 10/430677
DATED : January 29, 2008
INVENTOR(S) : Partha Neogi et al.

It is certified that error appears in the above-identified patent and that said Letters Patent is hereby corrected as shown below:

In column 80 at line 23, please amend "N-dimethyl-3-pyridin-3-yl-propionamide" to read as N-dimethyl-3-(pyridin-3-yl)-propionamide;

In column 80 at line 48, please amend "-3-pyridin-3-yl-propionamide" to read as -3-(pyridin-3-yl)-propionamide;

In column 81 at line 51, please amend "phenyl}-acrylamide (83)" to read as phenyl}-propionamide (83);

In column 82 at lines 20-21, please amend "-phenyl)-propionamide, 13" to read as –phenyl)-acrylamide, 13;

Column 88, lines 25-27 should read,
In Claim 13, please amend "-phenyl}-3-pyridin-3-yl-acrylamide (73)" to read as –phenyl}-3-(pyridin-3-yl)-acrylamide (73); and Column 88, lines 28-30 should read,
In Claim 14, please amend "N-dimethyl-3-pyridin-3-yl-acrylamide (77)" to read as N-dimethyl-3-(pyridin-3-yl)-acrylamide (77).

Signed and Sealed this

Sixteenth Day of December, 2008

JON W. DUDAS
*Director of the United States Patent and Trademark Office*